United States Patent [19]
Hauel et al.

[11] Patent Number: 6,121,308
[45] Date of Patent: Sep. 19, 2000

[54] DISUBSTITUTED BICYCLIC HETEROCYCLES, THE PREPARATION THEREOF AND THEIR USE AS PHARMACEUTICAL COMPOSITIONS

[75] Inventors: Norbert Hauel, Schemmerhofen; Uwe Ries, Biberach; Henning Priepke, Warthausen; Gerhard Mihm; Wolfgang Wienen, both of Biberach; Jean Marie Stassen, Warthausen; Klaus Binder, Wiesbaden; Rainer Zimmermann, Mittelbiberach, all of Germany

[73] Assignee: Boehringer Ingelheim KG, Ingelheim, Germany

[21] Appl. No.: 09/359,487

[22] Filed: Jul. 22, 1999

Related U.S. Application Data
[60] Provisional application No. 60/098,838, Sep. 2, 1998.

[30] Foreign Application Priority Data

Aug. 1, 1998 [DE] Germany ............................ 198 34 751

[51] Int. Cl.$^7$ ...................... A61K 31/415; A61K 31/405; C07D 235/04; C07D 235/10; C07D 209/02
[52] U.S. Cl. ...................... 514/415; 514/394; 548/304.7; 548/309.7; 548/310.1; 548/465; 548/503; 548/509
[58] Field of Search ...................... 514/394, 415; 548/304.7, 309.7, 310.1, 465, 503, 509

[56] References Cited

FOREIGN PATENT DOCUMENTS

| 0 540 051 | 5/1993 | European Pat. Off. . |
| WO97 30971 | 8/1997 | WIPO . |
| WO97 21437 | 6/1999 | WIPO . |

*Primary Examiner*—D. Margaret Seaman
*Attorney, Agent, or Firm*—R. P. Raymond; A. R. Stempel; M-E M. Devlin

[57] ABSTRACT

Novel disubstituted bicyclic heterocycles, of which the following are exemplary:

(a) 1-methyl-2-[(4-amidinophenyl)-oxymethyl]-5-[N-(hydroxycarbonylmethyl)-quinoline-8-sulphonylamino]-benzimidazole, (b) 1-methyl-2-[2-(4-amidinophenyl)-ethyl]-5-[N-(N-(hydroxycarbonylmethyl)-aminocarbonylmethyl)-quinoline-8-sulphonylamino]-benzimidazole, (c) 1-methyl-2-[N-(4-amidinophenyl)-aminomethyl]-5-[N-(hydroxycarbonylmethyl)-quinoline-8-sulphonylamino]-benzimidazole and (d) 1-methyl-2-[N-(4-amidinophenyl)-aminomethyl]-5-[N-(hydroxycarbonylmethyl)-quinoline-8-sulphonylamino]-indole.

These are useful for the treatment of thrombotic disease.

10 Claims, No Drawings

DISUBSTITUTED BICYCLIC HETEROCYCLES, THE PREPARATION THEREOF AND THEIR USE AS PHARMACEUTICAL COMPOSITIONS

RELATED APPLICATIONS

Benefit of U.S. Provisional Application Ser. No. 60/098,838, filed on Sep. 2, 1998 is hereby claimed.

FIELD OF INVENTION

The present invention relates to new disubstituted bicyclic heterocycles of the formula $$R_a\text{—Het—B—Ar—E} \quad (I)$$

their tautomers, stereoisomers, mixtures and the salts thereof, particularly the physiologically acceptable salts thereof with inorganic or organic acids or bases which have valuable properties.

The compounds of the above formula I wherein E denotes a cyano group are valuable intermediate products for preparing the other compounds of formula I, and the compounds of the above formula I wherein E denotes a $R_b$NH—C(=NH)-group, as well as the tautomers and stereoisomers thereof, have valuable pharmacological properties, particularly a thrombin-inhibiting activity and the effect of prolonging the thrombin time.

The present invention thus relates to the new compounds of the above formula I and the preparation thereof, pharmaceutical compositions containing the pharmacologically active compounds and their use.

In the above formula:

B denotes an ethylene group optionally substituted by one or two $C_{1-3}$-alkyl groups, whilst a methylene group of the ethylene group, which is linked to either the Het or Ar group, may be replaced by an oxygen or sulphur atom, by a sulphinyl, sulphonyl, carbonyl or —$NR_1$ group, whilst $R_1$ denotes a hydrogen atom or a $C_{1-6}$-alkyl group, 126 or B also denotes a straight-chained $C_{3-5}$-alkylene group, in which a methylene group, which is linked neither to the Het group nor to the Ar group, is replaced by an —$NR_1$ group wherein $R_1$ is as hereinbefore defined, E denotes a cyano or $R_b$NH—C(=NH)— group wherein
$R_b$ denotes a hydrogen atom, a hydroxy group, a $C_{1-3}$-alkyl group or a group which may be cleaved in vivo, Ar denotes a phenylene or naphthylene group optionally substituted by a fluorine, chlorine or bromine atom, or by a triluoromethyl, $C_{1-3}$-alkyl or $C_{1-3}$-alkoxy group, a thienylene, thiazolylene, pyridinylene, pyrimidinylene, pyazinylene or pyridazinylene group optionally substituted in the carbon skeleton by a $C_{1-3}$-alkyl group, Het denotes a bicyclic heterocycle of the formula

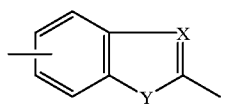

wherein
X denotes a nitrogen atom or a methine group optionally substituted by a $C_{1-3}$-alkyl group and
Y denotes an imino group optionally substituted by a $C_{1-5}$-alkyl or $C_{3-7}$-cycloalkyl group, an oxygen or sulphur atom or X denotes a nitrogen atom and
Y denotes an imino group substituted by a $C_{1-5}$-alkyl or $C_{3-7}$-cycloalkyl group, wherein the alkyl and cycloalkyl substituent in each case is substituted by a carboxy group or a group which can be converted in vivo into a carboxy group, whilst additionally in one of the abovementioned heterocyces a non-angular methine group may be replaced by a nitrogen atom, or Het denotes a group of the formulae

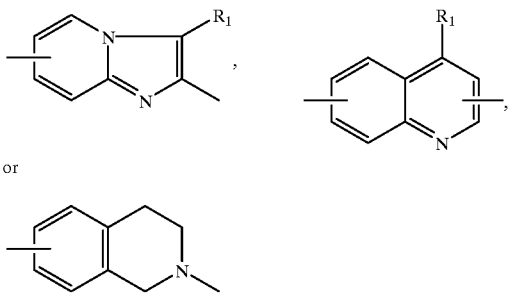

or

wherein
$R_1$ is as hereinbefore defined,
and $R_a$ denotes a phenyl-$C_{1-3}$-alkoxy group,
an amino group,
a $C_{1-3}$-alkylamino group, which is additionally substituted at the nitrogen atom by a phenyl-$C_{1-3}$-alkyl group,
a $R_3$—CO—$R_4$N or $R_3$—$SO_2$-$R_4$N group wherein
$R_3$ denotes a $C_{1-5}$-alkyl, phenyl-$C_{1-3}$-alkyl, $C_{3-7}$-cycloalkyl, phenyl, naphthyl, pyridyl, quinolyl, isoquinolyl, tetrahydroquinolyl or tetrahydroisoquinolyl group and
$R_4$ denotes a hydrogen atom, $C_{1-5}$-alkyl or phenyl-$C_{1-3}$-alkyl group, each of which is substituted in the alkyl moiety by a group which may be converted in vivo into a carboxy group, by a carboxy or tetrazolyl group, by an aminocarbonyl or $C_{1-3}$-alkylaminocarbonyl group, each of which is additionally substituted at the nitrogen atom by a group which may be converted in vivo into a carboxy-$C_{1-3}$-alkyl group or by a carboxy group, a $C_{2-5}$-alkyl group terminally substituted by a di-($C_{1-3}$-alkyl)-amino group, or a $C_{3-7}$-cycloalkyl group.

By a group which may be converted in vivo into a carboxy group is meant, for example, a hydroxymethyl group, a carboxy group esterified with an alcohol wherein the alcoholic moiety is preferably a $C_{1-6}$-alkanol, a phenyl-$C_{1-3}$-alkanol, a $C_{3-9}$-cycloalkanol, whilst a $C_{5-8}$-cycloalkanol may additionally be substituted by one or two $C_{1-3}$-alkyl groups, a $C_{5-8}$-cycloalkanol wherein a methylene group in the 3 or 4 position is replaced by an oxygen atom or by an imino group optionally substituted by a $C_{1-3}$-alkyl, phenyl-$C_{1-3}$-alkyl, phenyl-$C_{1-3}$-alkoxycarbonyl or $C_{2-6}$-alkanoyl group and the cycloalkanol moiety may additionally be substituted by one or two $C_{1-3}$-alkyl groups, a $C_{4-7}$-cycloalkanol, a $C_{3-5}$-alkenol, a phenyl-$C_{3-5}$-alkenol, a $C_{3-5}$-alkynol or phenyl-$C_{3-5}$-alkynol, with the proviso that no bond to the oxygen atom starts from a carbon atom which has a double or triple bond, a $C_{3-8}$cycloalkyl-$C_{1-3}$-alkanol, a bicycloalkanol with a total of 8 to 10 carbon atoms, which is additionally substituted by one or two $C_{1-3}$-alkyl groups in the bicycloalkyl moiety, a 1,3-dihydro-3-oxo-1-isobenzofuranol or an alcohol of formula

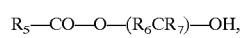

$R_5\text{—CO—O—}(R_6CR_7)\text{—OH,}$ wherein
- $R_5$ denotes a $C_{1-8}$-alkyl, $C_{5-7}$-cycloalkyl, phenyl or phenyl-$C_{1-3}$-alkyl group.
- $R_6$ denotes a hydrogen atom, a $C_{1-3}$-alkyl, $C_{5-7}$-cycloalkyl or phenyl group and
- $R_7$ denotes a hydrogen atom or a $C_{1-3}$-alkyl group, and by a group which can be cleaved in vivo from an imino or amino group is meant, for example, a hydroxy group, an acyl group such as the benzoyl or pyridinoyl group or a $C_{1-16}$-alkanoyl group such as the formyl, acetyl, propionyl, butanoyl, pentanoyl or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert.butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-16}$-alkoxycarbonyl group such as the benzyloxycarbonyl, phenylethoxycarbonyl or phenylpropoxycarbonyl group, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or $R_5CO$—O—($R_6CR_7$)—O—CO group wherein $R_5$ to $R_7$ are as hereinbefore defined.

Moreover, the saturated alkyl and alkoxy moieties which contain more than 2 carbon atoms, as well as the alkanoyl and unsaturated alkyl moieties which contain more than 3 carbon atoms mentioned in the above definitions also include the branched isomers thereof such as, for example, the isopropyl, tert. butyl and isobutyl groups, etc.

Preferred compounds of the above formula I are those wherein
- B denotes an ethylene group optionally substituted by one or two methyl groups, whilst a methylene group of the ethylene group, which is linked to either the Het or Ar group, may be replaced by an oxygen or sulphur atom, by a carbonyl or —$NR_1$ group, whilst
  $R_1$ denotes a hydrogen atom or a methyl group,
- or B also denotes an n-propylene group wherein the central methylene group is replaced by an —$NR_1$ group wherein $R_1$ is as hereinbefore defined,
- E denotes a cyano or $R_b$NH—C(=NH) group wherein
  $R_b$ denotes a hydrogen atom, a $C_{1-8}$-alkyloxy-carbonyl, $C_{5-7}$-cycloalkyloxy-carbonyl, benzoyl, nicotinoyl or isonicotinoyl group,
- Ar denotes a phenylene group optionally substituted by a fluorine, chlorine or bromine atom, by a trifluoromethyl, methyl or methoxy group, or a thienylene group optionally substituted in the carbon skeleton by a methyl group
- Het denotes a bicyclic heterocycle of the formula wherein
- X denotes a nitrogen atom or a methine group optionally substituted by a methyl group and
- Y denotes an imino group optionally substituted by a $C_{1-3}$-alkyl or $C_{3-7}$-cycloalkyl group, an oxygen or sulphur atom or
- X denotes a nitrogen atom and
- Y denotes an imino group substituted by a $C_{1-3}$-alkyl group, whilst the alkyl moiety is additionally substituted by a carboxy or $C_{1-3}$-alkyloxy-carbonyl group, or Het denotes a group of the formulae wherein
- $R_1$ is as hereinbefore defined and
- $R_2$ denotes a $C_{1-3}$-alkyl group substituted by a carboxy or $C_{1-3}$-alkoxy-carbonyl group, and $R_a$ denotes a benzyloxy group, an amino group, a $C_{1-3}$-alkylamino group, which is additionally substituted at the nitrogen atom by a benzyl group, a $R_3$—CO—$R_4$N or $R_3$—$SO_2$—$R_4$N group wherein
- $R_3$ denotes a $C_{1-4}$-alkyl, benzyl, $C_{5-7}$-cycloalkyl, phenyl, pyridyl, quinolyl, isoquinolyl, tetrahydroquinolyl or tetrahydroisoquinolyl group and
- $R_4$ denotes a hydrogen atom, a $C_{1-3}$-alkyl group, which is substituted by a carboxy, $C_{1-3}$-alkoxy-carbonyl, tetrazolyl, aminocarbonyl or $C_{1-3}$-alkylaminocarbonyl group, whilst the aminocarbonyl and $C_{1-3}$-alkylaminocarbonyl group are each additionally substituted at the nitrogen atom by a carboxy-$C_{1-3}$-alkyl or $C_{1-3}$-alkoxy-carbonyl-$C_{1-3}$-alkyl group, or a $C_{2-3}$-alkyl group terminally substituted by a di-($C_{1-3}$-alkyl)-amino group, the isomers and the salts thereof.

Particularly preferred compounds of the above formula I are those wherein
- B denotes an ethylene group optionally substituted by one or two methyl groups, whilst a methylene group of the ethylene group, which is linked to either the Het or Ar group, may be replaced by an oxygen or sulphur atom, by a carbonyl or —$NR_1$ group, wherein
  $R_1$ denotes a hydrogen atom or a methyl group,
- or B also denotes an n-propylene group wherein the central methylene group is replaced by an —$NR_1$ group wherein $R_1$ is as hereinbefore defined,
- E denotes an $R_b$NH—C(=NH) group wherein
  $R_b$ denotes a hydrogen atom, a $C_{1-8}$-alkyloxy-carbonyl, $C_{5-7}$-cycloalkyloxy-carbonyl or benzoyl group,
- Ar denotes a phenylene group optionally substituted by a fluorine, chlorine or bromine atom, by a trifluoromethyl, methyl or methoxy group, or a thienylene group optionally substituted in the carbon skeleton by a methyl group, Het denotes a bicyclic heterocycle of the formula

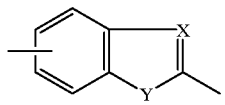

wherein
X denotes a nitrogen atom or a methine group optionally substituted by a methyl group and
Y denotes an imino group optionally substituted by a $C_{1-3}$-alkyl or $C_{3-7}$-cycloalkyl group, or an oxygen or sulphur atom or
X denotes a nitrogen atom and
Y denotes an imino group substituted by a $C_{1-3}$-alkyl group, whilst the alkyl moiety is additionally substituted by a carboxy or $C_{1-3}$-alkyloxy-carbonyl group,
and $R_a$ denotes a benzyloxy group,
an amino group,
a $C_{1-3}$-alkylamino group which is additionally substituted at the nitrogen atom by a benzyl group,
an $R_3$—CO—$R_4$N or $R_3$—SO$_2$—$R_4$N group wherein
$R_3$ denotes a $C_{1-4}$-alkyl, benzyl, $C_{5-7}$-cycloalkyl, phenyl, pyridyl, quinolyl, isoquinolyl, tetrahydroquinolyl or tetrahydroisoquinolyl group and
$R_4$ denotes a hydrogen atom, a $C_{1-3}$-alkyl group which is substituted by a carboxy, $C_{1-3}$-alkoxy-carbonyl, tetrazolyl, aminocarbonyl or $C_{1-3}$-alkylaminocarbonyl group, whilst the aminocarbonyl and $C_{1-3}$-alkylaminocarbonyl group are each additionally substituted at the nitrogen atom by a carboxy-$C_{1-3}$-alkyl or $C_{1-3}$-alkoxy-carbonyl-$C_{1-3}$-alkyl group, or a $C_{2-3}$-alkyl group terminally substituted by a di-($C_{1-3}$-alkyl)-amino group,
particularly those compounds of the above formula I wherein
$R_a$ in the 5 position denotes an $R_3$—CO—$R_4$N or $R_3$—SO$_2$—$R_4$N group wherein $R_3$ and $R_4$ are as hereinbefore defined,
the isomers and the salts thereof.

Most particularly preferred compounds are those of the formula Ia

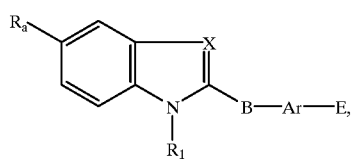

(Ia)

wherein
X denotes a methine group or a nitrogen atom,
B denotes an ethylene group, whilst the methylene group linked to Ar may be replaced by an oxygen atom or a imino group,
Ar denotes a 1,4-phenylene group,
E denotes an amidino group,
$R_1$ denotes a methyl group and
$R_a$ denotes an $R_3$—CO—$R_4$N or $R_3$—SO$_2$—$R_4$N group, whilst
$R_4$ denotes a methyl group substituted by a carboxy, $C_{1-3}$-alkoxy-carbonyl, carboxymethylaminocarbonyl or $C_{1-3}$-alkoxy-carbonylmethylaminocarbonyl group and $R_3$ denotes an isoquinolin-8-yl group,
particularly the abovementioned compounds of formula Ia wherein $R_a$ denotes an $R_3$—SO$_2$—$R_4$N group,
the isomers and the salts thereof.

The following may be mentioned as examples of particularly preferred compounds of the above formula I:
(a) 1-methyl-2-[2-(4-amidinophenyl)-oxymethyl]-5-[N-(hydroxycarbonylmethyl)-quinoline-8-sulphonylamino]-benzimidazole,
(b) 1-methyl-2-[2-(4-amidinophenyl)-ethyl]-5-[N-(N'-(hydroxycarbonylmethyl)-aminocarbonylmethyl)-quinoline-8-sulphonylamino]-benzimidazole,
(c) 1-methyl-2-[N-(4-amidinophenyl)-aminomethyl]-5-[N-(hydroxycarbonylmethyl)-quinoline-8-sulphonylamino]-benzimidazole and
(d) 1-methyl-2-[N-(4-amidinophenyl)-aminomethyl]-5-[N-(hydroxycarbonylmethyl)-quinoline-8-sulphonylamino]-indole
and the salts thereof.

The new compounds may be prepared by methods known per se, for example by the following processes:
a. In order to prepare a compound of formula I wherein E denotes a $R_bNH$—C(=NH) group in which $R_b$ denotes a hydrogen atom, a hydroxy or $C_{1-3}$-alkyl group:
reacting a compound of the formula $$R_a\text{—Het—B—Ar—C(=NH)—Z}_1, \quad\quad (II)$$

optionally formed in the reaction mixture
wherein
B, Ar, Het and $R_a$ are as hereinbefore defined and
$Z_1$ denotes an alkoxy or aralkoxy group such as the methoxy, ethoxy, n-propoxy, isopropoxy or benzyloxy group or an alkylthio or aralkylthio group such as the methylthio, ethylthio, n-propylthio or benzylthio group, with an amine of the formula $$H_2N\text{—}R_b' \quad\quad (III)$$

wherein
$R_b'$ denotes a hydrogen atom, a hydroxy or $C_{1-3}$-alkyl group.

The reaction is conveniently carried out in a solvent such as methanol, ethanol, n-propanol, water, methanol/water, tetrahydrofuran or dioxane at temperatures between 0 and 150° C., preferably at temperatures between 20 and 120° C., with a compound of formula III or with a corresponding acid addition salt such as ammonium carbonate, for example.

A compound of formula II is obtained for example by reacting a compound of formula I wherein E denotes a cyano group with a corresponding alcohol such as methanol, ethanol, n-propanol, isopropanol or benzylalcohol in the presence of an acid such as hydrochloric acid or by reacting a corresponding amide with a trialkyloxonium salt such as triethyloxonium-tetrafluoroborate in a solvent such as methylene chloride, tetrahydrofuran or dioxane at temperatures between 0 and 50° C., but preferably at 20° C., or a corresponding nitrile with hydrogen sulphide appropriately in a solvent such as pyridine or dimethylformamide and in the presence of a base such as triethylamine and subsequent alkylation of the thioamide formed with a corresponding alkyl or aralkyl halide.

b. In order to prepare a compound of formula I wherein the $R_a$ group and E are as hereinbefore defined with the proviso that the $R_a$ group contains a carboxy group and E is as hereinbefore defined or the $R_a$ group is as hereinbefore defined and E denotes a $NH_2-C(=NH)$ group or the $R_a$ group contains a carboxy group and E denotes a $NH_2-C(=NH)$ group:

converting a compound of the formula

$$R_a'-Het-B-Ar-E', \qquad (IV)$$

wherein

A, B, Ar and Het are as hereinbefore defined and the $R_a'$ group and E' have the meanings given for the $R_a$ group and E hereinbefore, with the proviso that the $R_a'$ group contains a group which may be converted into a carboxyl group by hydrolysis, treatment with an acid or base, thermolysis or hydrogenolysis and E is as hereinbefore defined or E' denotes a group which may be converted into an $NH2-C(=NH)$ group by hydrolysis, treatment with an acid or base, thermolysis or hydrogenolysis and the $R_a'$ group has the meanings given for the $R_a$ group hereinbefore or the $R_a'$ group contains a group which may be converted into a carboxyl group by hydrolysis, treatment with an acid or base, thermolysis or hydrogenolysis and E' denotes a group which may be converted into an $NH_2-C(=NH)$ group by hydrolysis, treatment with an acid or base, thermolysis or hydrogenolysis, by hydrolysis, treatment with an acid or base, thermolysis or hydrogenolysis into a compound of formula I wherein the $R_a$ group and E are as hereinbefore defined, with the proviso that the $R_a$ group contains a carboxy group and E is as hereinbefore defined or the $R_a$ group has the meanings given hereinbefore and E denotes a $NH_2-C(=NH)$ group or the $R_a$ group contains a carboxy group and E denotes a $NH_2-(C=NH)$ group.

An example of a group which can be converted into a carboxy group might be a carboxyl group protected by a protecting group such as the functional derivatives thereof, e.g. the unsubstituted or substituted amides, esters, thioesters, trimethylsilylesters, orthoesters or iminoesters thereof, which are appropriately converted by hydrolysis into a carboxyl group, the esters thereof with tertiary alcohols, e.g. the tert.butyl ester, which are appropriately converted into a carboxyl group by treatment with an acid or thermolysis, and the esters thereof with aralkanols, e.g. the benzylester, which are appropriately converted into a carboxyl group by hydrogenolysis.

The hydrolysis is appropriately carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane at temperatures between −10 and 120° C., e.g. at temperatures between ambient temperature and the boiling temperature of the reaction mixture.

If the $R_a'$ group and/or E' in a compound of formula IV for example contains the tert.butyl or tert.butyloxycarbonyl group, these may also be cleaved by treating with an acid such as trifluoroacetic acid, formic acid, p-toluenesulphonic acid, sulphuric acid, hydrochloric acid, phosphoric acid or polyphosphoric acid, optionally in an inert solvent such as methylene chloride, chloroform, benzene, toluene, diethylether, tetrahydrofuran or dioxane, preferably at temperatures between −10 and 120° C., e.g. at temperatures between 0 and 60° C., or also thermally, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40 and 120° C.

If the $R_a'$ group and/or E' in a compound of formula IV contains, for example, the benzyloxy or benzyloxycarbonyl group, these may also be cleaved hydrogenolytically in the presence of a hydrogenation catalyst such as palladium/charcoal in a suitable solvent such as methanol, ethanol, ethanol/water, glacial acetic acid, ethyl acetate, dioxane or dimethylformamide preferably at temperatures between 0 and 50° C., e.g. at ambient temperature, and a hydrogen pressure of 1 to 5 bar.

c. In order to prepare a compound of formula I wherein the $R_a$ group contains one of the ester groups mentioned in the definition of the $R_a$ group:

reacting a compound of the formula

$$R_a''-Het-B-Ar-E, \qquad (V)$$

wherein

B, E, Ar and Het are as hereinbefore defined and the $R_a''$ group has the meanings given for the $R_a$ group hereinbefore, with the proviso that the $R_a''$ group contains a carboxyl group or a group which can be converted into a corresponding ester group by means of an alcohol, with an alcohol of the formula

$$HO-R_8, \qquad (VI)$$

wherein $R_8$ represents the alkyl moiety of one of the above-mentioned groups which can be cleaved in vivo with the exception of the $R_5-CO-O-(R_5CR_7)$ group for a carboxyl group, or with the formamide acetals thereof or with a compound of the formula

$$Z_2-R_9, \qquad (VII)$$

wherein $R_9$ denotes the alkyl moiety of one of the above-mentioned groups which can be cleaved in vivo with the exception of the $R_5-CO-O-(R_5CR_7)$ group for a carboxyl group and $Z_2$ denotes a leaving group such as a halogen atom, e.g. a chlorine or bromine atom.

The reaction with an alcohol of formula VI is appropriately carried out in a solvent or mixture of solvents such as methylene chloride, benzene, toluene, chlorobenzene, tetrahydrofuran, benzene/tetrahydrofuran or dioxane, but preferably in an alcohol of formula VI, optionally in the presence of an acid such as hydrochloric acid or in the presence of a dehydrating agent, e.g. in the presence of isobutyl chloroformate, thionylchloride, trimethylchlorosilane, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole, triphenylphosphine/carbon tetrachloride or triphenylphosphine/diethyl azodicarboxylate, optionally in the presence of a base such as potassium carbonate, N-ethyl-diisopropylamine or N,N-dimethylaminopyridine, appropriately at temperatures between 0 and 150° C., preferably at temperatures between 0 and 80° C.

With a compound of formula VII the reaction is appropriately carried out in a solvent such as methylene chloride, tetrahydrofuran, dioxane, dimethylsulphoxide, dimethylformamide or acetone optionally in the presence of a reaction accelerator such as sodium or potassium iodide and preferably in the presence of a base such as sodium carbonate or potassium carbonate or in the presence of a tertiary organic base such as N-ethyl-diisopropylamine or N-methylmorpholine, which may simultaneously also serve as the solvent, or optionally in the presence of silver carbonate or silver oxide at temperatures between −30 and 100° C., but preferably at temperatures between −10 and 80° C.

d. In order to prepare a compound of general formula I wherein $R_b$ denotes a group which may be cleaved in vivo: reacting a compound of general formula

$$R_a\text{—Het—B—Ar—C(=NH)—NH}_2, \qquad (VIII)$$

wherein $R_a$, Het, B and Ar are as hereinbefore defined, with a compound of general formula

$$Z_3\text{—}R_{10}, \qquad (IX)$$

wherein $R_{10}$ denotes a group which may be cleaved in vivo and $Z_3$ denotes a nucleofugic leaving group such as a halogen atom, e.g. a chlorine, bromine or iodine atom.

The reaction is preferably carried out in a solvent such as methanol, ethanol, methylene chloride, tetrahydrofuran, toluene, dioxane, dimethylsulphoxide or dimethylformamide optionally in the presence of an inorganic or a tertiary organic base, preferably at temperatures between 20° C. and the boiling temperature of the solvent used.

With a compound of general formula IX, wherein $Z_3$ denotes a nucleofugic leaving group, the reaction is preferably carried out in a solvent such as methylene chloride, acetonitrile, tetrahydrofuran, toluene, dimethylformamide or dimethylsulphoxide, optionally in the presence of a base such as sodium hydride, potassium carbonate, potassium-tert.butoxide or N-ethyl-diisopropylamine at temperatures between 0 and 60° C.

e. In order to prepare a compound of general formula I wherein $R_a$ denotes an amino group and E denotes a cyano group:
reduction of a nitro compound of general formula

$$NO_2\text{—Het—B—Ar—CN}, \qquad (X)$$

wherein

B, Ar and Het are as hereinbefore defined.

The reduction is preferably carried out hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid optionally with the addition of an acid such as hydrochloric acid at temperatures between 0 and 50° C., but preferably at ambient temperature, and at a hydrogen pressure of 1 to 7 bar, but preferably 3 to 5 bar. This may also be carried out with nascent hydrogen, e.g. with zinc/glacial acetic acid, zinc/hydrochloric acid or iron and suitable salts thereof/hydrochloric acid.

f. In order to prepare a compound of general formula I wherein $R_a$ denotes an amino group and E denotes a cyano group:

Cleaving a protecting group for an amino group from a compound of general formula

$$R_a'''\text{—Het—B—Ar—CN}, \qquad (XI)$$

wherein

B, Ar and Het are as hereinbefore defined and $R_a'''$ denotes an amino group protected by a protecting group.

A protecting group for an amino group might be, for example, the acetyl, trifluoroacetyl, benzoyl, ethoxycarbonyl, tert.butoxycarbonyl, benzyloxycarbonyl, benzyl, methoxybenzyl, 2,4-dimethoxybenzyl or phthalyl group.

A protecting group used is preferably cleaved hydrolytically in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C., a benzyl, methoxybenzyl or benzyloxycarbonyl group is preferably cleaved hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 3 to 5 bar, a methoxybenzyl group may also be cleaved in the presence of an oxidising agent such as cerium(IV)ammonium nitrate in a solvent such as methylene chloride, acetonitrile or acetonitrile/water at temperatures between 0 and 50° C., but preferably at ambient temperature, a 2,4-dimethoxybenzyl group is preferably cleaved in trifluoroacetic acid in the presence of anisol, a tert.butyl or tert.butyloxycarbonyl group is preferably cleaved by treating with an acid such as trifluoroacetic acid or hydrochloric acid, optionally using a solvent such as methylene chloride, dioxane or ether, a phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C., an allyloxycarbonyl group may also be cleaved by treating with a catalytic amount of tetrakis-(triphenylphosphine)-palladium(O) preferably in a solvent such as tetrahydrofuran and preferably in the presence of an excess of a base such as morpholine or 1,3-dimedone at temperatures between 0 and 100° C., preferably at ambient temperature and under inert gas, or by treating with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

g. In order to prepare a compound of general formula I wherein $R_a$ denotes an $R_3$—CO—$R_4$N or $R_3$—$SO_2$—$R_4$N group and E denotes a cyano group:
reacting a compound of general formula

$$R_4NH\text{—Het—B—Ar—CN}, \qquad (XII)$$

wherein $R_4$, Het, B and Ar are as hereinbefore defined, with a compound of general formula

R₃—X—Z₄,   (XIII)

wherein
R₃ is as hereinbefore defined,
X denotes a carbonyl or sulphonyl group and
Z₄ denotes a nucleofugic leaving group such as a halogen atom, e.g. a chlorine, bromine or iodine atom, or, if X represents a carbonyl group, Z₄ together with a hydrogen atom of the adjacent nitrogen atom represents another carbon-nitrogen bond.

The reaction is preferably carried out in a solvent such as methanol, ethanol, methylene chloride, tetrahydrofuran, toluene, dioxane, dimethylsulphoxide or dimethylformamide optionally in the presence of an inorganic or a tertiary organic base, preferably at temperatures between 20° C. and the boiling temperature of the solvent used.

With a compound of general formula XIII, wherein Z₄ denotes a nucleofugic leaving group, the reaction is preferably carried out in a solvent such as methylene chloride, acetonitrile, tetrahydrofuran, toluene, dimethylformamide or dimethylsulphoxide optionally in the presence of a base such as sodium hydride, potassium carbonate, pyridine, potassium-tert.butoxide or N-ethyl-diisopropylamine at temperatures between 0 and 60° C.

h. In order to prepare a compound of general formula I wherein $R_a$ denotes an $R_3$—CO—$R_4$N or $R_3$—SO₂—$R_4$N group and E denotes a cyano group, wherein $R_4$ has the meanings given hereinbefore, with the exception of the hydrogen atom:
reacting a compound of general formula R₃—X—NH—Het—B—Ar—CN,   (XIV)

wherein
R₃, Het, B, Ar and X are as hereinbefore defined, with a compound of general formula

R₄'—Z₅,   (XV)

wherein
R₄' has the meanings given for R₄ hereinbefore with the exception of the hydrogen atom and
Z₅ denotes a nucleofugic leaving group such as a halogen atom, e.g. a chlorine, bromine or iodine atom.

The reaction is preferably carried out in a solvent such as methylene chloride, acetonitrile, acetone, tetrahydrofuran, toluene, dimethylformamide or dimethylsulphoxide, appropriately in the presence of a base such as sodium hydride, potassium carbonate, pyridine, 1,8-diazobicyclo[5.4.0]undec-7-ene, potassium tert.butoxide or N-ethyl-diisopropylamine at temperatures between 0 and 60° C.

i. In order to prepare a compound of general formula I wherein R₄ denotes a $C_{1-5}$-alkyl or phenyl-$C_{1-3}$-alkyl group, each of which is substituted in the alkyl moiety by a group which may be converted in vivo into a carboxy group, by a tetrazolyl group, by an aminocarbonyl or $C_{1-3}$-alkylaminocarbonyl group, each of which is additionally substituted at the nitrogen atom by a group which can be converted in vivo into a carboxy-$C_{1-3}$-alkyl group and E denotes a cyano group:
reacting a compound of general formula R₃—X—NR₄'—Het—B—Ar—CN,   (XVI)

wherein
R₃, Het, B, Ar and X are as hereinbefore defined and
R₄' denotes a $C_{1-5}$-alkyl or phenyl-$C_{1-3}$-alkyl group, each of which is substituted in the alkyl moiety by a group which may be converted in vivo into a carboxy group, by a tetrazolyl group, by an aminocarbonyl or $C_{1-3}$-alkylaminocarbonyl group, each of which is additionally substituted at the nitrogen atom by a group which can be converted in vivo into a carboxy-$C_{1-3}$-alkyl group, or the reactive derivatives thereof, with a compound of general formula

R₁₁—H,   (XVII)

wherein
R₄' has the meanings given for R₄ hereinbefore with the exception of the hydrogen atom and
R₁₁ denotes one of the substituents of the $C_{1-5}$-alkyl or phenyl-$C_{1-3}$-alkyl group mentioned in the definition of the group R₄ hereinbefore which is attached to the group R₁₁ via a carbonyl group.

The reaction of a carboxylic acid of general formula XVI is optionally carried out in a solvent or mixture of solvents such as methylene chloride, dimethylformamide, benzene, toluene, chlorobenzene, tetrahydrofuran, benzene/tetrahydrofuran or dioxane, optionally in the presence of a dehydrating agent, e.g. in the presence of isobutyl chloroformate, tetraethyl orthocarbonate, trimethyl orthoacetate, 2,2-dimethoxypropane, tetramethoxysilane, thionylchloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium-tetrafluoroborate, 2-(1 H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylaminopyridine, N-methyl-morpholine or triethylamine, appropriately at temperatures between 0 and 150° C., preferably at temperatures between 0 and 100° C.

The reaction of a corresponding reactive compound of general formula XVI such as the esters, imidazolides or halides thereof with an amine of general formula XVII is preferably carried out in a corresponding amine as solvent optionally in the presence of another solvent such as methylene chloride or ether and preferably in the presence of a tertiary organic base such as triethylamine, N-ethyl-diisopropylamine or N-methyl-morpholine at temperatures between 0 and 150° C., preferably at temperatures between 50 and 100° C.

j. In order to prepare a benzimidazolyl, benzothiazolyl or benzoxazolyl compound of general formula I wherein B denotes an ethylene group:
reacting a compound optionally formed in the reaction mixture of general formula

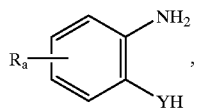
(XVIII)

wherein
$R_a$ and Y are as hereinbefore defined, with a compound of general formula HO—CO—B'—Ar—E,   (IXX)

wherein

Ar and E are as hereinbefore defined and

B' denotes an ethylene group optionally substituted by one or two $C_{1-3}$-alkyl groups.

The reaction is appropriately carried out in a solvent or mixture of solvents such as methylene chloride, dimethylformamide, benzene, toluene, chlorobenzene, tetrahydrofuran, benzene/tetrahydrofuran or dioxane optionally in the presence of a dehydrating agent, e.g. in the presence of isobutyl chloroformate, tetraethyl orthocarbonate, trimethyl orthoacetate, 2,2-dimethoxypropane, tetramethoxysilane, thionylchloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium tetrafluoroborate, 2-(1H-benzotriazol-1-yl)-1,1,3,3-tetramethyluronium tetrafluoroborate/1-hydroxy-benzotriazole, N,N'-carbonyldiimidazole or triphenylphosphine/carbon tetrachloride, and optionally with the addition of a base such as pyridine, 4-dimethylaminopyridine, N-methyl-morpholine or triethylamine, appropriately at temperatures between 0 and 150° C., preferably at temperatures between 0 and 100° C.

The reaction of a corresponding reactive compound of general formula IXX such as the esters, imidazolides or halides thereof with an amine of general formula XVIII is preferably carried out in a solvent such as methylene chloride, ether or tetrahydrofuran and preferably in the presence of a tertiary organic base such as triethylamine, N-ethyl-diisopropylamine or N-methyl-morpholine, which may simultaneously serve as the solvent, at temperatures between 0 and 150° C., preferably at temperatures between 50 and 100° C.

k. In order to prepare a compound of general formula I, which contains one of the abovementioned tetrahydroquinoline or -isoquinoline groups:

hydrogenation of a compound of general formula I which contains one of the abovementioned quinoline or isoquinoline groups.

The hydrogenation is preferably carried out in the presence of an acid such as hydrochloric acid with hydrogen in the presence of a catalyst such as palladium/charcoal and in a solvent such as methanol, ethanol, ethyl acetate, dimethylformamide, dimethylformamide/acetone or glacial acetic acid at temperatures between 0 and 50° C., but preferably at ambient temperature, and at a hydrogen pressure of 1 to 7 bar, but preferably 3 to 5 bar.

In the reactions described hereinbefore, any reactive groups present such as hydroxy, carboxy, amino, alkylamino or imino groups may be protected during the reaction by conventional protecting groups which are cleaved again after the reaction.

For example, a protecting group for a hydroxy group may be a trimethylsilyl, acetyl, benzoyl, tert.butyl, trityl, benzyl or tetrahydropyranyl group, protecting groups for a carboxy group may be a trimethylsilyl, methyl, ethyl, tert.butyl or benzyl group and protecting groups for an amino, alkylamino or imino group may be the acetyl, hydroxy, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a hydroxy, benzyl, methoxybenzyl or benzyloxycarbonyl group is cleaved, for example, hydrogenolytically, e.g. with hydrogen in the presence of a catalyst such as palladium/charcoal in a suitable solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 3 to 5 bar.

A methoxybenzyl group can also be cleaved in the presence of an oxidising agent such as cerium(IV)ammonium nitrate in a solvent such as methylene chloride, acetonitrile or acetonitrile/water at temperatures between 0 and 50° C., but preferably at ambient temperature.

A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

An allyloxycarbonyl group is cleaved by treating with a catalytic amount of tetrakis-(triphenylphosphine)-palladium (O) preferably in a solvent such as tetrahydrofuran and preferably in the presence of an excess of a base such as morpholine or 1,3-dimedone at temperatures between 0 and 100° C., preferably at ambient temperature and under inert gas, or by treating with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

The compounds of general formulae II to IXX used as starting materials, some of which are known from the literature, are obtained by methods known from the literature, and furthermore their preparation is described in the Examples.

Thus, for example, a compound of general formula II is obtained by reacting a corresponding nitrile, which is in turn appropriately obtained according to processes f to h, with a corresponding thiol or alcohol in the presence of hydrogen chloride or bromide.

A compound of general formulae IV, V, VIII, X, XI and IXX used as starting material is appropriately obtained by one of the methods according to the present invention.

Moreover, the compounds of general formula I obtained may be resolved into the enantiomers and/or diastereomers thereof.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid, maleic acid, benzoic acid, methanesulphonic or toluenesulphonic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned hereinbefore, the new compounds of general formula I and their salts have valuable properties. Thus, the compounds of general formula I wherein E denotes a cyano group or $R_a$ denotes an amino group and E denotes a cyano group, are valuable intermediates for preparing the other compounds of general formula I and the compounds of general formula I wherein E denotes a $R_b$NH—C(=NH) group, as well as their tautomers, their stereoisomers and the physiologically acceptable salts thereof, have valuable pharmacological properties, particularly a thrombin-inhibiting activity, the effect of prolonging thrombin time and an inhibiting effect on related serine proteases such as e.g. trypsin, urokinase, factor VIIa, factor Xa, factor IX, factor XI and factor XII, whilst some compounds such as for example the compound of Example 16 also have an inhibitory effect on thrombocyte aggregation.

For example, the compounds

A=1-methyl-2-[(4-amidinophenyl)-oxymethyl]-5-[N-(hydroxycarbonylmethyl)-quinoline-8-sulphonylamino]-benzimidazole, B=1-methyl-2-[2-(4-amidinophenyl)-ethyl]-5-[N-(N'-(hydroxycarbonylmethyl)-aminocarbonylmethyl)-quinoline-8-sulphonylamino]-benzimidazole, C=1-methyl-2-[N-(4-amidinophenyl)-aminomethyl]-5-[N-(hydroxycarbonylmethyl)-quinoline-8-sulphonylamino]-benzimidazole and D=1-methyl-2-[N-(4-amidinophenyl)-aminomethyl]-5-[N-(hydroxycarbonylmethyl)-quinoline-8-sulphonylamino]-indole were investigated for their effect on thrombin time as follows:

Materials: plasma, from human citrated blood.

Test thrombin (bovine), 30 U/ml, Behring Werke, Marburg

Diethylbarbiturate acetate buffer, ORWH 60/61, Behring Werke, Marburg

Biomatic B10 coagulometer, Sarstedt

Method:

The thrombin time was determined using a Biomatic B10 coagulometer made by Messrs. Sarstedt.

As the test substance, 0.1 ml of human citrated plasma and 0.1 ml diethylbarbiturate buffer (DBA buffer) were added to the test strip prescribed by the manufacturer. The mixture was incubated for one minute at 37° C. The clotting reaction was started by the addition of 0.3 U test thrombin in 0.1 ml DBA buffer. The time is measured using the apparatus from the addition of the thrombin up to the clotting of the mixture. Mixtures to which 0.1 ml of DBA buffer were added were used as the controls.

According to the definition, a dosage-activity curve was used to determine the effective concentration of the substance, i.e. the concentration at which the thrombin time is double compared with the control.

The Table which follows contains the results found:

| Substance | Thrombin time ($ED_{200}$ in $\mu$M) |
| --- | --- |
| A | 0.015 |
| B | 0.016 |
| C | 0.031 |
| D | 0.054 |

By way of example, no acute toxic side effects were observed when the compounds were administered to rats in the above dosage range. The compounds are thus well tolerated.

In view of their pharmacological properties the new compounds and the physiologically acceptable salts thereof are suitable for the prevention and treatment of venous and arterial thrombotic diseases, such as for example the treatment of deep leg vein thrombosis, for preventing reocclusions after bypass operations or angioplasty (PT(C)A), and occlusion in peripheral arterial diseases such as pulmonary embolism, disseminated intravascular coagulation, for preventing coronary thrombosis, stroke and the occlusion of shunts or stents. In addition, the compounds according to the invention are suitable for antithrombotic support in thrombolytic treatment, such as for example with rt-PA or streptokinase, for preventing long-term restenosis after PT(C)A, for preventing metastasis and the growth of clot-dependent tumours and fibrin-dependent inflammatory processes, e.g. in the treatment of pulmonary fibrosis.

The dosage required to achieve such an effect is appropriately 0.01 to 10 mg/kg, preferably 0.03 to 3 mg/kg, by intravenous route, and 0.1 to 10 mg/kg, preferably 0.3 to 5 mg/kg by oral route, in each case administered 1 to 4 times a day. For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples which follow are intended to illustrate the invention:

Preliminary Remarks

Unless otherwise specified, the $R_f$ values were always determined using polygram silica gel plates produced by Messrs. E. Merck of Darmstadt.

The EKA mass spectra (electrospray mass spectra of cations) are described, for example, in *Chemie unserer Zeit* 6, 308–316 (1991).

EXAMPLE 1

1-methyl-2-[2-(4-amidinophenyl)-ethyl]-5-[N-(ethoxycarbonylmethyl)-methanesulphonylamino]-benzimidazole a. 1-methyl-2-[2-(4-cyanophenyl)-ethyl]-5-nitro-benzimidazole 2.3 g (0.014 mol) of 2-methylamino-5-nitro-aniline and 2.7 g (0.0154 mol) of 4-cyanophenylpropionic acid are refluxed for 1 hour in 25 ml phosphorus oxychloride. After cooling, water is added and the mixture is made alkaline with ammonia. The precipitate is suction filtered, washed with water and dried.

Yield: 3.8 g (89% of theory), $R_f$-value: 0.28 (silica gel; dichloromethane/methanol=50:1).

b. 1-methyl-2-[2-(4-cyanophenyl)-ethyl]-5-amino-benzimidazole 3.8 g (0.0124 mol) of 1-methyl-2-[2-(4-cyanophenyl)-ethyl]-5-nitro-benzimidazole are dissolved in 100 ml methanol and 100 ml dichloromethane and after the addition of 0.5 g of 5 10% palladium on activated charcoal the mixture is hydrogenated with hydrogen. Then the catalyst is filtered off and the filtrate is evaporated down.

Yield: 3.2 g (93% of theory), $R_f$-value: 0.38 (silica gel; dichloromethane/methanol=9:1).

c. 1-methyl-2-[2-(4-cyanophenyl)-ethyl]-5-methanesulphonylamino-benzimidazole 1.6 g (5.8 mmol) of 1-methyl-2-[2-(4-cyanophenyl)-ethyl]-5-amino-benzimidazole and 0.66 g (5.8 mmol) of methanesulphonic acid chloride are stirred into 30 ml pyridine for 3 hours at ambient temperature. Then 1 ml of water is added and the mixture is evaporated down. The residue is diluted with ethyl acetate and water, the crystalline product is suction filtered and dried.

Yield: 1.4 g (68% of theory), $R_f$-value: 0.70 (silica gel; dichloromethane/methanol=9:1).

d. 1-methyl-2-[2-(4-cyanophenyl)-ethyl]-5-[N-(ethoxycarbonylmethyl)-methanesulphonylamino]-benzimidazole 1.4 g (3.95 mmol) of 1-methyl-2-[2-(4-cyanophenyl)-ethyl]-5-methanesulphonylamino-benzimidazole, 0.73 g (4.4 mmol) of bromoethyl acetate and 2.8 g (20 mmol) of potassium carbonate are dissolved in 200 ml acetone and refluxed for 2 hours. Then the mixture is filtered off and the solution is evaporated down.

Yield: 1.6 g (92% of theory), $R_f$-value: 0.76 (silica gel; dichloromethane/methanol=9:1).

e. 1-methyl-2-[2-(4-amidinophenyl)-ethyl]-5-[N-(ethoxycarbonylmethyl)-methanesulphonylamino]-benzimidazole 1.6 g (3.63 mmol) of 1-methyl-2-[2-(4-cyanophenyl)-ethyl]-5-[N-(ethoxycarbonylmethyl)-methanesulphonylamino]-benzimidazole are dissolved in 50 ml of saturated ethanolic hydrochloric acid and stirred for 5 hours at ambient temperature. Then the solvent is distilled off, the residue is dissolved in 30 ml of absolute ethanol and mixed with 3.5 g (3.63 mmol) of ammonium carbonate. After 18 hours at ambient temperature the mixture is evaporated to dryness and the residue is chromatographed on silica gel (methylene chloride/methanol=5:1). The corresponding fractions are concentrated by evaporation, the residue obtained is triturated with ether and suction filtered.

Yield: 0.9 g (50% of theory), $R_f$-value: 0.36 (silica gel; dichloromethane/methanol=5:1); $C_{22}H_{27}N_5O_4S(457.55)$; Mass spectrum: $(M+H)^+$=458; $(M+Na)^+$=480.

EXAMPLE 2

1-methyl-2-[2-(4-amidinophenyl)-ethyl]-5-[N-(ethoxycarbonylmethyl)-benzenesulphonylamino]-benzimidazole a. 1-methyl-2-[2-(4-cyanophenyl)-ethyl]-5-[N-(ethoxycarbonylmethyl)-benzenesulphonylamino]-benzimidazole Prepared analogously to Example 1d from 1-methyl-2-[2-(4-cyanophenyl)-ethyl]-5-benzenesulphonylamino-benzimidazole, bromoethyl acetate and potassium carbonate in acetone.

Yield: 54% of theory, $R_f$-value: 0.84 (silica gel; dichloromethane/methanol=9:1).

b. 1-methyl-2-[2-(4-amidinophenyl)-ethyl]-5-[N-(ethoxycarbonylmethyl)-benzenesulphonylamino]-benzimidazole Prepared analogously to Example 1e from 1-methyl-2-[2-(4-cyanophenyl)-ethyl]-5-[N-(ethoxycarbonylmethyl)-benzenesulphonylamino]-benzimidazole and hydrochloric acid/ammonium carbonate in ethanol.

Yield: 59% of theory, $R_f$-value: 0.38 (silica gel; dichloromethane/methanol=5:1); $C_{27}H_{29}N_5O_4S(519.6)$; Mass spectrum: $(M+H)^+$=520; $(M+Na)^+$=542.

EXAMPLE 3

1-methyl-2-[2-(4-amidinophenyl)-ethyl]-5-[N-(hydroxycarbonylmethyl)-benzenesulphonylamino]-benzimidazole 0.52 g (0.93 mmol) of 1-methyl-2-[2-(4-amidinophenyl)-ethyl]-5-[N-(ethoxycarbonylmethyl)-benzenesulphonylamino]-benzimidazole and 0.4 g (0.01 mol) of sodium hydroxide are stirred in 5 ml water and 10 ml ethanol for three hours at ambient temperature. Then the mixture is diluted with water and adjusted to pH 4 with glacial acetic acid. The crystalline precipitate is suction filtered and dried.

Yield: 77% of theory, $C_{25}H_{25}N_5O_4S(491.66)$; Mass spectrum: $(M+H)^+$=492; $(M+Na)^+$=514; $(M-H+2Na)^+$=536; $(2M+H+Na)^{++}$=503.

EXAMPLE 4

1-methyl-2-[2-(4-amidinophenyl)-ethyl]-5-[N-(hydroxycarbonylmethyl)-methanesulphonylamino]-benzimidazole Prepared analogously to Example 3 from 1-methyl-2-[2-(4-amidinophenyl)-ethyl]-5-[N-(ethoxycarbonylmethyl)-methanesulphonylamino]-benzimidazole and sodium hydroxide solution.

Yield: 97% of theory, $C_{20}H_{23}N_5O_4S(429.5)$; Mass spectrum: $(M+H)^+$=430; $(M+Na)^+$=452; $(2M+H+Na)^{2+}$=441; $(2M+3Na)^{3+}$=309.

EXAMPLE 5

1-ethoxycarbonylmethyl-2-[(4-amidinophenyl)-oxymethyl]-5-[N-(2-dimethylaminoethyl)-benzenesulphonylamino]-benzimidazole a. Mixture of 1-ethoxycarbonylmethyl-2-[(4-cyanophenyl)-oxymethyl]-5-nitro-benzimidazole and 1-ethoxycarbonylmethyl-2-[(4-cyanophenyl)-oxymethyl]-6-nitro Prepared analogously to Example 1d from 1H-2-[(4-cyanophenyl)-oxymethyl]-5-nitro-benzimidazole, bromoethyl acetate and potassium carbonate in acetone.

Yield: 3.6 g (95% of theory), $R_f$-value: 0.56 (silica gel; dichloromethane/methanol=19:1).

b. Mixture of 1-ethoxycarbonylmethyl-2-[(4-cyanophenyl)-oxymethyl]-5-amino-benzimidazole and 1-ethoxycarbonylmethyl-2-[(4-cyanophenyl)-oxymethyl]-6-amino-benzimidazole 3.6 g (9.5 mmol) of the mixture of 1-ethoxycarbonylmethyl-2-[(4-cyanophenyl)-oxymethyl]-5-nitro-benzimidazole and 1-ethoxycarbonylmethyl-2-[(4-cyanophenyl)-oxymethyl]-6-nitro-benzimidazole are dissolved in 200 ml methanol and after the addition of 0.5 g 10% palladium on activated charcoal, the mixture is hydrogenated with hydrogen. Then the catalyst is filtered off and the filtrate is evaporated down. The residue is chromatographed on silica gel (methylene chloride +1 to 5% ethanol).

Yield: 1.2 g (36% of theory) 1-ethoxycarbonylmethyl-2-[(4-cyanophenyl)-oxymethyl]-5-amino-benzimidazole; $R_f$-value: 0.10 (silica gel; dichloromethane/methanol=19:1); Yield: 1.0 g (30% of theory) 1-ethoxycarbonylmethyl-2-[(4-cyanophenyl)-oxymethyl]-6-amino-benzimidazole; $R_f$-value: 0.32 (silica gel; dichloromethane/methanol=19:1).

c. 1-ethoxycarbonylmethyl-2-[(4-cyanophenyl)-oxymethyl]-5-benzenesulphonilamino-benzimidazole Prepared analogously to Example 1c from 1-ethoxycarbonylmethyl-2-[(4-cyanophenyl)-oxymethyl]-5-amino-benzimidazole and benzenesulphonic acid chloride in pyridine.

Yield: 100% of theory, $R_f$-value: 0.43 (silica gel; dichloromethane/methanol=9:1).

d. 1-ethoxycarbonylmethyl-2-[(4-cyanophenyl)-oxymethyl]-5-[N-(2-dimethylaminoethyl)-benzenesulphonylamino]-benzimidazole 1.65 g (3.4 mmol) of 1-ethoxycarbonylmethyl-2-[(4-cyanophenyl)-oxymethyl]-5-benzenesulphonylamino-benzimidazole and 518.4 mg (3.6 mmol) of 2-dimethylaminoethylchloride-hydrochloride are dissolved in 100 ml acetone and after the addition of 2.0 g potassium carbonate and 737 mg (4.85 mmol) of 1,8-diazabicyclo[5.4.0]undec-7-ene the mixture is refluxed for 11 hours. Then it is filtered and evaporated down. The residue is chromatogra-phed on silica gel (methylene chloride/5–10% ethanol).

Yield: 750 mg (39% of theory), $R_f$-value: 0.21 (silica gel; dichloromethane/methanol=9:1).

e. 1-ethoxycarbonylmethyl-2-[(4-amidinophenyl)-oxymethyl]-5-[N-(2-dimethylaminoethyl)-benzenesulphonylamino]-benzimidazole Prepared analogously to Example 1e from 1-ethoxycarbonylmethyl-2-[(4-cyanophenyl)-oxymethyl]-5-[N-(2-dimethylaminoethyl)-benzenesulphonylamino]-benzimidazole and hydrochloric acid/ammonium carbonate in ethanol.

Yield: 85% of theory, $C_{29}H_{34}N_6O_5S(578.7)$; Mass spectrum: $(M+H)^+=579$; $(M+2H)^{++}=290$.

EXAMPLE 6

1-ethoxycarbonylmethyl-2-[(4-amidinophenyl)-oxymethyl]-6-[N-(2-dimethylaminoethyl)-benzenesulphonylamino]-benzimidazole a. 1-ethoxycarbonylmethyl-2-[(4-cyanophenyl-oxymethyl]-6-benzenesulphonylamino-benzimidazole Prepared analogously to Example 1c from 1-ethoxycarbonylmethyl-2-[(4-cyanophenyl)-oxymethyl]-6-amino-benzimidazole and benzenesulphonic acid chloride in pyridine.

Yield: 80% of theory, $R_f$-value: 0.72 (silica gel; dichloromethane/methanol=9:1).

b. 1-ethoxycarbonylmethyl-2-[(4-cyanophenyl)-oxymethyl]-6-[N-(2-dimethylaminoethyl)-benzenesulphonylamino]-benzimidazole Prepared analogously to Example 5d from 1-ethoxycarbonylmethyl-2-[(4-cyanophenyl)-oxymethyl]-6-benzenesulphonylamino-benzimidazole, 2-dimethylaminoethylchloride-hydrochloride, potassium carbonate and 1,8-diazabicyclo[5.4.0]undec-7-ene in acetone.

Yield: 24% of theory, $R_f$-value: 0.34 (silica gel; dichloromethane/methanol=9:1).

c. 1-ethoxycarbonylmethyl-2-[(4-amidinophenyl)-oxymethyl]-6-[N-(2-dimethylaminoethyl)-benzenesulphonylamino]-benzimidazole Prepared analogously to Example 1e from 1-ethoxycarbonylmethyl-2-[(4-cyanophenyl)-oxymethyl]-6-[N-(2-dimethylaminoethyl)-benzenesulphonylamino]-benzimidazole and hydrochloric acid/ammonium carbonate in ethanol.

Yield: 67% of theory, $C_{29}H_{34}N_6O_5S(578.7)$; Mass spectrum: $(M+H)^+=579$; $(M+2H)^{++}=290$.

EXAMPLE 7

1-hydroxycarbonylmethyl-2-[(4-amidinophenyl)-oxymethyl]-5-[N-(2-dimethylaminoethyl)-benzenesulphonylamino]-benzimidazole Prepared analogously to Example 3 from 1-ethoxycarbonylmethyl-2-[(4-amidinophenyl)-oxymethyl]-5-[N-(2-dimethylaminoethyl)-benzenesulphonylamino]-benzimidazole and sodium hydroxide solution.

Yield: 91% of theory, $C_{27}H_{30}N_6O_5S(550.65)$; Mass spectrum (EKA): $(M+H)^+=551$; $(M+2H)^{++}=276$.

EXAMPLE 8

1-ethoxycarbonylmethyl-2-[(4-amidinophenyl)-oxymethyl]-5-[N-(2-dimethylaminoethyl-methanesulphonylamino]-benzimidazole Prepared analogously to Example 1e from 1-ethoxycarbonylmethyl-2-[(4-cyanophenyl)-oxymethyl]-5-[N-(2-dimethylaminoethyl)-methanesulphonylamino]-benzimidazole with ethanolic hydrochloric acid and ammonium carbonate.

Yield: 96% of theory, $C_{24}H_{32}N_6O_5S(516.6)$; Mass spectrum (EKA): $(M+H)^+=517$; $(M+2H)^{++}=259$.

EXAMPLE 9

1-ethoxycarbonylmethyl-2-[(4-amidinophenyl)-oxymethyl]-6-[N-(2-dimethylaminoethyl)-methanesulphonylamino]-benzimidazole Prepared analogously to Example 1e from 1-ethoxycarbonylmethyl-2-[(4-cyanophenyl)-oxymethyl]-

6-[N-(2-dimethylaminoethyl)-methanesulphonylamino]-benzimidazole and ethanolic hydrochloric acid, ethanol and ammonium carbonate.

Yield: 69% of theory, $C_{24}H_{32}N_6O_5S(516.6)$; Mass spectrum (EKA): $(M+H)^+=517$; $(M+2H)^{++}=259$.

EXAMPLE 10

1-hydroxycarbonylmethyl-2-[(4-amidinophenyl)-oxymethyl]-6-[N-(2-dimethylaminoethyl)-methanesulphonylamino]-benzimidazole Prepared analogously to Example 3 from 1-ethoxycarbonylmethyl-2-[(4-amidinophenyl)-oxymethyl]-6-[N-(2-dimethylaminoethyl)-methanesulphonylamino]-benzimidazole and sodium hydroxide solution.

Yield: 92% of theory, $C_{22}H_{28}N_6O_5S(488.67)$; Mass spectrum (EKA): $(M+H)^+=489$; $(M+2H)^{++}=245$.

EXAMPLE 11

1-hydroxycarbonylmethyl-2-[(4-amidinophenyl)-oxymethyl]-5-[N-(2-dimethylaminoethyl)-methanesulphonylamino]-benzimidazole Prepared analogously to Example 3 from 1-ethoxycarbonylmethyl-2-[(4-amidinophenyl)-oxymethyl]-5-[N-(2-dimethylaminoethyl)-methanesulphonylamino]-benzimidazole and sodium hydroxide solution.

Yield: 98% of theory, $C_{22}H_{28}N_6O_5S(488.6)$; Mass spectrum (EKA): $(M+H)^+=489$; $(M+2H)^{++}=245$.

EXAMPLE 12

1-methyl-2-[(4-amidinolphenyl)-oxymethyl]-5-[N-(ethoxyacarbonylmethyl)-quinoline-8-sulphonylamino]-benzimidazole Prepared analogously to Example 1e from 1-methyl-2-[(4-cyanophenyl)-oxymethyl]-5-[N-(ethoxycarbonylmethyl)-quinoline-8-sulphonylamino]-benzimidazole and ethanolic hydrochloric acid, ethanol and ammonium carbonate.

Yield: 70% of theory, $C_{29}H_{28}N_6O_5S(572.65)$; Mass spectrum (EKA): $(M+H)^+=573$; $(M+2H)^{++}=287$; $(M+H+Na)^{++}=298$.

EXAMPLE 13

1-ethyl-2-[2-(4-amidinophenyl)-ethyl]-5-[N-(ethoxycarbonylmethyl)-quinoline-8-sulphonylamino]-benzimidazole Prepared analogously to Example 1e from 1-ethyl-2-[2-(4-cyanophenyl)-ethyl]-5-[N-(ethoxycarbonylmethyl)-quinoline-8-sulphonylamino]-benzimidazole and ethanolic hydrochloric acid, ethanol and ammonium carbonate.

Yield: 85% of theory, $C_{31}H_{32}N_6O_4S(584.71)$; $R_f$-value: 0.32 (silica gel; dichloromethane/methanol=5:1); Mass spectrum (EKA): $(M+H)^+=585$; $(M+H+Na)^{++}=304$; $(M+2H)^{++}=293$.

EXAMPLE 14

1-methyl-2-[2-(4-amidinophenyl)-ethyl]-5-[N-(ethoxycarbonylmethyl)-quinoline-8-sulphonylamino]-benzimidazole Prepared analogously to Example 1e from 1-methyl-2-[2-(4-cyanophenyl)-ethyl]-5-[N-(ethoxycarbonylmethyl)-quinoline-8-sulphonylamino]-benzimidazole and ethanolic hydrochloric acid, ethanol and ammonium carbonate.

Yield: 71% of theory, $C_{30}H_{30}N_6O_4S(570.68)$; $R_f$-value: 0.30 (silica gel; dichloromethane/methanol=5:1); Mass spectrum (EKA): $(M+H)^+=571$; $M+H+Na)^{++}=297$; $(M+2H)^{++}=286$.

EXAMPLE 15

1-cyclopropyl-2-[2-(4-amidinophenyl)-ethyl]-5-[N-(ethoxycarbonylmethyl)-quinoline-8-sulphonylamino]-benzimidazole Prepared analogously to Example 1e from 1-cyclopropyl-2-[2-(4-cyanophenyl)-ethyl]-5-[N-(ethoxycarbonylmethyl)-quinoline-8-sulphonylamino]-benzimidazole and ethanolic hydrochloric acid, ethanol and ammonium carbonate.

Yield: 76% of theory, $C_{32}H_{32}N_6O_4S(596.72)$; $R_f$-value: 0.34 (silica gel; dichloromethane/methanol=5:1); Mass spectrum (EKA): $(M+H)^+=597$; $(M+H+Na)^{++}=310$; $(M+2H)^{++}=299$.

EXAMPLE 16

1-methyl-2-[(4-amidinophenyl)-oxymethyl]-5-[N-(hydroxycarbonylmethyl)-quinoline-8-sulphonylamino]-benzimidazole Prepared analogously to Example 3 from 1-methyl-2-[(4-amidinophenyl)-oxymethyl]-5-[N-(ethoxycarbonylmethyl)-quinoline-8-sulphonylamino]-benzimidazole and sodium hydroxide solution.

Yield: 43% of theory, $C_{27}H_{24}N_6O_5S(544.6)$; Mass spectrum (EKA): $(M+H)^+=545$; $(M+Na)^+=567$; $(M-H)^-=543$; $(2M+2Na+H)^{3+}=378.7$; $^1$H-NMR ($d_6$-DMSO): $\delta=3.90$ (s,3H); 5.05 (s,2H); 5.73 (s,2H); 7.09 (dd,1H); 7.38 (d,2H); 7.52 (d,1H); 7.57–7.74 (m,2H); 7.80 (dd,1H); 7.92 (d,2H); 8.13 (d,1H); 8.31 (d,1H); 8,61 (dd,1H); 9.12–9.30 (m,3H); 9.38 (s,2H) ppm.

EXAMPLE 17

1-ethyl-2-[2-(4-amidinophenyl)-ethyl]-5-[N-(hydroxycarbonylmethyl)-quinoline-8-sulphonylamino]-benzimidazole Prepared analogously to Example 3 from 1-ethyl-2-[2-(4-amidinophenyl)-ethyl]-5-[N-(ethoxycarbonylmethyl)-quinoline-8-sulphonylamino]-benzimidazole and sodium hydroxide solution.

Yield: 74% of theory, $C_{29}H_{28}N_6O_4S(556.65)$; Mass spectrum (EKA): $(M+H)^+=557$; $(M+Na)^+=579$.

EXAMPLE 18

1-methyl-2-[2-(4-amidinophenyl)-ethyl]-5-[N-(hydroxycarbonylmethyl)-quinoline-8-sulphonylamino]-benzimidazole Prepared analogously to Example 3 from 1-methyl-2-[2-(4-amidinophenyl)-ethyl]-5-[N-(ethoxycarbonylmethyl)-quinoline-8-sulphonylamino]-benzimidazole and sodium hydroxide solution.

Yield: 96% of theory, $C_{28}H_{26}N_6O_4S(542.59)$; Mass spectrum (EKA): $(M+H)^+=543$; $(M+Na)^+=565$; $(2M+3Na)^{3+}=385$.

EXAMPLE 19

1-cyclopropyl-2-[2-(4-amidinophenyl)-ethyl]-5-[N-(hydroxycarbonylmethyl)-quinoline-8-sulphonylamino]-benzimidazole Prepared analogously to Example 3 from 1-cyclopropyl-2-[2-(4-amidinophenyl)-ethyl]-5-[N-

(ethoxycarbonylmethyl)-quinoline-8-sulphonylamino]-benzimidazole and sodium hydroxide solution.

Yield: 88% of theory, $C_{30}H_{28}N_6O_4S(568.66)$; Mass spectrum (EKA): $(M+H)^+=569$; $(M+Na)^+=591$; $(2M+3Na)^{3+}=402$.

EXAMPLE 20

1-ethyl-2-[2(4-amidinophenyl)-oxymethyl]-5-[N-(ethyloxycarbonylmethyl)-quinoline-8-sulphonylamino]-benzimidazole Prepared analogously to Example 1e from 1-ethyl-2-[(4-cyanophenyl)-oxymethyl]-5-[N-(ethoxycarbonylmethyl)-quinoline-8-sulphonylamino]-benzimidazole and ethanolic hydrochloric acid, ethanol and ammonium carbonate.

Yield: 81% of theory, $C_{30}H_{30}N_6O_5S(586.7)$; Mass spectrum (EKA): $(M+H)^+=587$; $(M+H+Na)^{++}=305$; $(M+2H)^{++}=294$.

EXAMPLE 21

1-ethyl-2-[(4-amidinophenyl)-oxymethyl]-5-[N-(hydroxycarbonylmethyl)-quinoline-8-sulphonylamino]-benzimidazole Prepared analogously to Example 3 from 1-ethyl-2-[(4-amidinophenyl)-oxymethyl]-5-[N-(ethoxycarbonylmethyl)-quinoline-8-sulphonylamino]-benzimidazole and sodium hydroxide solution.

Yield: 96% of theory, $C_{28}H_{26}N_6O_5S(558.6)$; Mass spectrum (EKA): $(M+H)^+=559$; $(M+Na)^+=581$; $(M-H)^-=557$.

EXAMPLE 22

1-methyl-2-[(4-amidinophenyl)-oxymethyl]-5-[N-(ethoxycarbonylmethyl)-benzenesulphonylamino]-benzimidazole Prepared analogously to Example 1e from 1-methyl-2-[(4-cyanophenyl)-oxymethyl]-5-[N-(ethoxycarbonylmethyl)-benzenesulphonylamino]-benzimidazole and ethanolic hydrochloric acid, ethanol and ammonium carbonate.

Yield: 48% of theory, $C_{26}H_{27}N_5O_5S(521.6)$; Mass spectrum (EKA): $(M+H)^+=522$; $(M+H+Na)^{++}=272.8$.

EXAMPLE 23

1-methyl-2-[2-(4-amidinophenyl)-ethyl]-5-[N-(N'-(ethoxycarbonylmethyl)-aminocarbonylmethyl)-quinoline-8-sulphonylamino]-benzimidazole a. 1-methyl-2-[2-(4-cyanophenyl)-ethyl]-5-[N-(hydroxycarbonylmethyl)-quinoline-8-sulphonylamino]-benzimidazole Prepared analogously to Example 3 from 1-methyl-2-[2-(4-cyanophenyl)-ethyl]-5-[N-(ethoxycarbonylmethyl)-quinoline-8-sulphonylamino]-benzimidazole and sodium hydroxide in ethanol/water.

Yield: 92% of theory, $R_f$-value: 0.24 (silica gel; dichloromethane/methanol=9:1).

b. 1-methyl-2-[2-(4-cyanophenyl)-ethyl]-5-[N-(N'-(ethoxycarbonylmethyl)-aminocarbonylmethyl)-quinoline-8-sulphonylamino]-benzimidazole 2.1 g (0.004 mol) of 1-methyl-2-[2-(4-cyanophenyl)-ethyl]-5-[N-(hydroxycarbonylmethyl)-quinoline-8-sulphonylamino]-benzimidazole and 0.65 g (0.004 mol) of N,N'-carbonyldiimidazole are dissolved in 30 ml of dimethylformamide and stirred for 45 minutes at 80° C. Then 0.71 g (0.0046 mol) of glycine ethylester and 0.51 g (0.005 mol) of triethylamine are added and the mixture is stirred for a further four hours at 80° C. The solvent is concentrated by evaporation and the residue is chromatographed on silica gel (methylene chloride/ethanol=50:1).

Yield: 44% of theory, $R_f$-value: 0.74 (silica gel; dichloromethane/methanol=9:1).

c. 1-methyl-2-[2-(4-amidinophenyl)-ethyl]-5-[N-(N'-(ethoxycarbonylmethyl)-aminocarbonylmethyl)-quinoline-8-sulphonylamino]-benzimidazole Prepared analogously to Example 1e from 1-methyl-2-[2-(4-cyanophenyl)-ethyl]-5-[N-(N'-(ethoxycarbonylmethyl)-aminocarbonylmethyl)-quinoline-8-sulphonylamino]-benzimidazole and hydrochloric acid/ammonium carbonate in ethanol.

Yield: 86% of theory, $C_{32}H_{33}N_7O_5S(627.73)$; Mass spectrum: $(M+H)^+=628$; $(M+2H)^{++}=314.8$; $(M+H+Na)^{++}=325.7$.

EXAMPLE 24

1-methyl-2-[2-(4-amidinophenyl)-ethyl]-5-[N-(N'-ethoxy-carbonylmethyl-N'-methyl-aminocarbonylmethyl)-quinoline-8-sulphonylamino]-benzimidazole Prepared analogously to Example 1e from 1-methyl-2-[2-(4-cyanophenyl)-ethyl]-5-[N-(N'-ethoxycarbonylmethyl-N'-methyl-aminocarbonylmethyl)-quinoline-8-sulphonylamino]-benzimidazole and ethanolic hydrochloric acid, ethanol and ammonium carbonate.

Yield: 63% of theory, $C_{33}H_{35}N_7O_5S(641.76)$; $R_f$-value: 0.30 (silica gel; dichloromethane/methanol=5:1); Mass spectrum (EKA): $(M+H)^+=642$; $(M+H+Na)^{++}=332.8$; $(M+2H)^{++}=321.7$.

EXAMPLE 25

1-methyl-2-[2-(4-amidinophenyl)-ethyl]-5-[N-(N'-(hydroxycarbonylmethyl)-aminocarbonylmethyl)-quinoline-8-sulphonylamino]-benzimidazole Prepared analogously to Example 3 from 1-methyl-2-[2-(4-amidinophenyl)-ethyl]-5-[N-(N'-(ethoxycarbonylmethyl)-aminocarbonylmethyl)-quinoline-8-sulphonylamino]-benzimidazole and sodium hydroxide solution.

Yield: 87% of theory, $C_{30}H_{29}N_7O_5S(599.68)$; Mass spectrum (EKA): $(M+H)^+=600$; $(M+H+Na)^{++}=311.8$; $(M+Na)^+=622$; $(M+2H)^{++}=300.8$; $(2M+H+2Na)^{3+}=415$; $(2M+3Na)^{3+}=422.7$; $^1$H-NMR ($d_6$-DMSO+DCl): δ=3.29 (t,2H); 3.51 (t,2H); 3.80 (s,2H); 3.87 (s,3H); 5.01 (s,2H); 7.10 (dd,1H); 7.56–7.90 (m,8H); 8.17 (d,1H); 8.38 (d,1H); 8,68 (dd,1H); 9.26 (dd,1H) ppm.

EXAMPLE 26

1-methyl-2-[2-(4-amidinophenyl)-ethyl]-5-[N-(N'-hydroxycarbonylmethyl-N'-methyl-aminocarbonylmethyl)-quinoline-8-sulphonylamino]-benzimidazole Prepared analogously to Example 3 from 1-methyl-2-[2-(4-amidinophenyl)-ethyl]-5-[N-(N'-ethoxycarbonylmethyl-N'-methyl-aminocarbonylmethyl)-quinoline-8-sulphonylamino]-benzimidazole and sodium hydroxide solution.

Yield: 97% of theory, $C_{31}H_{31}N_7O_5S(613.71)$; Mass spectrum (EKA): $(M+H)+614$; $(M+Na)^+=636$; $(M+2H)^{++}=307.7$; $(M+H+Na)^{++}=318.6$; $(M+2Na)^{++}=329.6$.

EXAMPLE 27

1-methyl-2-[(4-amidinophenyl)-oxymethyl]-5-[N-(hydroxycarbonylmethyl)-benzenesulphonylamino]-benzimidazole Prepared analogously to Example 3 from 1-methyl-2-[(4-amidinophenyl)-oxymethyl]-5-[N-(ethoxycarbonylmethyl)-benzenesulphonylamino]-benzimidazole and sodium hydroxide solution.

Yield: 79% of theory, $C_{24}H_{23}N_5O_5S$(493.6); Mass spectrum (EKA): $(M+H)^+=494$; $(M+Na)^+=516$; $(M-H)^-=492$.

EXAMPLE 28

1-methyl-2-[N-(4-amidinophenyl)-aminomethy]-5-[N-(methoxycarbonylmethyl)-quinoline-8-sulphonylamino]-benzimidazole Prepared analogously to Example 1e from 1-methyl-2-[N-(4-cyanophenyl)-aminomethyl]-5-[N-(methoxycarbonylmethyl)-quinoline-8-sulphonylamino]-benzimidazole and methanolic hydrochloric acid, methanol and ammonium carbonate.

Yield: 65% of theory, $C_{28}H_{27}N_7O_4S$(557.64); $R_f$-value: 0.33 (silica gel; dichloromethane/methanol=5:1); Mass spectrum (EKA): $(M+H)^+=558$; $(M+2H)^{++}=279.7$; $(M+H+Na)^{++}=290.7$.

EXAMPLE 29

1-methyl-2-[2-(4-amidinophenyl)-ethyl]-5-[N-(methoxycarbonylmethyl)-quinoline-8-sulphonylamino]-benzimidazole Prepared analogously to Example 1e from 1-methyl-2-[2-(4-cyanophenyl)-ethyl]-5-[N-(methoxycarbonylmethyl)-quinoline-8-sulphonylamino]-benzimidazole and methanolic hydrochloric acid, methanol and ammonium carbonate.

Yield: 78% of theory, $C_{29}H_{28}N_6O_4S$(556.65); $R_f$-value: 0.29 (silica gel; dichloromethane/methanol=5:1); Mass spectrum (EKA): $(M+H)^+=557$; $(M+2H)^{++}=579$; $(M+H+Na)^{++}=290.3$.

EXAMPLE 30

1-methyl-2-[N-(4-amidinophenyl)-aminomethyl]-5-[N-(hydroxycarbonylmethyl)-quinoline-8-sulphonylamino]-benzimidazole Prepared analogously to Example 3 from 1-methyl-2-[N-(4-amidinophenyl)-aminomethyl]-5-[N-(ethoxycarbonylmethyl)-quinoline-8-sulphonylamino]-benzimidazole and sodium hydroxide solution.

Yield: 91% of theory, $C_{27}H_{25}N_7O_4S$(543.62); Mass spectrum (EKA): $(M+H)^+=544$; $(M+Na)^+=566$; $(M+H+Na)^{++}=283.8$; $(M+2Na)^{++}=294.6$; $^1$H-NMR (d$_6$-DMSO): δ=3.70 (s,3H); 4.60 (broad s,4H); 6.45 (dd,1H); 6.72 (d,2H); 7.09 (d,1H); 7.30–7.60 (m,5H); 7.73 (dd,1H); 8.08 (d,1H); 8.11–8.35 (m,3H); 8.53 (dd,1H); 9,18 (dd,1H); 11.55 (broad s,2H) ppm.

EXAMPLE 31

1-methyl-2-[2-(4-(N-ethoxycarbonylamidino)phenyl)-ethyl]-5-[N-(methoxycarbonylmethyl)-quinoline-8-sulphonylamino]-benzimidazole 0.8 g (1.34 mmol) of 1-methyl-2-[2-(4-amidinophenyl)-ethyl]-5-[N-(methoxycarbonylmethyl)-quinoline-8-sulphonylamino]-benzimidazole are dissolved in 50 ml tetrahydrofuran and 10 ml water and after the addition of 0.55 g (4.0 mmol) of potassium carbonate the mixture is stirred for 10 minutes at ambient temperature. Then 0.17 g (1.6 mmol) of ethyl chloroformate are added and the mixture is stirred for a further 60 minutes at ambient temperature. Then the organic phase is separated off, dried and evaporated down. The residue is chromatographed on silica gel (methylene chloride/methanol=30:1). The corresponding fractions are concentrated by evaporation, triturated with ether and suction filtered.

Yield: 0.41 g (49% of theory), $R_f$-value: 0.57 (silica gel; dichloromethane/methanol=9:1); $C_{32}H_{32}N_6O_6S$(628.71); Mass spectrum: $(M+H)^+=629$; $(M+Na)^+=651$; $(M+2H)^{++}=315$.

EXAMPLE 32

1-methyl-2-[1-(4-amidinophenoxy)-1-methyl-ethyl]-5-[N-(ethoxycarbonylmethyl)-benzenesulphonylamino]-benzimidazole Prepared analogously to Example 1e from 1-methyl-2-[1-(4-cyanophenoxy)-1-methyl-ethyl]-5-[N-(ethoxycarbonylmethyl)-benzenesulphonylamino]-benzimidazole and ethanolic hydrochloric acid, ethanol and ammonium carbonate.

Yield: 31% of theory, $C_{28}H_{31}N_5O_5S$(549.7); Mass spectrum (EKA): $(M+H)^+=550$; $(M+Na)^+=572$.

EXAMPLE 33

1-methyl-2-[N-(4-amidinophenyl)-aminomethyl]-5-benzyloxy-benzimidazole a. 1-methyl-2-[N-(4-cyanophenyl)-aminomethyl]-5-benzyloxy-benzimidazole Prepared analogously to Example 1a from 2-methylamino-5-benzyloxy-aniline and 4-cyanophenylaminoacetic acid in phosphorus oxychloride.

Yield: 11% of theory, Melting point: >350° C.; $R_f$-value: 0.60 (silica gel; ethyl acetate).

b. 1-methyl-2-[N-(4-amidinophenyl)-aminomethyl]-5-benzyloxy-benzimidazole

Prepared analogously to Example 1e from 1-methyl-2-[N-(4-cyanophenyl)-aminomethyl]-5-benzyloxy-benzimidazole and hydrochloric acid/ammonium carbonate in ethanol.

Yield: 66% of theory, $R_f$-value: 0.23 (silica gel; dichloromethane/methanol=4:1); $C_{23}H_{23}N_5O$(385.47); Mass spectrum: $(M+H)^+=386$; $(M+2H)^{++}=193.5$.

EXAMPLE 34

1-methyl-2-[(4-amidinophenyl)-oxymethyl]-5-[N-(methoxycarbonylmethyl)-quinoline-8-sulphonylamino)-benzimidazole Prepared analogously to Example 1e from 1-methyl-2-[(4-cyanophenyl)-oxymethyl]-5-[N-(methoxycarbonylmethyl)-quinoline-8-sulphonylamino)-benzimidazole and methanolic hydrochloric acid, methanol and ammonium carbonate.

Yield: 68% of theory, $C_{28}H_{26}N_6O_5S$(558.6); Mass spectrum (EKA): $(M+H)^+=559$; $(M+2H)^{++}=280$; $(M+H+Na)^{++}=291$.

EXAMPLE 35

1-ethoxycarbonylmethy-2-[(4-amidinophenyl)-oxymethyl]-5-(quinoline-8-sulphonylamino)-benzimidazole Prepared analogously to Example 1e from 1-ethoxycarbonylmethyl-2-[(4-cyanophenyl)-oxymethyl]-

5-(quinoline-8-sulphonylamino)-benzimidazole and ethanolic hydrochloric acid, ethanol and ammonium carbonate.

Yield: 86% of theory, $C_{28}H_{26}N_6O_5S(558.6)$; Mass spectrum (EKA): $(M+H)^+=559$; $(M+Na)^+=581$; $(M+2H)^{++}=280$.

EXAMPLE 36

1-methyl-2-[(4-(N-ethoxycarbonylamidino)phenyl)-oxymethyl]-5-[N-(methoxycarbonylmethyl)-quinoline-8-sulphonylamino]-benzimidazole Prepared analogously to Example 31 from 1-methyl-2-[(4-amidinophenyl)-oxymethyl]-5-[N-(methoxycarbonylmethyl)-quinoline-8-sulphonylamino]-benzimidazole and ethyl chloroformate.

Yield: 25% of theory, $R_f$-value: 0.34 (silica gel; dichloromethane/ethanol=19:1); Mass spectrum (EKA): $(M+H)^+=631$; $(M+Na)^+=653$; $(M+H+Na)^{++}=327$.

EXAMPLE 37

1-(3-ethoxycarbonylpropyl)-2-[(4-amidinophenyl)-oxymethyl]-5-(quinoline-8-sulphonylamino)-benzimidazole Prepared analogously to Example 1e from 1-(3-ethoxycarbonylpropyl)-2-[(4-cyanophenyl)-oxymethyl]-5-(quinoline-8-sulphonylamino)-benzimidazole and ethanolic hydrochloric acid, ethanol and ammonium carbonate.

Yield: 63% of theory, $C_{30}H_{30}N_5O_5S(586.7)$; Mass spectrum (EKA): $(M+H)^+=587$; $(M+Na)^+=609$; $(M+2H)^{++}=294$.

EXAMPLE 38

1-hydroxycarbonylmethyl-2-[(4-amidinophenyl)-oxymethyl]-5-(quinoline-8-sulphonylamino)-benzimidazole Prepared analogously to Example 3 from 1-ethoxycarbonylmethyl-2-[(4-amidinophenyl)-oxymethyl]-5-(quinoline-8-sulphonylamino)-benzimidazole and sodium hydroxide solution.

Yield: 97% of theory, $C_{26}H_{22}N_6O_5S(530.6)$; Mass spectrum (EKA): $(M+H)^+=531$; $(M+Na)^+=553$.

EXAMPLE 39

1-(3-hydroxycarbonylpropyl)-2-[(4-amidinophenyl)-oxymethyl]-5-(quinoline-8-sulphonylamino)-benzimidazole Prepared analogously to Example 3 from 1-(3-ethoxycarbonylpropyl)-2-[(4-amidinophenyl)-oxymethyl]-5-(quinoline-8-sulphonylamino)-benzimidazole and sodium hydroxide solution.

Yield: 91% of theory, $C_{28}H_{26}N_6O_5S(558.6)$; Mass spectrum (EKA): $(M+H)^+=559$; $(M+Na)^+=581$; $(M+2H)^{++}=280$; $(M+H+Na)^{++}=291$; $(M+H+K)^{++}=299$.

EXAMPLE 40

1-methyl-2-[(4-(N-cyclohexyloxycarbonylamidino)phenyl)-oxymethyl]-5-[N-(methoxycarbonylmethyl)-quinoline-8-sulphonylamino)-benzimidazole Prepared analogously to Example 31 from 1-methyl-2-[(4-amidino-phenyl)-oxymethyl]-5-[N-(methoxycarbonylmethyl)-quinoline-8-sulphonylamino]-benzimidazole and cyclohexyl chloroformate.

Yield: 44% of theory, $C_{35}H_{36}N_6O_7S(684.8)$; Mass spectrum (EKA): $(M+H)^+=685$; $(M+Na)^+=707$; $(M+H+Na)^{++}=354$.

EXAMPLE 41

1-methyl-2-[(3-amidinophenyl)-oxymethyl]-5-benzenesulphonylamino-benzimidazole

Prepared analogously to Example 1e from 1-methyl-2-[(3-cyanophenyl)-oxymethyl]-5-(benzenesulphonylamino)-benzimidazole and ethanolic hydrochloric acid, ethanol and ammonium carbonate.

Yield: 65% of theory, $C_{22}H_{21}N_5O_3S(435.52)$; Mass spectrum (EKA): $(M+H)^+=436$; $(M+Na)^+=458$.

EXAMPLE 42

1-methyl-2-[(3-amidinophenyl)-oxymethyl]-5-(quinoline-8-sulphonylamino)-benzimidazole Prepared analogously to Example 1e from 1-methyl-2-[(3-cyanophenyl)-oxymethyl]-5-(quinoline-8-sulphonylamino)-benzimidazole and ethanolic hydrochloric acid, ethanol and ammonium carbonate.

Yield: 89% of theory, $C_{25}H_{22}N_6O_3S(486,57)$; $R_f$-value: 0.16 (silica gel; dichloromethane/ethanol=4:1); Mass spectrum (EKA): $(M+H)^+=487$; $(M+Na)^+=509$.

EXAMPLE 43

1-methyl-2-[N-(4-amidinophenyl)-N-methyl-aminomethyl]-5-[N-(methoxycarbonylmethyl)-quinoline-8-sulphonylamino]-benzimidazole Prepared analogously to Example 1e from 1-methyl-2-[N-(4-cyanophenyl)-N-methyl-aminomethyl]-5-[N-(methoxycarbonylmethyl)-quinoline-8-sulphonylamino]-benzimidazole and methanolic hydrochloric acid, methanol and ammonium carbonate.

Yield: 32% of theory, $C_{29}H_{29}N_7O_4S(571.67)$; $R_f$-value: 0.28 (silica gel; dichloromethane/methanol=5:1); Mass spectrum (EKA): $(M+H)^+=572$; $(M+H+Na)^{++}=297.7$.

EXAMPLE 44

1-methyl-2-[N-(4-(N-ethoxycarbonylamidino)phenyl)-amino-methyl]-5-[N-(methoxycarbonylmethyl)-quinoline-8-sulphonylamino]-benzimidazole Prepared analogously to Example 31 from 1-methyl-2-[N-(4-amidinophenyl)-aminomethyl]-5-[N-(methoxycarbonylmethyl)-quinoline-8-sulphonylamino]-benzimidazole and ethyl chloroformate.

Yield: 71% of theory, $C_{31}H_{31}N_7O_6S(629.70)$; $R_f$-value: 0.62 (silica gel; dichloromethane/methanol=9:1); Mass spectrum (EKA): $(M+H)^+=630$; $(M+H+Na)^{++}=326.6$; $(M+2H)^{++}=315.6$.

EXAMPLE 45

1-methyl-2-[N-(-4-(N-cyclohexyloxycarbonylamidino)phenyl)-aminomethyl]-5-[N-(methoxycarbonylmethyl)-quinoline-8-sulphonylamino]-benzimidazole Prepared analogously to Example 31 from 1-methyl-2-[N-(4-amidinophenyl)-aminomethyl]-5-[N-(methoxycarbonylmethyl)-quinoline-8-sulphonylamino]-benzimidazole and cyclohexyl chloroformate.

Yield: 59% of theory, $C_{35}H_{37}N_7O_6S(683,79)$; $R_f$-value: 0.66 (silica gel; dichloromethane/methanol=9:1); Mass spectrum (EKA): $(M+H)^+=684$; $(M+H+Na)^{++}=353.7$; $(M+2H)^{++}=342.6$.

EXAMPLE 46

2-[2-(4-Amidinophenyl)-ethyl]-6-[N-(methoxycarbonylmethyl)-quinoline-8-sulphonylamino]-benzoxazole a. 2-[(4-aminocarbonylphenyl)-ethyl]-6-nitro-benzoxazole 2.64 g (15 mmol) of 4-cyanophenylpropionic acid and 2.31 g (15 mmol) of 2-amino-5-nitro-phenol are stirred in 50 ml polyphosphoric acid under a nitrogen atmosphere for three hours at 130° C. Then the mixture is poured onto water, the precipitate is suction filtered, dissolved in methylene chloride/methanol and filtered over activated charcoal. The filtrate is concentrated by evaporation in vacuo, the crystalline residue is suction filtered and dried.

Yield: 3.0 g (64% of theory), $R_f$-value: 0.43 (silica gel; dichloromethane/methanol=19:1).

b. 2-[2-(4-cyanophenyl)-ethyl]-6-nitro-benzoxazole 2.0 g (6.43 mmol) of 2-[(4-aminocarbonylphenyl)-ethyl]-6-nitro-benzoxazole are refluxed in 50 ml phosphorus oxychloride for 60 minutes. Then the mixture is distilled off in vacuo, the residue is decomposed with ice water, the crystalline product is suction filtered, washed and dried. The residue is chromatographed on silica gel (methylene chloride/ethanol=99.5:0.5). The corresponding fractions are concentrated by evaporation, triturated with ether, suction filtered and dried.

Yield: 1.25 g (66.5% of theory), $R_f$-value: 0.40 (silica gel; dichloromethane/ethanol=50:1).

c. 2-[2-(4-cyanophenyl)-ethyl]-6-amino-benzoxazole

Prepared analogously to Example 1b from 2-[2-(4-cyanophenyl)-ethyl]-6-nitro-benzoxazole and palladium on activated charcoal in methanol/methylene chloride.

Yield: 100% of theory, $R_f$-value: 0.59 (silica gel; dichloromethane/ethanol=19:1).

d. 2-[2-(4-cyanophenyl)-ethyl]-6-(N-quinoline-8-sulphonylamino)-benzoxazole

Prepared analogously to Example 1c from 2-[2-(4-cyanophenyl)-ethyl]-6-amino-benzoxazole and 8-quinolinesulphonic acid chloride in pyridine.

Yield: 57% of theory, $R_f$-value: 0.61 (silica gel; dichloromethane/ethanol=19:1).

e. 2-[2-(4-cyanophenyl)-ethyl]-6-[N-(methoxycarbonylmethyl)-quinoline-8-sulphonylamino]-benzoxazole Prepared analogously to Example 1d from 2-[2-(4-cyanophenyl)-ethyl]-6-[N-quinoline-8-sulphonylamino]-benzoxazole, methyl bromoacetate and potassium carbonate in acetone.

Yield: 88.5% of theory, $R_f$-value: 0.30 (silica gel; petroleum ether/ethylacetate=1:1).

f. 2-[2-(4-Amidinophenyl)-ethyl]-6-[N-(methoxycarbonylmethyl)-quinoline-8-sulphonylamino]-benzoxazole Prepared analogously to Example 1e from 2-[2-(4-cyanophenyl)-ethyl]-6-[N-(methoxycarbonylmethyl)-quinoline-8-sulphonylamino]-benzoxazole and hydrochloric acid/ammonium carbonate in methanol.

Yield: 82% of theory, $R_f$-value: 0.32 (silica gel; dichloromethane/ethanol=4:1); $C_{28}H_{25}N_5O_5S(543.61)$; Mass spectrum: $(M+H)^+=544$; $(M+2H)^{++}=272.7$; $(M+H+Na)^{++}=283.7$.

EXAMPLE 47

2-[2-(4-Amidinolphenyl)-ethyl]-6-[N-(hydroxycarbonylmethyl)-quinoline-8-sulphonylamino]-benzoxazole Prepared analogously to Example 3 from 2-[2-(4-amidinophenyl)-ethyl]-6-[N-(methoxycarbonylmethyl)-quinoline-8-sulphonylamino]-benzoxazole and sodium hydroxide solution.

Yield: 64% of theory, $C_{27}H_{23}N_5O_5S(529.59)$; $R_f$-value: 0.11 (silica gel; dichloromethane/methanol=4:1); Mass spectrum (EKA): $(M+H)^+=530$; $(M+Na)^+=552$; $(M+2H)^{++}=265.7$; $(M+H+Na)^{++}=276.7$; $(2M+3Na)^{3+}=376$.

EXAMPLE 48

2-[(4-Amidinophenyl)-oxymethyl]-5-[N-ethoxycarbonylmethyl)-quinoline-8-sulphonylamino]-1H-benzimidazole Prepared analogously to Example 1e from 2-[(4-cyanophenyl)-oxymethyl]-5-[N-(ethoxycarbonylmethyl)-quinoline-8-sulphonylamino]-1H-benzimidazole and ethanolic hydrochloric acid, ethanol and ammonium carbonate.

Yield: 79% of theory, $C_{28}H_{26}N_6O_5S(558.63)$; $R_f$-value: 0.26 (silica gel; dichloromethane/methanol=5:1); Mass spectrum (EKA): $(M+H)^+=559$; $(M+2H)^{++}=280$; $(M+H+Na)^{++}=291$.

EXAMPLE 49

1-methyl-2-[N-(4-amidinobenzyl)-aminomethyl]-5-[N-(ethoxycarbonylmethyl)-quinoline-8-sulphonylamino]-benzimidazole Prepared analogously to Example 1e from 1-methyl-2-[N-(4-cyanobenzyl)-aminomethyl]-5-[N-(ethoxycarbonylmethyl)-quinoline-8-sulphonylamino]-benzimidazole and ethanolic hydrochloric acid, ethanol and ammonium carbonate.

Yield: 82% of theory, $C_{30}H_{31}N_7O_4S(585.70)$; $R_f$-value: 0.30 (silica gel; dichloromethane/methanol=5:1); Mass spectrum (EKA): $(M+H)^+=586$; $(M+2H)^{++}=293.7$.

EXAMPLE 50

1-methyl-2-[N-(4-amidinobenzyl)-aminomethyl]-5-[N-(hydroxycarbonylmethyl)-quinoline-8-sulphonylamino]-benzimidazole Prepared analogously to Example 3 from 1-methyl-2-[N-(4-amidinobenzyl)-aminomethyl]-5-[N-(ethoxycarbonylmethyl)-quinoline-8-sulphonylamino]-benzimidazole and sodium hydroxide solution.

Yield: 94% of theory, $C_{28}H_{27}N_7O_4S(557.64)$; Mass spectrum (EKA): $(M+H)^+=558$; $(M+Na)^+=580$.

EXAMPLE 51

2-[2-(4-Amidinophenyl)-ethyl]-5-[N-(ethoxycarbonylmethyl)-quinoline-8-sulphonylamino]-benzoxazole a. 2-[2-(4-cyanophenyl)-ethyl]-5-nitro-benzoxazole Prepared analogously to Example 46b from 2-[(4-aminocarbonylphenyl)-ethyl]-5-nitro-benzoxazole and phosphorus oxychloride.

Yield: 36% of theory, $R_f$-value: 0.90 (silica gel; dichloromethane/methanol=19:1).

b. 2-[2-(4-cyanophenyl)-ethyl]-5-amino-benzoxazole

Prepared analogously to Example 1b from 2-[2-(4-cyanophenyl)-ethyl]-5-nitro-benzoxazole and palladium on activated charcoal in methanol/methylene chloride.

Yield: 100% of theory, $R_f$-value: 0.36 (silica gel; dichloromethane/methanol=19:1).

c. 2-[2-(4-cyanophenyl)-ethyl]-5-(-quinoline-8-sulphonylamino)-benzoxazole

Prepared analogously to Example 1c from 2-[2-(4-cyanophenyl)-ethyl]-5-amino-benzoxazole and 8-quinolinesulphonic acid chloride in pyridine.

Yield: 27% of theory, $R_f$-value: 0.70 (silica gel; dichloromethane/methanol=19:1).

d. 2-[2-(4-cyanophenyl)-ethyl]-5-[N-(ethoxycarbonylmethyl)-quinoline-8-sulphonylamino]-benzoxazole Prepared analogously to Example 1d from 2-[2-(4-cyanophenyl)-ethyl]-5-(N-quinoline-8-sulphonylamino)-benzoxazole, bromoethyl acetate and potassium carbonate in acetone.

Yield: 100% of theory, $R_f$-value: 0.78 (silica gel; dichloromethane/methanol=50:1).

e. 2-[2-(4-Amidinophenyl)-ethyl-]5-[N-(ethoxycarbonylmethyl)-quinoline-8-sulphonylamino]-benzoxazole Prepared analogously to Example 1e from 2-[2-(4-cyanophenyl)-ethyl]-5-[N-(ethoxycarbonylmethyl)-quinoline-8-sulphonylamino]-benzoxazole and hydrochloric acid/ammonium carbonate in ethanol.

Yield: 98% of theory, $R_f$-value: 0.44 (silica gel; dichloromethane/methanol=5:1); $C_{29}H_{27}N_5O_5S$(557.63); Mass spectrum: $(M+H)^+=558$; $(M+2H)^{++}=279.7$; $(M+H+Na)^{++}=290.7$.

EXAMPLE 52

2-[2-(4-Amidinophenyl)-ethyl]-5-[N-(hydroxycarbonylmethyl)-quinoline-8-sulphonylamino]-benzoxazole Prepared analogously to Example 3 from 2-[2-(4-amidinophenyl)-ethyl]-5-[N-(ethoxycarbonylmethyl)-quinoline-8-sulphonylamino]-benzoxazole and sodium hydroxide solution.

Yield: 77% of theory, $C_{27}H_{23}N_5O_5S$(529.58); Mass spectrum (EKA): $(M+H)^+=530$; $(M+Na)^+=552$; $(M+H+Na)^{++}=276.6$; $(M-H+2Na)^+=574$; $(M+2Na)^{++}=287.6$.

EXAMPLE 53

1-methyl-2-[2-(2-amidinothiophen-5-yl)-ethyl]-5-[N-(ethoxycarbonylmethyl)-quinoline-8-sulphonylamino]-benzimidazole Prepared analogously to Example 1e from 1-methyl-2-[2-(2-cyanothiophen-5-yl)-ethyl]-5-[N-(ethoxycarbonylmethyl)-quinoline-8-sulphonylamino]-benzimidazole and ethanolic hydrochloric acid, ethanol and ammonium carbonate.

Yield: 42% of theory, $C_{28}H_{28}N_6O_4S_2$(576.71); $R_f$-value: 0.36 (silica gel; dichloromethane/methanol=5:1); Mass spectrum (EKA): $(M+H)^+=577$; $(M+2H)^{++}=289$; $(M+H+Na)++=300$.

EXAMPLE 54

1-methyl-2-[2-(2-amidinothiophen-5-yl)-ethyl]-5-[N-(hydroxycarbonylmethyl)-quinoline-8-sulphonylamino]-benzimidazole Prepared analogously to Example 3 from 1-methyl-2-[2-(2-amidinothiophen-5-yl)-ethyl]-5-[N-(ethoxycarbonylmethyl)-quinoline-8-sulphonylamino]-benzimidazole and sodium hydroxide solution.

Yield: 98% of theory, $C_{26}H_{24}N_6O_4S_2$(548.66); Mass spectrum (EKA): $(M+H)^+=549$; $(M+Na)^+=571$.

EXAMPLE 55

1-methyl-2-[N-(4-amidinophenyl)-aminomethyl]-5-[N-(ethoxycarbonylmethyl)-benzenesulphonylamino]-benzimidazole Prepared analogously to Example 1e from 1-methyl-2-[N-(4-cyanophenyl)-aminomethyl]-5-[N-(ethoxycarbonylmethyl)-benzenesulphonylamino]-benzimidazole and ethanolic hydrochloric acid, ethanol and ammonium carbonate.

Yield: 50% of theory, $C_{26}H_{28}N_6O_4S$(520.62); $R_f$-value: 0.34 (silica gel; dichloromethane/methanol=5:1); Mass spectrum (EKA): $(M+H)^+=521$.

EXAMPLE 56

1-methyl-2-[N-(4-amidinophenyl)-aminomethyl]-5-[N-(hydroxycarbonylmethyl)-benzenesulphonylamino]-benzimidazole Prepared analogously to Example 3 from 1-methyl-2-[N-(4-amidinophenyl)-aminomethyl]-5-[N-(ethoxycarbonylmethyl)-benzenesulphonylamino]-benzimidazole and sodium hydroxide solution.

Yield: 97% of theory, $C_{24}H_{24}N_6O_4S$(492.56); Mass spectrum (EKA): $(M+H)^+=493$; $(M+Na)^+=515$; $(M-H+2Na)^+=537$; $(M+2Na)^{++}=269$.

EXAMPLE 57

1-methyl-2-[-(4-amidinophenyl)-aminomethyl]-5-(N-benzyl-N-methylamino)-benzimidazole Prepared analogously to Example 1e from 1-methyl-2-[N-(4-cyanophenyl)-aminomethyl]-5-(N-benzyl-N-methylamino)-benzimidazole and ethanolic hydrochloric acid, ethanol and ammonium carbonate.

Yield: 85% of theory, $C_{24}H_{26}N_6$(398.51); $R_f$-value: 0.27 (silica gel; dichloromethane/methanol=4:1); Mass spectrum (EKA): $(M+H)^+=399$; $(M+2H)^{++}=200$.

EXAMPLE 58

1-methyl-2-[N-(4-amidinophenyl)-aminomethyl]-5-[N-(ethoxycarbonylmethyl)-n-butanesulphonylamino]-benzimidazole Prepared analogously to Example 1e from 1-methyl-2-[N-(4-cyanophenyl)-aminomethyl]-5-[N-(ethoxycarbonylmethyl)-n-butanesulphonylamino]-benzimidazole and ethanolic hydrochloric acid, ethanol and ammonium carbonate.

Yield: 71% of theory, $C_{24}H_{32}N_6O_4S$(500.63); $R_f$-value: 0.32 (silica gel; dichloromethane/methanol=5:1); Mass spectrum (EKA): $(M+H)^+=501$; $(M+H+Na)^{++}=262$.

EXAMPLE 59

1-methyl-2-[N-(4-amidinophenyl)-aminomethyl]-5-[N-(ethoxycarbonylmethyl)-benzoylamino]-benzimidazole Prepared analogously to Example 1e from 1-methyl-2-[N-(4-cyanophenyl)-aminomethyl]-5-[N-(ethoxycarbonylmethyl)-benzoylamino]-benzimidazole and ethanolic hydrochloric acid, ethanol and ammonium carbonate.

Yield: 56% of theory, $C_{27}H_{28}N_6O_3$(484.57); $R_f$-value: 0.34 (silica gel; dichloromethane/methanol=5:1); Mass spectrum (EKA): $(M+H)^+=485$; $(M+H+Na)^{++}=254$.

EXAMPLE 60

1-methyl-2-[N-(4-amidinophenyl)-aminomethyl]-5-[N-(ethoxycarbonylmethyl)-pyridin-2-yl-carbonylamino]-benzimidazole Prepared analogously to Example 1e from 1-methyl-2-[N-(4-cyanophenyl)-aminomethyl]-5-[N-

(ethoxycarbonylmethyl)-pyridin-2-yl-carbonylamino]-benzimidazole and ethanolic hydrochloric acid, ethanol and ammonium carbonate.

Yield: 64% of theory, $C_{26}H_{27}N_7O_3$(485.56); $R_f$-value: 0.31 (silica gel; dichloromethane/methanol=5:1); Mass spectrum (EKA): $(M+H)^+$=486; $(M+H+Na)^{++}$=254.7.

EXAMPLE 61

1-methyl-2-[N-(4-amidinophenyl)-aminomethyl]-5-[N-(hydroxycarbonylmethyl)-n-butanesulphonylamino]-benzimidazole Prepared analogously to Example 3 from 1-methyl-2-[N-(4-amidinophenyl)-aminomethyl]-5-[N-(ethoxycarbonylmethyl)-n-butanesulphonylamino]-benzimidazole and sodium hydroxide solution.

Yield: 98% of theory, $C_{22}H_{28}N_6O_4S$(472.57); Mass spectrum (EKA): $(M+H)^+$=473; $(M+Na)^+$=495; $(M+2Na)^{++}$=259.

EXAMPLE 62

1-methyl-2-[N-(4-amidinophenyl)-aminomethyl]-5-[N-(hydroxycarbonylmethyl)-benzoylamino]-benzimidazole Prepared analogously to Example 3 from 1-methyl-2-[N-(4-amidinophenyl)-aminomethyl]-5-[N-(ethoxycarbonylmethyl)-benzoylamino]-benzimidazole and sodium hydroxide solution.

Yield: 69% of theory, $C_{25}H_{24}N_6O_3$(456.51); Mass spectrum (EKA): $(M+H)^+$=457; $(M+2Na)^{++}$=251; $(M+Na)^+$=479.

EXAMPLE 63

1-methyl-2-[N-(4-amidinophenyl-)aminomethyl]-5-[N-(hydroxycarbonylmethyl)-pyridin-2-yl-carbonylamino]-benzimidazole Prepared analogously to Example 3 from 1-methyl-2-[N-(4-amidinophenyl)-aminomethyl]-5-[N-(ethoxycarbonylmethyl)-pyridin-2-yl-carbonylamino]-benzimidazole and sodium hydroxide solution.

Yield: 96% of theory, $C_{24}H_{23}N_7O_3$(457.50); Mass spectrum (EKA): $(M+H)^+$=458; $(M+Na)^+$=480; $(M+H+Na)^{++}$=240.6; $(M+2Na)^{++}$=251.6.

EXAMPLE 64

1-methyl-2-[(4-amidinophenyl)-oxymethy]-5-(N-cyclohexyl-methanesulphonylamimo)-benzimidazole Prepared analogously to Example 1e from 1-methyl-2-[(4-cyanophenyl)-oxymethyl]-5-(N-cyclohexyl-methanesulphonylamino)-benzimidazole and ethanolic hydrochloric acid, ethanol and ammonium carbonate.

Yield: 79% of theory, $C_{23}H_{29}N_5O_3S$(455.59); $R_f$-value: 0.21 (silica gel; dichloromethane/ethanol=4:1); Mass spectrum (EKA): $(M+H)^+$=456; $(M+Na)^+$=478.

EXAMPLE 65

1-methyl-2-[(4-amidinophenyl)-oxymethyl]-6-[N-(ethoxycarbonylmethyl-benzenesulphonylamino]-benzimidazole Prepared analogously to Example 1e from 1-methyl-2-[(4-cyanophenyl)-oxymethyl]-6-[N-(ethoxycarbonylmethyl)-benzenesulphonylamino]-benzimidazole and ethanolic hydrochloric acid, ethanol and ammonium carbonate.

Yield: 45% of theory, $C_{26}H_{27}N_5O_5S$(521.6); Mass spectrum (EKA): $(M+H)^+$=522; $(M+H+Na)^{++}$=272.7.

EXAMPLE 66

1-methyl-2-[N-(4-amidinophenyl)-aminomethyl]-5-(N-cyclopentyl-methanesulphonylamino)-benzimidazole Prepared analogously to Example 1e from 1-methyl-2-[N-(4-cyanophenyl)-aminomethyl]-5-(N-cyclopentyl-methanesulphonylamino)-benzimidazole and ethanolic hydrochloric acid, ethanol and ammonium carbonate.

Yield: 89% of theory, $C_{22}H_{28}N_6O_2S$(440.58); $R_f$-value: 0.17 (silica gel; dichloromethane/ethanol=4:1); Mass spectrum (EKA): $(M+H)^+$=441; $(M+Na)^+$=463.

EXAMPLE 67

1-methyl-2-[(4-amidinophenyl)-oxymethyl]-5-[N-(N'-(ethoxycarbonylmethyl)-aminocarbonylmethyl)-quinoline-8-sulphonylamino]-benzimidazole Prepared analogously to Example 1e from 1-methyl-2-[(4-cyanophenyl)-oxymethyl]-5-[(N'-(ethoxycarbonylmethyl)-aminocarbonylmethyl)-quinoline-8-sulphonylamino]-benzimidazole and ethanolic hydrochloric acid, ethanol and ammonium carbonate.

Yield: 49% of theory, $C_{31}H_{31}N_7O_6S$(629.7); Mass spectrum (EKA): $(M+H)^+$=630; $(M+2H)^{++}$=315.7; $(M+H+Na)^{++}$=326.7.

EXAMPLE 68

1-methyl-2-[(4-amidinophenyl)-oxymethyl]-5-[N-(N'-(hydroxycarbonylmethyl)-aminocarbonylmethyl)-quinoline-8-sulphonylamino]-benzimidazole Prepared analogously to Example 3 from 1-methyl-2-[(4-amidinophenyl)-oxymethyl]-5-[N-(N'-(ethoxycarbonylmethyl)-aminocarbonylmethyl)-quinoline-8-sulphonylamino]-benzimidazole and sodium hydroxide solution.

Yield: 79% of theory, $C_{29}H_{27}N_7O_6S$(601.7); Mass spectrum (EKA): $(M+H)^+$=602; $(M+Na)^+$=624; $(M+2H)^{++}$=301.7; $(M+H+Na)^{++}$=312.7.

EXAMPLE 69

1-methyl-2-[(4-amidinophenyl)-oxymethyl]-5-[N-(2-ethoxycarbonylethyl)-quinoline-8-sulphonylamino]-benzimidazole Prepared analogously to Example 1e from 1-methyl-2-[(4-cyanophenyl)-oxymethyl]-5-[N-(2-ethoxycarbonylethyl)-quinoline-8-sulphonylamino]-benzimidazole and ethanolic hydrochloric acid, ethanol and ammonium carbonate.

Yield: 62% of theory, $C_{30}H_{30}N_6O_5S$(586.7); Mass spectrum (EKA): $(M+H)^+$=587; $(M+2H)^{++}$=294; $(M+H+Na)^{++}$=305.

EXAMPLE 70

2-[N-(4-Amidinophenyl)-aminomethyl]-3-methyl-6-[N-(ethoxycarbonylmethyl)-1,2,3,4-tetrahydro-quinoline-8-sulphonylamino]-benzofuran Prepared analogously to Example 1e from 2-[N-(4-cyanophenyl)-aminomethyl]-3-methyl-6-[N-

(ethoxycarbonylmethyl)-1,2,3,4-tetrahydro-quinoline-8-sulphonylamino]-benzofuran (prepared analogously to Example 107) and ethanolic hydrochloric acid, ethanol and ammonium carbonate.

Yield: 55% of theory, $C_{30}H_{33}N_5O_5S(575.70)$; $R_f$-value: 0.25 (silica gel; dichloromethane/ethanol=4:1); Mass spectrum (EKA): $(M+H)^+=576$; $(M+H+Na)^{++}=299.7$.

EXAMPLE 71

2-[N-(4-Amidinophenyl)-aminomethyl]-3-methyl-6-[N-(hydroxycarbonylmethyl)-1,2,3,4-tetrahydro-quinoline-8-sulphonylamino]-benzofuran Prepared analogously to Example 3 from 2-[N-(4-amidinophenyl)-aminomethyl]-3-methyl-6-[N-(ethoxycarbonylmethyl)-1,2,3,4-tetrahydro-quinoline-8-sulphonylamino]-benzofuran and sodium hydroxide solution.

Yield: 94% of theory, $C_{28}H_{29}N_5O_5S(547.65)$; Mass spectrum (EKA): $(M+H)^+=548$; $(M+Na)^+=570$; $(M+2Na)^{++}=296.7$.

EXAMPLE 72

2-[2-(4-Amidinophenyl)-ethyl]-4-methyl-7-[N-(ethoxycarbonylmethyl)-quinoline-8-sulphonylamino]-quinoline Prepared analogously to Example 1e from 2-[2-(4-cyanophenyl)-ethyl]-4-methyl-7-[N-(ethoxycarbonylmethyl)-quinoline-8-sulphonylamino]-quinoline (prepared analogously to Example 102) and ethanolic hydrochloric acid, ethanol and ammonium carbonate.

Yield: 50% of theory, $C_{32}H_{31}N_5O_4S(581.6)$; $R_f$-value: 0.18 (silica gel; dichloromethane/ethanol=4:1); Mass spectrum (EKA): $(M+H)^+=582$; $(M+2H)^{++}=291.7$; $(M+H+Na)^{++}=302.7$.

EXAMPLE 73

2-[2-(4-Amidinophenyl)-ethyl]-4-methyl-7-[N-(hydroxycarbonylmethyl)-quinoline-8-sulphonylamino]-quinoline Prepared analogously to Example 3 from 2-[2-(4-amidinophenyl)-ethyl]-4-methyl-7-[N-(ethoxycarbonylmethyl)-quinoline-8-sul-phonylamino]-quinoline and sodium hydroxide solution.

Yield: 38% of theory, $C_{30}H_{27}N_5O_4S(553.60)$; Mass spectrum (EKA): $(M+H)^+=554$; $(M+Na)^+=576$; $(M+2H)^{++}=277.7$.

EXAMPLE 74

1-methyl-2-[2-(4-amidinophenyl)-ethyl]-5-(N-quinoline-8-sulphonylamino)-indole-hydrochloride a. (E)-4-[2-(1-methyl-indol-2-yl)ethenyl]benzonitrile 3.25 g (about 67 mmol) of a 50% sodium hydride suspension in mineral oil is heated to 80° C. in 70 ml dimethylsulphoxide for 45 minutes. After cooling to ambient temperature a further 140 ml of dimethylsulphoxide were added and 18.2 g (44 mmol) of 4-cyanobenzyl-triphenylphosphonium bromide were added batchwise and the resulting mixture was stirred for 90 minutes at ambient temperature. Then 7.0 g (44 mmol) of 1-methyl-indol-2-yl-carbaldehyde (J. Org. Chem. 52, 104 (1987)) in 70 ml dimethylsulphoxide were added dropwise and stirred for 30 minutes at ambient temperature, 20 minutes at 40° C. and 16 hours again at ambient temperature. The crude product is diluted with 200 ml ethyl acetate, washed with 400 ml of 14% sodium chloride solution and the aqueous phase is extracted with 2×300 ml ethyl acetate. The combined organic phases are dried with sodium sulphate, the solvent is distilled off in vacuo, and the crude product is purified by flash chromatography (silica gel, petroleum ether/ethyl acetate=9:1).

Yield: 2.4 g (21% of theory), $R_f$-value: 0.52 (silica gel; ethyl acetate/petroleum ether=3:7).

b. 4-[2-(1-methyl-indol-2-yl)ethyl]benzonitrile 2.3 g (8.9 mmol) of (E)-4-[2-(1-methyl-indol-2-yl)ethenyl]benzonitrile are dissolved in 150 ml methanol and 50 ml methylene chloride and hydrogenated with 0.20 g 10% palladium on charcoal at 3 bar hydrogen pressure. The solvent is distilled off in vacuo, the white residue obtained is washed with a little diethylether and acetone.

Yield: 1.8 g (78% of theory), $R_f$-value: 0.50 (silica gel; ethyl acetate/petroleum ether=3:7).

c. 4-[2-(1-methyl-5-nitro-indol-2-yl)ethyl]benzonitrile

Within 2 hours 1.7 g (6.53 mmol) of 4-[2-(1-methyl-indol-2-yl)ethyl]benzonitrile is dissolved in 20 ml conc. sulphuric acid at 15° C. and then cooled to 2° C. Then 0.66 g (6.53 mmol) of potassium nitrate are added batchwise (temperature rise to about 10° C.). The mixture is stirred for a further 30 minutes at 2–5° C. and then poured onto ice. The yellowish precipitate formed is filtered off and washed with water.

Yield: 2.0 g (100% of theory), $R_f$-value: 0.24 (silica gel; ethyl acetate/petroleum ether=3:7).

d. 4-[2-(1-methyl-5-amino-indol-2-yl)ethyl]benzonitrile 2.0 g (6.55 mmol) of 4-[2-(1-methyl-5-nitro-indol-2-yl)ethyl]benzonitrile are dissolved in 200 ml methanol and 200 ml methylene chloride and hydrogenated with 0.20 g of 10% palladium on charcoal at 3 bar hydrogen pressure. Then the solvent is distilled off in vacuo, and the residue is washed with a little methanol.

Yield: 1.67 g (93% of theory) yellowish-beige amorphous solid, $R_f$-value: 0.38 (silica gel; methylene chloride/ethanol=19:1).

e. 1-methyl-2-[2-(4-cyanophenyl)-ethyl]-5-(N-quinoline-8-sulphonylamino)

A solution of 1.57 g (5.7 mmol) of 4-[2-(1-methyl-5-amino-in-dol-2-yl)-ethyl]benzonitrile and 1.42 g (6.2 mmol) of quinoline-8-sulphonic acid chloride in 30 ml pyridine is stirred for 1 hour at ambient temperature. Then the solvent is eliminated in vacuo, the residue is taken up in 50 ml methylene chloride, washed with 50 ml of saturated sodium hydrogen carbonate solution, dried with sodium sulphate and purified by flash chromatography (silica gel, methylene chloride/ethanol=99:1).

Yield: 0.77 g (49% of theory), $R_f$-value: 0.39 (silica gel; methylene chloride/ethanol=50:1).

f. 1-methyl-2-[2-(-4-amidinolphenyl)ethyl]-5-(N-quinoline-8-sulphonylamino)-indole-hydrochloride Prepared analogously to Example 1e from 1-methyl-2-[2-(4-cyanophenyl)ethyl]-5-(N-quinoline-8-sulphonylamino)-indole and ethanolic hydrochloric acid, ethanol and ammonium carbonate.

Yield: 39% of theory, $C_{27}H_{25}N_5O_2S(483.6)$; Rf-value: 0.29 (silica gel; methylene chloride/ethanol=4:1+a few drops of acetic acid); Mass spectrum (SKA): $(M+H)^+=484$.

EXAMPLE 75

1-methyl-2-[2-(4-amidinophenyl)-ethyl]-5-[N-(ethoxycarbonylmethyl)-quinoline-8-sulphonylamino]-indole Prepared analogously to Example 1e from 1-methyl-2-[2-(4-cyanophenyl)-ethyl]-5-[N-(ethoxycarbonylmethyl)- quinoline-8-sulphonylamino]-indole and ethanolic hydrochloric acid, ethanol and ammonium carbonate.

Yield: 53% of theory, $C_{31}H_{31}N_5O_4S$(569.69); $R_f$-value: 0.19 (silica gel; dichloromethane/ethanol 4:1); Mass spectrum (EKA): (M+H)+570; (M+2H)$^{++}$=285.7; (M+H+Na)++=.296.6.

EXAMPLE 76

1-methyl-2-[2-(4-amidinophenyl)-ethyl]-5-[N-(hydroxycarbonylmethyl)-quinoline-8-sulphonylamino]-indole Prepared analogously to Example 3 from 1-methyl-2-[2-(4-amidinophenyl)-ethyl]-5-[N-(ethoxycarbonylmethyl)-quinoline-8-sul-phonylamino]-indole and sodium hydroxide solution.

Yield: 96% of theory, $C_{29}H_{27}N_5O_4S$(541.63); Mass spectrum (EKA): (M+H)$^+$=542; (M+Na)$^+$=564; (M+2H)$^{++}$=271.7; (M−H)$^−$=540.

EXAMPLE 77

1-methyl-2-(4-amidinobenzylamino)-5-(quinoline-8-sulphonylamino)-benzimidazole

Prepared analogously to Example 1e from 1-methyl-2-(4-cyanobenzylamino)-5-(quinoline-8-sulphonylamino)-benzimidazole and ethanolic hydrochloric acid, ethanol and ammonium carbonate.

Yield: 85% of theory, $C_{25}H_{23}N_7O_2S$(485,57); $R_f$-value: 0.40 (silica gel; ethyl acetate/ethanol/ammonia=50:45:5); Mass spectrum (EKA): (M+H)$^+$=486; (M+H+Na)$^{++}$=254,7.

EXAMPLE 78

1-methyl-2-(4-amidinobenzylthio)-5-(quinoline-8-sulphonylamino)-benzimidazole

Prepared analogously to Example 1e from 1-methyl-2-(4-cyanobenzylthio)-5-(quinoline-8-sulphonylamino)-benzimidazole and ethanolic hydrochloric acid, ethanol and ammonium carbonate.

Yield: 69% of theory, $C_{25}H_{22}N_6O_2S_2$(502.62); $R_f$-value: 0.45 (silica gel; ethyl acetate/ethanol/ammonia=50:45:5); Mass spectrum (EKA): (M+H)$^+$=503; (M+Na)$^+$=525.

EXAMPLE 79

2-[(4-Amidinophenyl)methylthio]-5-(N-quinoline-8-sulphonylamino)-benzothiazole-hydrochloride a. 2-[(4-cyanophenyl)methylthio]-6-nitro-benzothiazole 0.37 g (7.7 mmol) of sodium hydride (50% in mineral oil) is added batchwise to a solution of 1.5 g (7.06 mmol) of 2-mercapto-6-nitro-benzothiazole and then stirred for 30 minutes at 50° C. Then 1.45 g (7.4 mmol) of 4-bromomethylbenzonitrile is added dropwise and stirred for a further hour at 50° C. The re-action mixture is mixed with 30 ml of ethyl acetate and 70 ml of 14% sodium chloride solution, whereupon a large proportion of the title compound is obtained as a beige precipitate. The organic phase is concentrated in vacuo, the crude product precipitated is triturated with diethyl ether and the liquid phase is separated off. The solid obtained is combined with the beige precipitate.

Yield: 1.3 g (56% of theory), $R_f$-value: 0.52 (silica gel; ethyl acetate/petroleum ether=3:7).

b. 2-[(4-cyanophenyl)methylthio]-6-amino-benzothiazole

A suspension of 1.0 g (3.05 mmol) of 2-[(4-cyanophenyl)methylthio]-6-nitro-benzothiazole is heated to boiling in 60 ml glacial acetic acid until a clear solution is formed. Then 2.0 g (36 mmol) of iron powder is added in two batches and the resulting mixture is refluxed for 5 minutes. It is filtered, and the filtrate is concentrated in vacuo. The crude product is made alkaline by the addition of conc. ammonia and purified by flash chromatography (silica gel, ethyl acetate/petroleum ether=20:80 to 35:65).

Yield: 0.22 g (24% of theory) beige-coloured amorphous solid, $R_f$-value: 0.44 (silica gel; ethyl acetate/petroleum ether=4:6).

c. 2-[(4-cyanophenyl)methylthio]-6-(N-quinoline-8-sulphonylamino)-benzothiazole

A mixture of 2.3 g (7.74 mmol) of 2-[(4-cyanophenyl)methylthio]-6-amino-benzothiazole and 1.85 g (8.1 mmol) of quinoline-8-sulphonic acid chloride is stirred in 30 ml of pyridine for 2 hours at ambient temperature. Then the solvent is distilled off in vacuo and the crude product is purified by flash chromatography (silica gel, methylene chloride/ethanol=99:1).

Yield: 3.15 g (83% of theory), Melting point: 106–108° C.; $R_f$-value: 0.33 (silica gel; ethyl acetate/petroleum ether=4:6).

d. 2-[(4-Amidinophenyl)methylthio]-6-(N-quinoline-8-sulphonylamino)-benzothiazole-hydrochloride Prepared analogously to Example 1e from 2-[(4-cyanophenyl)methylthio]-6-(N-quinoline-8-sulphonylamino)-benzothiazole and ethanolic hydrochloric acid, ethanol and ammonium carbonate.

Yield: 91% of theory, $C_{24}H_{19}N_5O_2S_3$(505.64); $R_f$-value: 0.34 (silica gel; methylene chloride/ethanol=4:1+a few drops of acetic acid); Mass spectrum (SKA): (M+H)$^+$=506.

EXAMPLE 80

Mixture of 2-[2-(4-amidinophenyl)-ethyl]-1-methyl-6-(quinoline-8-sulphonylamino)-imidazo[4,5-b]pyridine-hydrochloride and 2-[2-(4-amidinophenyl)-ethyl]-3-methyl- 6-(quinoline-8-sulphonylamino)-imidazo[4,5-b]pyridine-hydrochloride a. 3-(4-cyanophenyl)-N-(3,5-dinitro-pyrid-2-yl)-propionic acid amide A solution of 1.8 g (10 mmol) of 2-amino-3,5-dinitro-pyridine, 2.4 g (12 mmol) of 3-(4-cyanophenyl)propionyl chloride, 2.0 ml triethylamine and 0.1 g dimethylamine in 35 ml chlorobenzene is heated to 150° C. for 3 hours. Then the solvent is distilled off in vacuo, and the residue is taken up in 50 ml of ethyl acetate. It is washed with 50 ml of water and 50 ml of saturated sodium chloride solution, dried with sodium sulphate, and after the solvent has been distilled off the residue is purified by flash chromatography (silica gel, methylene chloride).

Yield: 2.2 g (65% of theory), $R_f$-value: 0.67 (silica gel; methylethylketone/xylene=1:1).

b) 2-[2-(4-cyanophenyl)ethyl]-6-phthalimido-imidazo[4.5-b]pyridine

A suspension of 2.1 g (6.15 mmol) of 3-(4-cyanophenyl)-N-(3,5-dinitro-pyrid-2-yl)-propionic acid amide and 0.50 g of 10% palladium on charcoal in 50 ml glacial acetic acid is reacted at 80° C. at 3 bar hydrogen pressure. After cooling the catalyst is filtered off, 1.1 g (7.4 mmol) of phthalic anhydride is added and heated to boiling for 1 hour. The solvent is distilled off in vacuo, and the crude product is taken up in 50 ml of methylene chloride, washed twice with saturated sodium hydrogen carbonate solution and purified by flash chromatography (silica gel; methylene chloride/ethanol=40:1 to 19:1).

Yield: 0.95 g (41% of theory), $R_f$-value: 0.50 (silica gel; ethyl acetate/ethanol/ammonia=90:10:1).

c. Isomer mixture of 2-[2-(4-cyanophenyl)-ethyl]-1-methyl-6-phthalimido-imidazo[4,5-b]pyridine and 2-[2-(4-cyanophenyl)-ethyl]-3-methyl-6-phthalimido-imidazo[4,5-b]pyridine A mixture of 0.80 g (2.0 mmol) of 2-[2-(4-cyanophenyl)-ethyl]-6-phthalimido-imidazo[4,5-b]pyridine, 0.25 g (2.2 mmol) of potassium-tert.butoxide and 0.32 g (2.2 mmol) of methyliodide is stirred in 10 ml of dimethylsulphoxide for 1 hour at ambient temperature. Then the mixture is poured onto ice water, extracted with 100 ml of ethyl acetate, dried with sodium sulphate, and the solvent is distilled off in vacuo.

Yield: 0.80 g (98% of theory), $R_f$-value: 0.56 (silica gel; ethyl acetate/ethanol/ammonia=90:10:1).

d. Isomer mixture of 2-[2-(4-cyanophenyl)-ethyl]-1-methyl-6-imidazo[4,5-b]pyridine and 2-[2-(4-cyanophenyl)-ethyl]-3-methyl-6-imidazo[4,5-b]pyridine 0.80 g (2.0 mmol) of the isomer mixture of 2-[2-(4-cyanophenyl)-ethyl]-1-methyl-6-phthalimido-imidazo[4,5-b]pyridine and 2-[2-(4-cyanophenyl)-ethyl]-3-methyl-6-phthalimido-imidazo[4,5-b]pyridine are stirred into 5 ml of 40% aqueous methylamine solution and 20 ml of ethanol for 1 hour at 40–60° C. Then the solvent is distilled off in vacuo, the crude product is taken up in 40 ml of ethyl acetate/ethanol (9:1) and washed successively with water and saturated sodium chloride solution. After elimination of the solvent in vacuo the residue is taken up in pyridine and reacted analogously to Example 79c with 0.41 g (1.8 mmol) of quinoline-8-sulphonic acid chloride, worked up and purified by flash chromatography (silica gel, methylene chloride to methylene chloride/ethanol=19:1).

Yield: 0.50 g (54% of theory), $R_f$-value: 0.63+0.50 (silica gel; ethyl acetate/ethanol/ammonia=90:10:1).

e. Isomer mixture of 2-[2-(4-amidinophenyl)-ethyl]-1-methyl-6-(quinoline-8-sulphonylamino)-imidazo[4,5-b]pyridine-hydrochloride and 2-[2-(4-amidinophenyl)-ethyl]-3-methyl-6-(quinoline-8-sulphonylamino)-imidazo[4,5-b]pyridine-hydrochloride Prepared analogously to Example 1e from the isomer mixture of 2-[2-(4-cyanophenyl)-ethyl]-1-methyl-6-(quinoline-8-sulphonylamino)-imidazo[4,5-b]pyridine and 2-[2-(4-cyanophenyl)-ethyl]-3-methyl-6-(quinoline-8-sulphonylamino)-imidazo[4,5-b]pyridine and methanolic hydrochloric acid, methanol and ammonium carbonate.

Yield: 80% of theory, $C_{25}H_{23}N_7O_2S$(485.57); $R_f$-value: 0.25+0.21 (silica gel; ethyl acetate/ethanol/ammonia=50:45:5); Mass spectrum (SKA): $(M+H)^+$=486.

EXAMPLE 81

2-(4-Amidinobenylthio)-6-[N-(methoxycarbonylmethyl)-quinoline-8-sulphonylamino]-benzothiazole Prepared analogously to Example 1e from 2-(4-cyanobenzylthio)-6-[N-(methoxycarbonylmethyl)-quinoline-8-sulphonylamino]-benzothiazole and ethanolic hydrochloric acid, ethanol and ammonium carbonate.

Yield: 28% of theory, $C_{27}H_{23}N_5O_4S_3$(577.41); $R_f$-value: 0.21 (silica gel; dichloromethane/ethanol=4:1); Mass spectrum (EKA): $(M+H)^+$=578; $(M+H+Na)^{++}$=300.7.

EXAMPLE 82

2-[(4-Amidinophenyl)oxmethyl]-5-[N-(methoxycarbonylmethyl)-quinoline-8-sulphonylamino]-benzothiazole-hydrochloride a. (4-cyanophenyl)oxy-N-(5-nitro-2-mercaptophenyl)-acetic acid amide A solution of 1.05 g (6.5 mmol) of carbonyldiimidazolide and 1.15 g (6.5 mmol) of (4-cyanophenyl)oxyacetic acid in 10 ml of tetrahydrofuran is heated for 30 minutes to 50° C. Then 1.0 g (5.9 mmol) of 2-mercapto-5-nitroaniline are added and the mixture is heated for a further 3 hours to 50° C. The mixture is filtered, the filtrate is concentrated in vacuo and the crude product is purified by flash chromatography (silica gel, methylene chloride/ethanol=19:1 to 4:1).

Yield: 1.05 g (54% of theory), Melting point: 274–276° C.; $R_f$-value: 0.54 (silica gel; methylene chloride/ethanol= 19:1+a few drops of conc. ammonia).

b. 2-[(4-cyanophenyl)oxymethyl]-5-nitrobenzothiazole

A solution of 2.1 g (6.4 mmol) of (4-cyanophenyl)oxy-N-(5-nitro-2-mercaptophenyl)-acetic acid amide in 20 ml of glacial acetic acid is heated to 80° C. for 1 hour, diluted with ice water and the crude product precipitated is filtered off. After flash chromatography (silica gel, methylene chloride:ethanol=99:1) a beige amorphous solid is obtained.

Yield: 0.77 g (37% of theory), $R_f$-value: 0.56 (silica gel; methylene chloride/ethanol=50:1).

c. 2-[(4-cyanophenyl)oxymethyl]-5-amino-benzothiazole

A solution of 0.62 g (2.0 mmol) of 2-[(4-cyanophenyl)oxymethyl]-5-nitro-benzothiazole in 20 ml of pyridine is mixed successively with 1.0 g (5.7 mmol) of sodium dithionite and 4 ml of water and stirred for 2 hours at 95° C. Then the solvent is distilled off in vacuo and the residue is diluted with ice water. It is filtered and the filter residue is washed several times with a little cold water.

Yield: 0.44 g (79% of theory), $R_f$-value: 0.37 (silica gel; methylene chloride/ethanol=50:1).

d. 2-[(4-cyanophenyl)oxymethyl]-5-(quinoline-8-sulphonylamino)-benzothiazole

Prepared analogously to Example 79c from 0.40 g (1.42 mmol) of 2-[(4-cyanophenyl)oxymethyl]-5-amino-benzothiazole and 0.34 g (1.5 mmol) of quinoline-8-sulphonic acid chloride. Further purification was carried out by flash chromatography (silica gel, methylene chloride/ethanol=99:1).

Yield: 0.41 g (61% of theory), $R_f$-value: 0.49 (silica gel; methylene chloride/ethanol=50:1).

e. 2-[(4-cyanophenyl)oxymethyl]-5-[N-[ethoxycarbonylmethyl)-quinoline-8-sulphonylamino]-benzothiazole A suspension of 0.39 g (0.83 mmol) of 2-[(4-cyanophenyl)oxymethyl]-5-(quinoline-8-sulphonylamino)-benzothiazole, 0.23 ml (0.35 g, 2.1 mmol) of bromoethyl acetate, 0.14 ml (0.14 g, 0.94 mmol) of 1,8-diazabicyclo[5,4,0]undec-7-ene and 0.60 g (4.1 mmol) of potassium carbonate in 30 ml of acetone is heated to boiling for 3 hours. Then it is filtered, the solvent is distilled off in vacuo and the residue is purified by flash chromatography (silica gel, methylene chloride:ethanol=99:1).

Yield: 0.41 g (61% of theory), $R_f$-value: 0.54 (silica gel; methylene chloride/ethanol=50:1 +a few drops of ammonia).

f. 2-[(4-Amidinophenyl)oxymethyl]-5-[N-(methoxycarbonyl-methyl)-quinoline-8-sulphonylamino]-benzothiazole-hydrochloride Prepared analogously to Example 1e from 2-[(4-cyanophenyl)oxymethyl]-5-[N-[ethoxycarbonylmethyl)-quinoline-8-sulphonylamino]-benzothiazole and methanolic hydrochloric acid, methanol and ammonium carbonate.

Yield: 67% of theory, $C_{27}H_{23}N_5O_5S_2$(561.64); $R_f$-value: 0.36 (silica gel; methylene chloride/ethanol 4:1); Mass spectrum (SKA): $(M+H)^+$=562; $(M+H+Na)^{++}$=292.7.

EXAMPLE 83

1-methyl-2-(4-amidinobenzylthio)-5-[N-(methoxycarbonylmethyl)-quinoline-8-sulphonylamino]-benzimidazole Prepared analogously to Example 1e from 1-methyl-2-(4-cyanobenzylthio)-5-[N-(methoxycarbonylmethyl)- quinoline-8-sulphonylamino]-benzimidazole and methanolic hydrochloric acid, methanol and ammonium carbonate.

Yield: 50% of theory, $C_{28}H_{26}N_6O_4S_2$(574.69); $R_f$-value: 0.35 (silica gel; ethyl acetate/ethanol/ammonia=50:45:5); Mass spectrum (EKA): $(M+H)^+$=575; $(M+H+Na)^{++}$=299.

EXAMPLE 84

1-methyl-2-[4-(N-ethoxycarbonyl-amidino)-benzylthio]-5-[N-(methoxycarbonylmethyl)-quinoline-8-sulphonylamino]-benzimidazole Prepared analogously to Example 31 from 1-methyl-2-(4-amidino-benzylthio)-5-[N-(methoxycarbonylmethyl)-quinoline-8-sulphonylamino]-benzimidazole and ethyl chloroformate.

Yield: 62% of theory, $C_{31}H_{30}N_6O_6S_2$(646.75); $R_f$-value: 0.55 (silica gel; ethyl acetate/ethanol/ammonia=50:45:5); Mass spectrum (EKA): $(M+H)^+$=647; $(M+Na)^+$=669.

EXAMPLE 85

1-methyl-2-(4-amidinobenzylthio)-5-[N-(hydroxycarbonylmethyl)-quinoline-8-sulphonylamino]-benzimidazole Prepared analogously to Example 3 from 1-methyl-2-(4-amidinobenzylthio)-5-[N-(methoxycarbonylmethyl)-quinoline-8-sulphonylamino]-benzimidazole and sodium hydroxide solution.

Yield: 61.5% of theory, $C_{27}H_{24}N_6O_4S$(560.66); $R_f$-value: 0.20 (silica gel; ethyl acetate:ethanol:ammonia=50:45:5); Mass spectrum (EKA): $(M+H)^+$=561; $(M+Na)^+$=583.

EXAMPLE 86

2-[(4-Amidinophenyl)-oxymethyl]-5-[N-(hydroxycarbonylmethyl)-quinoline-8-sulphonylamino]-benzothiazole Prepared analogously to Example 3 from 2-[(4-amidinophenyl)-oxymethyl]-5-[N-(methoxycarbonylmethyl)-quinoline-8-sulphonylamino]-benzothiazole and sodium hydroxide solution.

Yield: 93% of theory, $C_{26}H_{21}N_5O_5S_2$(547.62); $R_f$-value: 0.13 (silica gel; dichloromethane/ethanol=4:1); Mass spectrum (EKA): $(M+H)^+$=548; $(M+2H)^{++}$=274.6; $(M+H+Na)^{++}$=285.6; $(M+2Na)^{++}$=296.6.

EXAMPLE 87

1-methyl-2-(4-amidinobenzylthio)-5-benzoylamino-benzimidazole

Prepared analogously to Example 1e from 1-methyl-2-(4-cyanobenzylthio)-5-benzoylaminobenzimidazole and ethanolic hydrochloric acid, ethanol and ammonium carbonate.

Yield: 54.8% of theory, $C_{23}H_{21}N_5OS$(415.52); $R_f$-value: 0.35 (silica gel; ethyl acetate/ethanol/ammonia=50:45:5); Mass spectrum (EKA): $(M+H)^+$=416.

EXAMPLE 88

2-[N-(4-Amidinophenyl)-aminomethyl]-5-[N-(ethoxycarbonylmethyl)quinoline-8-sulphonylamino]-benzothiazole Prepared analogously to Example 1e from 2-[N-(4-cyanophenyl)-aminomethyl]-5-[N-(ethoxycarbonylmethyl)-quinoline-8-sulphonylamino]-benzothiazole and ethanolic hydrochloric acid, ethanol and ammonium carbonate.

Yield: 80% of theory, $C_{28}H_{26}N_6O_4S_2$(574.69); $R_f$-value: 0.24 (silica gel; dichloromethane/ethanol=4:1); Mass spectrum (EKA): $(M+H)^+$=575; $(M+H+Na)^{++}$=299.

EXAMPLE 89

2-[N-(4-Amidinophenyl)-aminomethyl]-5-[N-(hydroxycarbonylmethyl)-quinoline-8-sulphonylamino]-benzothiazole Prepared analogously to Example 3 from 2-[N-(4-amidinophenyl)-aminomethyl]-5-[N-(ethoxycarbonylmethyl)-quinoline-8-sulphonylamino]-benzothiazole and sodium hydroxide solution.

Yield: 94% of theory, $C_{26}H_{22}N_6O_4S_2$(546.63); $R_f$-value: 0.15 (silica gel; dichloromethane/ethanol=4:1); Mass spectrum (EKA): $(M+H)^+$=547; $(M+Na)^+$=569; $(M+2H)^{++}$=274; $(M+H+Na)^{++}$=285; $(M+2Na)^{++}$=296; $(2M+3Na)^{3+}$=387.

EXAMPLE 90

1-methyl-2-(4-amidinobenzylthio)-5-[N-(ethoxycarbonylmethyl)-benzoylamino]-benzimidazole Prepared analogously to Example 1e from 1-methyl-2-(4-cyanobenzylthio)-5-[N-(ethoxycarbonylmethyl)-benzoylamino]-benzimidazole and ethanolic hydrochloric acid, ethanol and ammonium carbonate.

Yield: 68.8% of theory, $C_{27}H_{27}N_5O_3S$(538.08); $R_f$-value: 0.27 (silica gel; ethyl acetate/ethanol/ammonia=50:45:5); Mass spectrum (EKA): $(M+H)^+$=502; $(M+H+Na)^{++}$=262.8.

EXAMPLE 91

1-methyl-2-(4-amidinobenzlthio)-5-[N-(hydroxycarbonylmethyl)-benzoylamino]-benzimidazole Prepared analogously to Example 3 from 1-methyl-2-(4-amidinobenzylthio)-5-[N-(ethoxycarbonylmethyl)-benzoylamino]-benzimidazole and sodium hydroxide solution.

Yield: 79% of theory, $C_{25}H_{23}N_5O_3S$(473.53); $R_f$-value: 0.21 (silica gel; ethyl acetate/ethanol/ammonia=50:45:5); Mass spectrum (EKA): $(M+H)^+$=474; $(M+Na)^+$=496.

EXAMPLE 92

2-[2-(4-Amidinophenyl)-ethyl]-3-methyl-6-[N-(ethoxycarbonylmethyl)-quinoline-8-sulphonylamino]-imidazo[4,5-b]pyridine a. 3,5-di-[3-(4-cyanophenyl)propionylamido]-2-methylamino-pyridine A solution of 3.8 g (19 mmol) of 3,5-dinitro-2-methylamino-pyridine in 90 ml of ethanol/methylene chloride (2:1) is hydrogenated at 5 bar hydrogen pressure with 1.0 g 10% palladium on charcoal within 2 hours. The catalyst is filtered off, and the solvent is distilled off in vacuo. The black, oily crude product is dissolved in 50 ml of pyridine and at 0° C. 7.0 g (36 mmol) of 3-(4-cyanophenyl)propionic acid chloride are added. After 2 hours the solvent is distilled off in vacuo, the residue is taken up in 100 ml of ethyl acetate and washed with water and saturated sodium chloride solution. It is dried with sodium sulphate, the solvent is distilled off and the residue obtained is purified by flash chromatography (silica gel, methylene chloride/ethanol=49:1 to 19:1).

Yield: 4.8 g (59% of theory), R$_f$-value: 0.40 (silica gel; ethyl acetate/ethanol/ammonia=90:10:1).

b. 3-methyl-2-[2-(4-cyanophenyl)-ethyl]-6-[3-(4-cyanophenyl)propionylamido]-imidazo[4,5-b]pyridine A solution of 1.6 g (3.5 mmol) of 3,5-di-[3-(4-cyanophenyl)propionylamido]-2-methylamino-pyridine in 30 ml of glacial acetic acid is heated to 100° C. for 1 hour. Then the solvent is distilled off in vacuo, the residue is taken up in 80 ml of methylene chloride and neutralised with sodium hydrogen carbonate solution. The organic phase is dried with sodium sulphate, the solvent is distilled off in vacuo and the crude product is purified by flash chromatography (silica gel, methylene chloride/ethanol=49:1 to 19:1).

Yield: 0.90 g (60% of theory), R$_f$-value: 0.46 (silica gel; ethyl acetate/ethanol/ammonia=90:10:1).

c. 6-amino-3-methyl-2-[2-(4-cyanophenyl)-ethyl]-imidazo[4,5-b]

0.80 g (1.8 mmol) of 3-methyl-2-[2-(4-cyanophenyl)-ethyl]-6-[3-(4-cyanophenyl)propionylamido]-imidazo[4,5-b]pyridine is heated to 100° C. in 20 ml of 0.5N hydrochloric acid for 2 hours. After cooling the mixture is made alkaline with ammonia and extracted with ethyl acetate. The organic phase is washed with saturated sodium chloride solution and the solvent is distilled off.

Yield: 0.42 g (84% of theory), R$_f$-value: 0.30 (silica gel; ethyl acetate/ethanol/ammonia=90:10:1).

d. 2-[2-(4-cyanophenyl)-ethyl]-3-methyl-6-(quinoline-8-sulphonylamino)-imidazo[4,5-b]pyridine Prepared analogously to Example 79c from 0.40 g (1.4 mmol) of 6-amino-3-methyl-2-[2-(4-cyanophenyl)-ethyl]-imidazo[4,5-b]pyridine with 0.39 g (1.6 mmol) of quinoline-8-sulphonic acid chloride.

Yield: 0.60 g (90% of theory), R$_f$-value: 0.74 (silica gel; ethyl acetate/ethanol/ammonia=90:10:1).

e. 2-[2-(4-cyanophenyl)-ethyl]-3-methyl-6-[N-(ethoxycarbonylmethyl)-quinoline-8-sulphonylamino]-imidazo[4,5-b]pyridine Prepared analogously to Example 82e from 0.60 g (1.3 mmol) of 2-[2-(4-cyanophenyl)-ethyl]-3-methyl-6-(quinoline-8-sulphonylamino)-imidazo[4,5-b]pyridine with 0.33 g (1.5 mmol) of bromoethyl acetate.

Yield: 0.70 g (98% of theory), R$_f$-value: 0.80 (silica gel; ethyl acetate/ethanol/ammonia=90:10:1).

f. 2-[2-(4-Amidinolphenyl)-ethyl]-3-methyl-6-[N-(ethoxycarbonylmethyl)-quinoline-8-sulphonylamino]-imidazo[4,5-b]pyridine Prepared analogously to Example 1e from 2-[2-(4-cyanophenyl)-ethyl]-3-methyl-6-[N-(ethoxycarbonylmethyl)-quinoline-8-sulphonylamino]-imidazo[4,5-b]pyridine and ethanolic hydrochloric acid, ethanol and ammonium carbonate.

Yield: 91% of theory, C$_{29}$H$_{29}$N$_7$O$_4$S(571.66); R$_f$-value: 0.22 (silica gel; ethyl acetate/ethanol/ammonia=50:45:5); Mass spectrum (SKA): (M+H)$^+$=572; (M+H+Na)$^{++}$=297.8.

EXAMPLE 93

2-[2-(4-Amidinophenyl)-ethyl]-3-methyl-6-[N-(hydroxycarbonylmethyl)-quinoline-8-sulphonylamino]-imidazo[4,5-b]pyridine Prepared analogously to Example 3 from 2-[2-(4-amidinophenyl)-ethyl]-3-methyl-6-[N-(ethoxycarbonylmethyl)-quinoline-8-sulphonylamino]-imidazo[4,5-b]pyridine and sodium hydroxide solution.

Yield: 77% of theory, C$_{27}$H$_{25}$N$_7$O$_4$S(543.59); R$_f$-value: 0.16 (silica gel; ethyl acetate/ethanol/ammonia=50:45:5); Mass spectrum (EKA): (M+H)$^+$=544; (M+H+Na)$^{++}$=283,8.

EXAMPLE 94

1-methyl-2-[N-(4-amidinophenyl)-aminomethyl]-5-[N-(ethoxycarbonylmethyl)-quinoline-8-sulphonylamino]-indole Prepared analogously to Example 1e from 1-methyl-2-[N-(4-cyanophenyl)-aminomethyl]-5-[N-(ethoxycarbonylmethyl)-quinoline-8-sulphonylamino]-indole and ethanolic hydrochloric acid, ethanol and ammonium carbonate.

Yield: 55% of theory, C$_{30}$H$_{30}$N$_6$O$_4$S(570.68); R$_f$-value: 0.22 (silica gel; dichloromethane/ethanol=4:1); Mass spectrum (EKA): (M+H)$^+$=571; (M+2H)$^{++}$=286; (M+H+Na)$^{++}$=297.

EXAMPLE 95

1-methyl-2-[N-(4-amidinophenyl)-aminomethyl]-5-[N-(hydroxycarbonylmethyl)-quinoline-8-sulphonylamino]-indole Prepared analogously to Example 3 from 1-methyl-2-[N-(4-amidinophenyl)-aminomethyl]-5-[N-(ethoxycarbonylmethyl)-quinoline-8-sulphonylamino]-indole and sodium hydroxide solution.

Yield: 97% of theory, C$_{28}$H$_{26}$N$_6$O$_4$S(542.62); Mass spectrum (EKA): (M+H)$^+$=543; (M+Na)$^+$=565; (M+2H)$^{++}$=272; (M+H+Na)$^{++}$=283; (M+2Na)$^{++}$=294; $^1$H-NMR (d$_6$-DMSO): δ=3.61 (s,3H); 4.50 (d,2H); 4.67 (s,2H); 6.20 (s,1H); 6.30 (d,1H); 6.70 (d,2H); 7.01 (d,1H); 7.29 (t,1H); 7.38 (s,1H); 7.40–7.65 (m,3H); 7.77 (dd,1H); 8.03 (d,1H); 8.20 (d,1H); 8.42 (broad s,2H); 8.55 (dd,1H); 9.20 (dd,1H) ppm.

EXAMPLE 96

1-methyl-2-[(4-amidinophenyl)-thiomethyl]-5-[N-(ethoxycarbonylmethyl)-quinoline-8-sulphonylamino]-benzimidazole Prepared analogously to Example 1e from 1-methyl-2-[(4-cyano-phenyl)-thiomethyl]-5-[N-(ethoxycarbonylmethyl)-quinoline-8-sulphonylamino]-benzimidazole and ethanolic hydrochloric acid, ethanol and ammonium carbonate.

Yield: 84% of theory, C$_{29}$H$_{28}$N$_6$O$_4$S$_2$(588.71); R$_f$-value: 0.35 (silica gel; ethyl acetate/ethanol/ammonia=50:45:5); Mass spectrum (EKA): (M+H)$^+$=589; (M+H+Na)$^{++}$=306.

EXAMPLE 97

1-methyl-2-[(4-amidinophenyl)-thiomethyl]-5-[N-(hydroxycarbonylmethyl)-quinoline-8-sulphonylamino]-benzimidazole Prepared analogously to Example 3 from 1-methyl-2-[(4-amidinophenyl)-thiomethyl]-5-[N-(ethoxycarbonylmethyl)-quinoline-8-sulphonylamino]-benzimidazole and sodium hydroxide solution.

Yield: 76% of theory, C$_{27}$H$_{24}$N$_6$O$_4$S(560.66); R$_f$-value: 0.21 (silica gel; ethyl acetate/ethanol/ammonia=50:45:5); Mass spectrum (EKA): (M+H)$^+$=561; (M+Na)$^+$=583.

EXAMPLE 98

1-methyl-2-[(4-amidinophenyl)-thiomethyl]-5-(quinoline-8-sulphonylamino)-benzimidazole Prepared analogously to Example 1e from 1-methyl-2-[(4-cyanophenyl)-thiomethyl]-5-(quinoline-8- sulphonylamino)-benzimidazole and ethanolic hydrochloric acid, ethanol and ammonium carbonate.

Yield: 70% of theory, $C_{25}H_{22}N_6O_2S_2(502.62)$; $R_f$-value: 0.29 (silica gel; ethyl acetate/ethanol/ammonia=50:45:5); Mass spectrum (EKA): $(M+H)^+=503$.

EXAMPLE 99

2-[(4-Amidinophenyl)-acetyl]-7-(quinoline-8-sulphonylamino)-1,2,3,4-tetrahydro-isoquinoline-hydrochloride a. 2-[(4-cyanophenyl)-acetyl]-7-nitro-1,2,3,4-tetrahydro-isoquinoline 4.0 g (22.5 mmol) of 7-nitro-1,2,3,4-tetrahydro-isoquinoline are dissolved in 100 ml of chlorobenzene, mixed with 4.24 g (25 mmol) of 4-cyanophenylacetic acid chloride and refluxed for 2 hours. After cooling to ambient temperature the mixture is diluted with 1 l of petroleum ether and filtered. The residue is dissolved in ethyl acetate and chromatographed on silica gel, eluting first with methylene chloride, later with methylene chloride/ethanol (50:1 and 25:1). The desired fractions are combined and evaporated down.

Yield: 3.80 g (53% of theory), $R_f$-value: 0.50 (silica gel; methylene chloride/ethanol=19:1).

b. 2-[(4-cyanophenyl)-acetyl]-7-amino-1,2,3,4-tetrahydro-isoquinoline

Prepared analogously to Example 1b from 2-[(4-cyanophenyl)-acetyl]-7-nitro-1,2,3,4-tetrahydro-isoquinoline and hydrogen/palladium.

Yield: 27% of theory, Melting point: 186–188° C.

c. 2-[(4-cyanophenyl)-acetyl]-7-(quinoline-8-sulphonylamino)-1,2,3,4-tetrahydro-isoquinoline Prepared analogously to Example 1c from 2-[(4-cyanophenyl)-acetyl]-7-amino-1,2,3,4-tetrahydro-isoquinoline and quinoline-8-sulphonylchloride.

Yield: 80% of theory, $R_f$-value: 0.55 (silica gel; methylene chloride/ethanol=19:1).

d. 2-[(4-Amidinophenyl)-acetyl]-7-(quinoline-8-sulphonylamino)-1,2,3,4-tetrahydro-isoquinoline-hydrochloride Prepared analogously to Example 1e from 2-[(4-cyanophenyl)-acetyl]-7-(quinoline-8-sulphonylamino)-1,2,3,4-tetrahydro-isoquinoline and hydrochloric acid/ammonium carbonate in ethanol.

Yield: 35% of theory, Melting point: sinters from 173° C.; $C_{27}H_{25}N_5O_3S(499.50)$; Mass spectrum: $(M+H)^+=500$.

EXAMPLE 100

2-[(4-Amidinophenyl)-acetyl]-7-[N-(ethoxycarbonylmethyl)-quinoline-8-sulphonylamino]-1,2,3,4-tetrahydro-isoquinoline Prepared analogously to Example 1e from 2-[(4-cyanophenyl)-acetyl]-7-[N-(ethoxycarbonylmethyl)-quinoline-8-sulphonylamino]-1,2,3,4-tetrahydro-isoquinoline and ethanolic hydrochloric acid, ethanol and ammonium carbonate.

Yield: 35% of theory, $C_{31}H_{31}N_5O_5S(585.68)$; $R_f$-value: 0.20 (silica gel; dichloromethane/ethanol=4:1); Mass spectrum (EKA): $(M+H)^+=586$; $(M+2H)^{++}=293.6$; $(M+H+Na)^{++}=304.6$.

EXAMPLE 101

2-[(4-Amidinophenyl)-acetyl]-7-[N-(hydroxycarbonylmethyl)-quinoline-8-sulphonylamino]-1,2,3,4-tetrahydro-isoquinoline Prepared analogously to Example 3 from 2-[(4-amidinophenyl)-acetyl]-7-[N-(ethoxycarbonylmethyl)-quinoline-8-sulphonylamino]-1,2,3,4-tetrahydro-isoquinoline and sodium hydroxide solution.

Yield: 49% of theory, $C_{29}H_{27}N_5O_5S(557.6)$; $R_f$-value: 0.17 (silica gel; dichloromethane/ethanol=3:2); Mass spectrum (EKA): $(M+H)^+=558$; $(M+Na)^+=580$; $(M+2H)^{++}=279.7$; $(M+H+Na)^{++}=290.7$; $(2M+H+Na)^{++}=569$.

EXAMPLE 102

2-[(4-Amidinophenyl)-oxymethyl]-4-methyl-7-[N-(ethoxycarbonylmethyl)-quinoline-8-sulphonylamino]-quinoline-hydrochloride a. 7-amino-2,4-dimethyl-quinoline 54.8 g (0.36 mol) of 3-acetylamino-aniline, 38.0 g (0.38 mol) of acetyl acetone and 32.5 ml of glacial acetic acid are stirred for 2 hours at 80° C. After cooling the reaction mixture is poured onto ice water and neutralised with sodium hydrogen carbonate solution. After extracting three times with ethyl acetate the combined organic phases are washed with saline solution, dried over sodium sulphate and concentrated by evaporation. The crude product thus obtained is heated to 105° C. for 1 hour with 200 ml of conc. sulphuric acid. After cooling the reaction mixture is poured onto ice water and neutralised with ammonia solution. After extracting three times with ethyl acetate the combined organic phases are washed with saline solution, dried over sodium sulphate and concentrated by evaporation. The crude product is chromatographed on silica gel, elu-ting first with methylene chloride, later with methylene chloride/ethanol (50:1, 25:1, 19:1 and 9:1). The desired fractions are combined, evaporated down and triturated with petroleum ether.

Yield: 24.15 g (39% of theory), $C_{11}H_{12}N_2(172.20)$; Mass spectrum: $M^+=172$.

b. 7-phthalimido-2,4-dimethyl-quinoline 6.90 g (40 mmol) of 7-amino-2,4-dimethyl-quinoline, 5.95 g (42 mmol) of phthalic acid anhydride and 100 ml of glacial acetic acid are refluxed for 2 hours. After cooling the reaction mixture is poured onto ice water, the precipitated product is suction filtered, washed with water and dried.

Yield: 8.85 g (73% of theory), Melting point: 203–205° C.

c. 7-phthalimido-2,4-dimethyl-quinoline-1-oxide 4.25 g (14 mmol) of 7-phthalimido-2,4-dimethyl-quinoline are dissolved in 500 ml of boiling methylene chloride. After cooling to ambient temperature, 4.80 g of 3-chloroperbenzoic acid (about 50% strength) are added. After 3 hours at ambient temperature the reaction solution is washed 1 x with sodium hydrogen carbonate solution and saline solution, dried over sodium sulphate, concentrated by evaporation and recrystallised from ethanol.

Yield: 2.45 g (55% of theory), Melting point: >250° C.

d. 2-chloromethyl-4-methyl-phthalimido-quinoline 4.30 g (13.5 mmol) of 7-phthalimido-2,4-dimethyl-quinoline-1-oxide and 4.20 g (22 mmol) of p-toluenesulphochloride are refluxed in 300 ml of methylene chloride for 8 hours. After cooling to ambient temperature the reaction solution is washed 1 x each with sodium hydrogen carbonate solution and saline solution, dried over sodium sulphate and concentrated by eva-poration. The residue is chromatographed on silica gel, eluting first with methylene chloride, later with methylene chloride/ethanol (50:1). The desired fractions are combined, concentrated by evaporation and triturated with ether.

Yield: 3.15 g (70% of theory), Melting point: 212–215° C.

e. 2-[(4-cyanophenyl)-oxymethyl]-4-methyl-phthalimido-quinoline 895 mg (6.2 mmol) of potassium-tert.butoxide are dissolved in 50 ml of dimethylsulphoxide, mixed with 740 mg (6.2 mmol) of 4-hydroxy-benzonitrile and stirred for 30 minutes at ambient temperature. After the addition of 2.0 g of 2-chloromethyl-4-methyl-7-phthalimido-quinoline the reaction mixture is stirred for a further 12 hours at ambient temperature. After the addition of ice water the precipitate formed is removed by suction filtering, washed with water and dried.

Yield: 2.20 g (89% of theory), Melting point: 231–233° C.

f. 2-[(4-cyanophenyl)-oxymethyl]-4-methyl-7-amino-quinoline 2.15 g (5.1 mmol) of 2-[(4-cyanophenyl)-oxymethyl]-4-methyl-7-phthalimido-quinoline are dissolved in 75 ml of toluene/methanol (2:1), mixed with 7.5 ml of 40% aqueous methylamine solution and stirred for 2 hours at ambient temperature. Then the solution is concentrated by evaporation in vacuo, the residue is stirred with 2N acetic acid, suction filtered and dried. The crude product is chromatographed on silica gel, eluting first with methylene chloride, later with methylene chloride/ethanol (50:1). The desired fractions are combined, concentrated by evaporation and triturated with ether.

Yield: 1.05 g (71% of theory), Melting point: 192–194° C.

g. 2-[(4-cyanophenyl)-oxmethyl]-4-methyl-7-(quinoline-8-sulphonylamino)-quinoline Prepared analogously to Example 1c from 2-[(4-cyanophenyl)-oxymethyl]-4-methyl-7-amino-quinoline and quinoline-8-sulphonylchloride.

Yield: 67% of theory, Melting point: 240–242° C.

h. 2-[(4-cyanophenyl)-oxymethyl]-4-methyl-7-[N-(ethoxycarbonylmethyl)-quinoline-8-sulphonylamino)-quinoline Prepared analogously to Example 1d from 2-[(4-cyanophenyl)-oxymethyl]-4-methyl-7-(quinoline-8-sulphonylamino)-quinoline and bromoethyl acetate.

Yield: 92% of theory, Melting point: sinters from 85° C.

i. 2-[(4-Amidinophenyl)-oxymethyl]-4-methyl-7-[N-(ethoxycarbonylmethyl)-quinoline-8-sulphonylamino)-quinoline-hydrochloride Prepared analogously to Example 1e from 2-[(4-cyanophenyl)-oxymethyl]-4-methyl-7-[N-(ethoxycarbonylmethyl)-quinoline-8-sulphonylamino)-quinoline and hydrochloric acid/ammonium carbonate in ethanol.

Yield: 49% of theory, Melting point: sinters from 78° C.; $C_{31}H_{29}N_5O_5S(583.62)$; Mass spectrum: $(M+H)^+=584$; $(M+H+Na)^+=303.7$; $(2M+H)^+=1167$.

EXAMPLE 103

2-[(4-Amidinophenyl)-oxymethyl]-4-methyl-7-[N-(-hydroxycarbonylmethyl)-quinoline-8-sulphonylamino]-quinoline Prepared analogously to Example 3 from 2-[(4-amidinophenyl)-oxymethyl]-4-methyl-7-[N-(ethoxycarbonylmethyl)-quinoline-8-sulphonylamino]-quinoline and sodium hydroxide solution.

Yield: 19% of theory, $C_{29}H_{25}N_5O_5S(555.6)$; Mass spectrum (EKA): $(M+H)^+=556$; $(M+Na)^+=578$; $(M+2Na)^{++}=300$; $(M-H+2Na)^+=600$.

EXAMPLE 104

2-[(4-Amidinophenyl)-oxymethyl]-4-methyl-7-(quinoline-8-sulphonylamino)-quinoline Prepared analogously to Example 1e from 2-[(4-cyanophenyl)-oxymethyl]4-methyl-7-(quinoline-8-sulphonylamino)-quinoline and ethanolic hydrochloric acid, ethanol and ammonium carbonate.

Yield: 22% of theory, $C_{27}H_{23}N_5O_3S(497.55)$; $R_f$-value: 0.23 (silica gel; dichloromethane/ethanol=4:1); Melting point: sinters from 195° C.; Mass spectrum (EKA): $(M+H)^+=498$.

EXAMPLE 105

2-[N-(4-Amidinophenyl)-aminomethyl]-6-(quinoline-8-sulphonylamino)-imidazo[1,2-a] pyridine-hydrochloride a. 2-chloromethyl-5-nitro-imidazo[1,2-a]pyridine 12.6 g (0.1 mol) of 1,3-dichloroacetone are heated to 105° C. and 8.25 g (60 mmol) of 2-amino-5-nitro-pyridine are added batchwise. After 10 minutes at 105° C. the reaction mixture is cooled, mixed with methylene chloride/ethanol (8:2) and chromatographed on silica gel, eluting first with methylene chloride, later with methylene chloride/ethanol (25:1, 19:1 and 9:1). The desired fractions are combined, concentrated by evaporation and triturated with ether.

Yield: 4.35 g (34% of theory), Melting point: 124–127° C.

b. 2-[N-(4-cyanophenyl)-aminomethyl]-6-nitro-imidazo[1,2-a]-pyridine 3.0 g (25.4 mmol) of 4-aminobenzonitrile are melted at 120° C. and 1.30 g (6.3 mmol) of 2-chloromethyl-5-nitro-imidazole[1,2-a]pyridine are added batchwise. After 30 minutes at 120° C. the reaction mixture is cooled, mixed with methylene chloride/ethanol (8:2) and chromatographed on silica gel, eluting first with methylene chloride, later with methylene chloride/ethanol (50:1, 25:1 and 15:1). The desired fractions are combined and concentrated by evaporation.

Yield: 0.71 g (39% of theory), $R_f$-value: 0.50 (silica gel; methylene chloride/ethanol=19:1).

c. 2-[N-(4-cyanophenyl)-aminomethyl]-6-amino-imidazo[1,2-a]-pyridine

Prepared analogously to Example 1b from 2-[N-(4-cyanophenyl)-aminomethyl]-6-nitro-imidazo[1,2-a] pyridine and hydrogen/palladium.

Yield: 75% of theory, $R_f$-value: 0.20 (silica gel; methylene chloride/ethanol=9:1).

d. 2-[N-(4-cyanophenyl)-aminomethyl]-6-(quinoline-8-sulphonylamino)-methylamino-pyridine imidazo[1,2-a] pyridine Prepared analogously to Example 1c from 2-[N-(4-cyanophenyl)-aminomethyl]-6-amino-imidazo[1,2-a] pyridine and quinoline-8-sulphonylchloride.

Yield: 35% of theory, $R_f$value: 0.78 (silica gel; methylene chloride/ethanol=4:1+glacial acetic acid).

e. 2-[N-(4-Amidinophenyl)-aminomethyl]-6-(quinoline-8-sulphonylamino)-imidazo[1,2-a]pyridine-hydrochloride Prepared analogously to Example 1e from 2-[N-(4-cyanophenyl)-aminomethyl]-6-(quinoline-8-sulphonylamino)-imidazo[1,2-a]pyridine and hydrochloric acid/ammonium carbonate.

Yield: 51% of theory, $R_f$-value: 0.15 (silica gel; methylene chloride/ethanol=4:1+glacial acetic acid); $C_{24}H_{27}N_7O_2S$ (471.48); Mass spectrum: $(M+H)^+=472$.

EXAMPLE 106

2-[N-(4-Amidinophenyl)-aminomethyl]-6-[N-(ethoxycarbonyl-methyl)-quinoline-8-sulphonylamino]-imidazo[1,2-a]pyridine Prepared analogously to Example 1e from 2-[N-(4-cyanophenyl)-aminomethyl]-6-[N-(ethoxycarbonylmethyl)- quinoline-8-sulphonylamino]-imidazo[1,2-a]pyridine and ethanolic hydrochloric acid, ethanol and ammonium carbonate.

Yield: 11% of theory, $C_{28}H_{27}N_7O_4S$(557.65); Mass spectrum (EKA): $(M+H)^+$=558; $(M+Na)^+$=580.

EXAMPLE 107

2-[N-(4-Amidinophenyl)-aminomethyl]-3-methyl-6-[N-(ethoxycarbonylmethyl)-quinoline-8-sulphonylamino]-benzofuran-hydrochloride a. 4-acethylamino-2-hydroxy-acetophenone 16.5 g (0.10 mol) of 3-methoxy-acetanilide are dissolved in 40 ml of dichloroethane and after the addition of 19.6 g (0.25 mol) of acetyl chloride, 42.0 g (0.32 mol) of aluminium chloride are added batchwise at 5° C. After 2 hours at ambient temperature the reaction mixture is refluxed for a further 2 hours. After cooling to ambient temperature ice is added, the precipitate formed is suction filtered, washed with water and dried.

Yield: 14.8 g (77% of theory), $R_f$-value: 0.40 (silica gel; petroleum ether/ethyl acetate=1:1).

b. 4-amino-2-hydroxy-acetophenone 10.0 g (52 mmol) of 4-acetylamino-2-hydroxy-acetophenone and 100 ml of 18% hydrochloric acid are refluxed for 15 minutes. After cooling to ambient temperature the precipitate formed is suction filtered, washed with ice water and dried. The filtrate is concentrated by evaporation, taken up in water and mixed with conc. ammonia. The precipitate formed is suction filtered, washed with ice water, dried and combined with the first precipitate.

Yield: 7.6 g (97% of theory), $R_f$-value: 0.65 (silica gel; petroleum ether/ethyl acetate=1:1).

c. 4-phthalimido-2-hydroxy-acetophenone

Prepared analogously to Example 102b from 4-amino-2-hydroxy-acetophenone and phthalic anhydride.

Yield: 75% of theory, $R_f$-value: 0.55 (silica gel; petroleum ether/ethyl acetate=1:1).

d. 4-[(2-carboxy)-benzoylamino]-2-carboxymethyloxy-acetophenone 18.9 g (67 mmol) of 4-phthalimido-2-hydroxy-acetophenone, 16.5 g (99 mmol) of bromoethyl acetate and 40.0 g (0.3 mol) of potassium carbonate are taken up in 100 ml of acetone and refluxed for 6 hours. After cooling to ambient temperature is the precipitate formed is suction filtered and dried. The filtrate is concentrated by evaporation, taken up in water and extracted 3 x with ethyl acetate. The combined organic extracts are washed with water and dried. The combined crude products are dissolved in 50 ml of ethanol, mixed with 50 ml of 3 N sodium hydroxide solution and stirred for 30 minutes at ambient temperature. After the addition of 100 ml of water and acidification with 6 N hydrochloric acid the precipitate formed is suction filtered, washed with cold water and dried.

Yield: 19.4 g (81% of theory), $R_f$-value: 0.30 (silica gel; methylene chloride/ethanol=7:3).

e. 3-methyl-6-phthalimido-benzofuran

A mixture of 36.0 g (0.1 mol) of 4-[(2-carboxy)-benzoylamino]-2-carboxymethyloxy-acetophenone, 30 g (0.37 mol) of sodiumacetate, 770 ml of acetic anhydride and 153 ml of glacial acetic acid are refluxed for 2.5 hours. The reaction mixture is concentrated by evaporation, the residue is triturated with water, suction filtered, washed with water and dried.

Yield: 21.6 g (77% of theory), $R_f$-value: 0.85 (silica gel; methylene chloride +2.5% ethanol).

f. 2-[N-(4-cyanophenyl)-aminomethyl]-3-methyl-6-phthalimido-benzofuran 5.68 g (20 mmol) of 3-methyl-6-phthalimido-benzofuran are dissolved in 150 ml of methylene chloride, mixed with 5.0 g of paraformaldehyde and 20 g of thionylchloride and stirred for 60 hours at ambient temperature. The reaction mixture is concentrated by evaporation, dissolved twice in methylene chloride and again evaporated to dryness. The crude product is dissolved in 150 ml of toluene, mixed with 5.1 g (43 mmol) of 4-amino-benzonitrile and 20 g of aluminium oxide and refluxed for 6 hours. The reaction mixture is concentrated by evaporation, the residue is taken up in methylene chloride and chromatographed on silica gel (methylene chloride). The desired fractions are combined, concentrated by evaporation and triturated with petroleum ether/methylene chloride.

Yield: 6.0 g (68% of theory), $R_f$-value: 0.30 (silica gel; methylene chloride).

g. 2-[N-(4-cyanophenyl)-aminomethyl]-3-methyl-6-amino-benzofuran

Prepared analogously to Example 102f from 2-[N-(4-cyanophenyl)-aminomethyl]-3-methyl-6-phthalimido-benzofuran and methylamine.

Yield: 65% of theory, $R_f$-value: 0.25 (silica gel; methylene chloride).

h. 2-[N-(4-cyanophenyl)-aminomethyl]-3-methyl-6-(quinoline-8-sulphonylamino)-benzofuran Prepared analogously to Example 1c from 2-[N-(4-cyanophenyl)-aminomethyl]-3-methyl-6-amino-benzofuran and quinoline-8-sulphonylchloride.

Yield: 97% of theory, $R_f$-value: 0.65 (silica gel; methylene chloride/ethanol=95:5).

i. 2-[N-(4-cyanophenyl)-aminomethyl]-3-methyl-6-[N-(ethoxycarbonylmethyl)-quinoline-8-sulphonylamino)-benzofuran Prepared analogously to Example 1d from 2-[N-(4-cyanophenyl)-aminomethyl]-3-methyl-6-(quinoline-8-sulphonylamino-benzofuran and bromoethyl acetate.

Yield: 99% of theory, $R_f$-value: 0.70 (silica gel; methylene chloride/ethanol=95:5).

i. 2-[N-(4-Amidinophenyl)-aminomethyl]-3-methyl-6-[N-(ethoxycarbonylmethyl)-quinoline-8-sulphonylamino]-benzofuran-hydrochloride Prepared analogously to Example 1e from 2-[N-(4-cyanophenyl)-aminomethyl]-3-methyl-6-[N-(ethoxycarbonylmethyl)-quinoline-8-sulphonylamino]-benzofuran and hydrochloric acid/ammonium carbonate.

Yield: 32% of theory, $R_f$-value: 0.21 (silica gel; methylene chloride/ethanol=4:1+glacial acetic acid); $C_{30}H_{29}N_5O_5S$ (571.67); Mass spectrum: $(M+H)^+$=572; $(M+2H)^{++}$=286.7; $(M+H+Na)^{++}$=297.7.

EXAMPLE 108

2-[N-(4-Amidinophenyl)-aminomethyl]-3-methyl-6-[N-(hydroxycarbonylmethyl)-quinoline-8-sulphonylamino]-benzofuran Prepared analogously to Example 3 from 2-[N-(4-amidinophenyl)-aminomethyl]-3-methyl-6-[N-(ethoxycarbonylmethyl)-quinoline-8-sulphonylamino]-benzofuran and sodium hydroxide solution.

Yield: 94% of theory, $C_{28}H_{25}N_5O_5S$(543.61); $R_f$-value: 0.12 (silica gel; dichloromethane/ethanol=4:1+glacial acetic acid); Mass spectrum (EKA): $(M+H)^+$=544; $(M+2H)^{++}$=272.7; $(M+H+Na)^{++}$=283.6; $(M+2Na)^{++}$=294.7.

EXAMPLE 109

2-[N-(4-Amidinophenyl)-aminomethyl]-3-methyl-6-(quinoline-8-sulphonylamino)-benzofuran Prepared analogously to Example 1e from 2-[N-(4-cyanophenyl)-aminomethyl]-3-methyl-6-(quinoline-8- sulphonylamino)-benzofuran and ethanolic hydrochloric acid, ethanol and ammonium carbonate.

Yield: 17% of theory, $C_{26}H_{23}N_5O_3S(485,58)$; $R_f$-value: 0.17 (silica gel; dichloromethane/ethanol=4:1+glacial acetic acid); Mass spectrum (EKA): (M+H)$^+$=486.

EXAMPLE 110

2-[(4-Amidinophenyl)-oxymethyl]-4-methyl-7-[N-(ethoxycarbonylmethyl)-benzoylamino]-quinoline Prepared analogously to Example 1e from 2-[(4-cyanophenyl)-oxymethyl]-4-methyl-7-[N-(ethoxycarbonylmethyl)-benzoylamino]-quinoline and ethanolic hydrochloric acid, ethanol and ammonium carbonate.

Yield: 64% of theory, $C_{29}H_{28}N_4O_4(496.6)$; Mass spectrum (EKA): (M+H)$^+$=497; (M+H+Na)$^{++}$=260.

EXAMPLE 111

2-[N-(-4-Amidinophenyl)-aminomethyl]-4-methyl-7-[N-(ethoxycarbonylmethyl)-quinoline-8-sulphonylamino]-quinoline Prepared analogously to Example 1e from 2-[N-(4-cyanophenyl)-aminomethyl]-4-methyl-7-[N-(ethoxycarbonylmethyl)-quinoline-8-sulphonylamino]-quinoline and ethanolic hydrochloric acid, ethanol and ammonium carbonate.

Yield: 63% of theory, $C_{31}H_{30}N_6O_4S(582.69)$; $R_f$-value: 0.15 (silica gel; dichloromethane/ethanol=4:1+glacial acetic acid); Mass spectrum (EKA): (M+H)$^+$=583; (M+H+Na)$^{++}$=303.

EXAMPLE 112

2-[N-(4-Amidinophenyl)-aminomethyl]-4-methyl-7-[N-(hydroxycarbonylmethyl)-quinoline-8-sulphonylamino]-quinoline Prepared analogously to Example 3 from 2-[N-(4-amidinophenyl)-aminomethyl]-4-methyl-7-[N-(ethoxycarbonylmethyl)-quinoline-8-sulphonylamino]-quinoline and sodium hydroxide solution.

Yield: 49% of theory, $C_{29}H_{26}N_6O_4S(554.64)$; Mass spectrum (EKA): (M+H)$^+$=555; (M+Na)$^+$=577; (M+2Na)$^{++}$=300; (2M+3Na)$^{3+}$=392.6.

EXAMPLE 113

2-[(4-Amidinophenyl)-oxymethyl]-4-methyl-7-[N-(hydroxycarbonylmethyl)-benzoylamino]-quinoline Prepared analogously to Example 3 from 2-[(4-amidinophenyl)-oxymethyl]-4-methyl-7-[N-(ethoxycarbonylmethyl)-benzoylamino]-quinoline and sodium hydroxide solution.

Yield: 26% of theory, $C_{27}H_{24}N_4O_4(468.49)$; Mass spectrum (EKA): (M+H)$^+$=469.

EXAMPLE 114

2-[2-(4-Amidinophenyl)-ethyl]-3-methyl-6-[N-(ethoxycarbonylmethyl)-quinoline-8-sulphonylamino]-benzofuran Prepared analogously to Example 1e from 2-[2-(4-cyanophenyl)-ethyl]-3-methyl-6-[N-(ethoxycarbonylmethyl)-quinoline-8-sulphonylamino]-benzofuran and ethanolic hydrochloric acid, ethanol and ammonium carbonate.

Yield: 84% of theory, $C_{31}H_{30}N_4O_5S(570.68)$; $R_f$-value: 0.24 (silica gel; dichloromethane/ethanol=4:1+glacial acetic acid); Mass spectrum (EKA): (M+H)$^+$=571; (M+H+Na)$^{++}$=297.

EXAMPLE 115

2-[N-(4-Amidinophenyl)-aminomethyl]-3-methyl-6-[N-(ethoxycarbonylmethyl)-benzenesulphonylamino]-benzofuran Prepared analogously to Example 1e from 2-[N-(4-cyanophenyl)-aminomethyl]-3-methyl-6-[N-(ethoxycarbonylmethyl)-benzenesulphonylamino]-benzofuran and ethanolic hydrochloric acid, ethanol and ammonium carbonate.

Yield: 36% of theory, $C_{27}H_{28}N_4O_5S(520.62)$; $R_f$-value: 0.22 (silica gel; dichloromethane/ethanol=4:1+glacial acetic acid); Mass spectrum (EKA): (M+H)$^+$=521.

EXAMPLE 116

2-[2-(4-Amidinophenyl)-ethyl-3-methyl-6-[N-(hydroxycarbonylmethyl)-quinoline-8-sulphonylamino]-benzofuran Prepared analogously to Example 3 from 2-[2-(4-amidinophenyl)-ethyl]-3-methyl-6-[N-(ethoxycarbonylmethyl)-quinoline-8-sulphonylamino]-benzofuran and sodium hydroxide solution.

Yield: 87% of theory, $C_{29}H_{26}N_4O_5S(542.63)$; $R_f$-value: 0.13 (silica gel; dichloromethane/ethanol=4:1+glacial acetic acid); Mass spectrum (EKA): (M+H)$^+$=543; (M+Na)$^+$=565.

EXAMPLE 117

2-[N-(4-Amidinophenyl)-aminomethyl]-3-methyl-6-[N-(hydroxycarbonylmethyl)-benzenesulphonylamino]-benzofuran Prepared analogously to Example 3 from 2-[N-(4-amidinophenyl)-aminomethyl]-3-methyl-6-[N-(ethoxycarbonylmethyl)-benzenesulphonylamino]-benzofuran and sodium hydroxide solution.

Yield: 79% of theory, $C_{25}H_{24}N_4O_5S(492.57)$; $R_f$-value: 0.12 (silica gel; dichloromethane/ethanol=4:1+glacial acetic acid); Mass spectrum (EKA): (M+H)$^+$=493; (M+Na)$^+$=515; (M+2Na)$^{++}$=269.

EXAMPLE 118

2-[N-(4-Amidinophenyl)-aminomethyl]-3-methyl-6-[N-(N'-(ethoxycarbonylmethyl)-aminocarbonylmethyl)-quinoline-8-sulphonylamino]-benzofuran Prepared analogously to Example 1e from 2-[N-(4-cyanophenyl)-aminomethyl]-3-methyl-6-[N-(N'-(ethoxycarbonylmethyl)-aminocarbonylmethyl)-quinoline-8-sulphonylamino]-benzofuran and ethanolic hydrochloric acid, ethanol and ammonium carbonate.

Yield: 81% of theory, $C_{32}H_{32}N_6O_6S(628.72)$; Mass spectrum (EKA): (M+H)$^+$=629; (M+H+Na)$^{++}$=326.

EXAMPLE 119

2-[N-(4-Amidinophenyl)-aminomethyl]-3-methyl-6-[N-(N'-(1H-tetrazol-5-yl)-aminocarbonylmethyl)-quinoline-8-sulphonylamino]-benzofuran a. 2-[N-(4-cyanophenyl)-aminomethyl]-3-methyl-6-[N-(N'-(1H-tetrazol-5-yl)-aminocarbonylmethyl)-quinoline-8- sulphonylamino]-benzofuran [0.53 g (1.0 mmol) of $^2$-[N-(4-cyanophenyl)-aminomethyl]-3-methyl-6-carboxymethyl-quinoline-8-sulphonylamino)-benzofuran are dissolved in 20 ml of tetrahydrofuran, mixed with 0.2 g (1.2 mmol) of carbonyldiimidazole and 0.1 g (1.0 mmol) of 5-amino-tetrazole and refluxed for 5 hours. The reaction mixture is concentrated by evaporation, the residue dissolved in ethanol and chromatographed on silica gel (methylene chloride +2.5% ethanol). The desired fractions are combined and concentrated by evaporation.

Yield: 0.11 g (19% of theory), $C_{29}H_{23}N_9O_4S$(593.64); $R_f$-value: 0.18 (silica gel; methylene chloride/ethanol=9:1); Mass spectrum: $(M-H)^-$=592.

b. 2-[N-(4-Amidinophenyl)-aminomethyl]-3-methyl-6-[N-(N'-(1H-tetrazol-5-yl)-aminocarbonylmethyl)-quinoline-8-sulphonylamino]-benzofuran Prepared analogously to Example 1e from 2-[N-(4-cyanophenyl)-aminomethyl]-3-methyl-6-[N-(N'-(1H-tetrazol-5-yl)-aminocarbonylmethyl)-quinoline-8-sulphonylamino]-benzofuran and hydrochloric acid/ammonium carbonate.

Yield: 97% of theory, $C_{29}H_{26}N_{10}O_4S$(610.67);

Mass spectrum (EKA): $(M+H)^+$=611; $(M+Na)^+$=633; $(M+H+Na)^{++}$=317.

EXAMPLE 120

2-[N-(4-Amidinophenyl)-aminomethyl]-3-methyl-6-[N-(1H-tetrazol-5-yl)-methyl)-quinoline-8-sulphonylamino]-benzofuran a. 5-Bromomethyl-1-(2-cyanoethyl)-tetrazole 1.50 g (7.85 mmol) of bromoacetic acid-(2-cyanoethyl)-amide are dissolved in 50 ml of methylene chloride and mixed with 508 mg (7.85 mmol) of sodium azide. At 0° C. a solution of 2.20 g (7.85 mmol) of trifluoroacetic acid anhydride in 5 ml of methylene chloride is added dropwise. After 22 hours at ambient temperature saturated sodium hydrogen carbonate solution is added and the resulting mixture is extracted 3 x with methylene chloride. The combined organic phases are dried over sodium sulphate and concentrated by evaporation. The crude product is chromatographed on silica gel, eluting first with methylene chloride, later with methylene chloride/ethanol (50:1). The desired fractions are combined and concentrated by evaporation.

Yield: 505 mg (30% of theory), $C_5H_6BrN_3$(216.06); Mass spectrum (EKA): $M^+$=215/217 (Br).

b. 2-[N-(4-cyanophenyl)-aminomethyl]-3-methyl-6-[N-[1-(2-cyanoethyl)-tetrazol-5-yl)-methyl]-quinoline-8-sulphonylamino]-benzofuran Prepared analogously to Example 1d from 2-[N-(4-cyanophenyl)-aminomethyl]-3-methyl-6-(quinoline-8-sulphonylamino)-benzofuran and 5-bromomethyl-1-(2-cyanoethyl)-tetrazole.

Yield: 98% of theory, $R_f$-value: 0.45 (silica gel; methylene chloride/ethanol=95:5).

c. 2-[N-(4-cyanophenyl)-aminomethyl]-3-methyl-6-[N-(1H-tetrazol-5-yl-methyl)-quinoline-8-sulphonylamino]-benzofuran 0.5 g (0.83 mmol) of 2-[N-(4-cyanophenyl)-aminomethyl]-3-methyl-6-[N-[1-(2-cyanoethyl)-tetrazol-5-yl-methyl]-quinoline-8-sulphonylamino]-benzofuran are dissolved in 50 ml of methylene chloride, mixed with 0.28 g (2.5 mmol) of potassium-tert.butoxide and stirred for 90 minutes at ambient temperature. The reaction mixture is concentrated by evaporation, the residue dissolved in water and acidified with glacial acetic acid. The precipitate formed is filtered off, washed with water and dried. The crude product is chromatographed on silica gel (methylene chloride +1–2% ethanol). The desired fractions are combined and concentrated by evaporation.

Yield: 110 mg (24% of theory), $R_f$-value: 0.43 (silica gel; dichloromethane/ethanol=9:1).

d. 2-[N-(4-Amidinophenyl)-aminomethyl]-3-methyl-6-[N-(1H-tetrazol-5-yl)-methyl)-quinoline-8-sulphonylamino]-benzofuran-hydrochloride Prepared analogously to Example 1e from 2-[N-(4-cyanophenyl)-aminomethyl]-3-methyl-6-[N-(1-tetrazol-5-yl-methyl)-quinoline-8-sulphonylamino]-benzofuran and hydrochloric acid/ammonium carbonate.

Yield: 97% of theory, $C_{28}H_{25}N_9O_3S$(567.66); Mass spectrum (EKA): $(M+H)^+$=568; $(M+Na)^+$=590; $(M+H+Na)^{++}$=295.6; $(M+2Na)^{++}$=306.7.

EXAMPLE 121

2-[2-(4-Amidinophenyl)-ethyl]-3-methyl-6-[N-(N'-(ethoxycarbonylmethyl-aminocarbonylmethyl)-quinoline-8-sulphonylamino]-benzofuran Prepared analogously to Example 1e from 2-[2-(4-cyanophenyl)-ethyl]-3-methyl-6-[N-(N'-(ethoxycarbonylmethyl)-aminocarbonylmethyl)-quinoline-8-sulphonylamino]-benzofuran and ethanolic hydrochloric acid, ethanol and ammonium carbonate.

Yield: 61% of theory, $C_{33}H_{33}N_5O_6S$(627.73); $R_f$-value: 0.25 (silica gel; dichloromethane/ethanol=4:1+glacial acetic acid); Mass spectrum (EKA): $(M+H)^+$=628; $(M+2H)^{++}$=314.7; $(M+H+Na)^{++}$=325.7.

EXAMPLE 122

2-[N-(4-Amidinophenyl)-aminomethyl]-3-methyl-6-[N-(N'-(hydroxycarbonylmethyl)-aminocarbonylmethyl)-quinoline-8-sulphonylamino]-benzofuran Prepared analogously to Example 3 from 2-[N-(4-amidinophenyl)-aminomethyl]-3-methyl-6-[N-(N'-(ethoxycarbonylmethyl)-aminocarbonylmethyl)-quinoline-8-sulphonylamino]-benzofuran and sodium hydroxide solution.

Yield: 69% of theory, $C_{30}H_{28}N_6O_6S$(600.67); Mass spectrum (EKA): $(M+H)^+$=601; $(M+Na)^+$=623; $(M+2H)^{++}$=301; $(M+H+Na)^{++}$=312; $(M+2Na)^{++}$=323.

EXAMPLE 123

2-[2-(4-Amidinophenyl)-ethyl]-4-methyl-7-[N-(1H-tetrazol-5-yl-methyl)-quinoline-8-sulphonylamino]-quinoline Prepared analogously to Example 1e from 2-[2-(4-cyanophenyl)-ethyl]-4-methyl-7-[N-(1H-tetrazol-5-yl-methyl)-quinoline-8-sulphonylamino]-quinoline and ethanolic hydrochloric acid, ethanol and ammonium carbonate.

Yield: 31% of theory, $C_{30}H_{27}N_9O_2S$(577.67); $R_f$-value: 0.15 (silica gel; dichloromethane/ethanol=4:1+glacial acetic acid); Mass spectrum (EKA): $(M+H)^+$=578; $(M+Na)^+$=600; $(M-H)-$=576.

EXAMPLE 124

1-methyl-2-[N-(4-(N-n-hexyloxycarbonylamidino)phenyl)-aminomethyl]-5-[N-(ethoxycarbonylmethyl)-quinoline-8-sulphonylamino]-benzimidazole Prepared analogously to Example 31 from 1-methyl-2-[N-(4-amidinophenyl)-aminomethyl]-5-[N-

(ethoxycarbonylmethyl)-quinoline-8-sulphonylamino]-benzimidazole and n-hexyl chloroformate.

Yield: 61% of theory, $C_{36}H_{41}N_7O_6S(699.84)$; $R_f$-value: 0.60 (silica gel; dichloromethane/methanol=9:1). Mass spectrum (EKA): $(M+H)^+=700$; $(M+Na)^+=722$; $(M+H+Na)^{++}=361.8$.

EXAMPLE 125

1-methyl-2-[N-(4-(N-n-octyloxycarbonylamidino)phenyl)-aminomethyl]-5-[N-(ethoxycarbonylmethyl)-quinoline-8-sulphonylamino]-benzimidazole Prepared analogously to Example 31 from 1-methyl-2-[N-(4-amidinophenyl)-aminomethyl]-5-[N-(ethoxycarbonylmethyl)-quinoline-8-sulphonylamino]-benzimidazole and n-octyl chloroformate.

Yield: 65% of theory, $C_{38}H_{45}N_7O_6S(727.89)$; $R_f$-value: 0.58 (silica gel; dichloromethane/methanol=9:1); Mass spectrum (EKA): $(M+H)^+=728$; $(M+Na)^+=750$; $(M+H+Na)^{++}=375.8$.

EXAMPLE 126

1-methyl-2-[N-(4-(N-n-butyloxycarbonylamidino)phenyl)-aminomethyl]-5-[N-(ethoxycarbonylmethyl)-quinoline-8-sulphonylamino]-benzimidazole Prepared analogously to Example 31 from 1-methyl-2-[N-(4-amidinophenyl)-aminomethyl]-5-[N-(ethoxycarbonylmethyl)-quinoline-8-sulphonylamino]-benzimidazole and n-butylchloroformate.

Yield: 64% of theory, $C_{34}H_{37}N_7O_6S(671.78)$; $R_f$-value: 0.57 (silica gel; dichloromethane/methanol=9:1); Mass spectrum (EKA): $(M+H)^+=672$; $(M+Na)^+=694$; $(M+H+Na)^{++}=347.8$.

EXAMPLE 127

1-methyl-2-[N-(4-amidino-2-methoxy-phenyl)-aminomethyl]-5-(N-methyl-benzenesulphonylamino)-benzimidazole Prepared analogously to Example 1e from 1-methyl-2-[N-(4-cyano-2-methoxy-phenyl)-aminomethyl]-5-(N-methyl-benzenesulphonylamino)-benzimidazole and ethanolic hydrochloric acid, ethanol and ammonium carbonate.

Yield: 57% of theory, $C_{24}H_{26}N_6O_3S(478.6)$; Mass spectrum (EKA): $(M+H)^+=479$; $(M+Na)^+=501$.

EXAMPLE 128

1-methyl-2-[N-(4-amidinophenyl)-aminomethyl]-5-(N-methyl-phenylaceylamino)-benzimidazole Prepared analogously to Example 1e from 1-methyl-2-[N-(4-cyanophenyl)-aminomethyl]-5-(N-methyl-phenylaceylamino)-benz-imidazole and ethanolic hydrochloric acid, ethanol and ammonium carbonate.

Yield: 54% of theory, $C_{25}H_{26}N_6O(426.53)$; $R_f$-value: 0.27 (silica gel; dichloromethane/methanol=5:1); Mass spectrum (EKA): $(M+H)^+=427$; $(M+2H)^{++}=214$.

EXAMPLE 129

1-methyl-2-[N-(4-(N-benzoylamidino)-phenyl)-aminomethyl]-5-[N-(ethoxycarbonylmethyl)-quinoline-8-sulphonylamino]-benzimidazole Prepared analogously to Example 31 from 1-methyl-2-[N-(4-amidino-phenyl)-aminomethyl]-5-[N-(ethoxycarbonylmethyl)-quinoline-8-sulphonylamino]-benzimidazole and benzoyl chloride.

Yield: 54% of theory, $C_{36}H_{33}N_7O_5S(675.77)$; Mass spektrum: $(M+H)^+=676$; $(M+Na)^+=698$.

EXAMPLE 130

1-methyl-2-[N-(4-(N-benzoylamidino)-phenyl)-aminomethyl]-5-[N-(n-propyloxycarbonylmethyl)-quinoline-8-sulphonylamino]-benzimidazole Prepared analogously to Example 31 from 1-methyl-2-[N-(4-amidino-phenyl)-aminomethyl]-5-[N-(n-propyloxycarbonylmethyl)-quinoline-8-sulphonylamino]-benzimidazole and benzoyl chloride.

Yield: 52% of theory, $C_{37}H_{35}N_7O_5S(689.77)$; Mass spektrum: $(M+H)^+=690$; $(M+Na)^+=712$.

EXAMPLE 131

Dry Ampoule Containing 75 mg of Active Substance Per 10 ml

Composition:

| | |
|---|---|
| Active substance | 75.0 mg |
| Mannitol | 50.0 mg |
| water for injections | ad 10.0 ml |

Preparation:

Active substance and mannitol are dissolved in water. After packaging the solution is freeze-dried. To produce the solution ready for use, the product is dissolved in water for injections.

EXAMPLE 132

Dry Ampoule Containing 35 mg of Active Substance Per 2 ml

Composition:

| | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

EXAMPLE 133

Tablet Containing 50 mg of Active Substance

Composition:

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

EXAMPLE 134

Tablet Containing 350 mg of Active Substance

Preparation:

| (1) Active substance | 350.0 mg |
|---|---|
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE 135

Capsules Containing 50 mg of Active Substance

Composition:

| (1) Active substance | 50.0 mg |
|---|---|
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatin capsules in a capsule filling machine.

EXAMPLE 136

Capsules Containing 350 mg of Active Substance

Composition:

| (1) Active substance | 350.0 mg |
|---|---|
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatin capsules in a capsule filling machine.

EXAMPLE 137

Suppositories Containing 100 mg of Active Substance 1 suppository contains:

| Active substance | 100.0 mg |
|---|---|
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Method:

The polyethyleneglycol is melted together with polyethylenesorbitan monostearate. At 40° C. the ground active substance is homogeneously dispersed in the melt. It is cooled to 38° C. and poured into slightly chilled suppository moulds.

What is claimed is:

1. A disubstituted bicyclic heterocycle of the formula

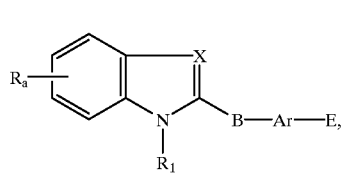

(I)

wherein

X is a nitrogen atom or a methine group optionally substituted by a $C_{1-3}$-alkyl group;

$R_1$ is a hydrogen atom or a $C_{1-6}$-alkyl group;

B is an ethylene group optionally substituted by one or two $C_{1-3}$-alkyl groups, wherein a methylene moiety of the ethylene group, which is linked to either the bicyclic heteroaromatic group or the Ar group, is optionally replaced by an oxygen or sulphur atom, or by a sulphinyl, sulphonyl, carbonyl, or —$NR_1$— group, wherein $R_1$ is as hereinbefore defined, or B is a straight-chained $C_{3-5}$-alkylene group, in which a methylene moiety, which is linked neither to the bicyclic heteroaromatic group nor to the Ar group, is replaced by an —$NR_1$— group, wherein $R_1$ is as hereinbefore defined;

E is a cyano or $R_b$NH—C(=NH)— group, wherein
  $R_b$ is a hydrogen atom, a hydroxy group, a $C_{1-3}$-alkyl group, or a group which may be cleaved in vivo;

Ar is a phenylene or naphthylene group optionally substituted by a fluorine, chlorine, or bromine atom, or by a trifluoromethyl, $C_{1-3}$-alkyl, or $C_{1-3}$-alkoxy group; or a thienylene, thiazolylene, pyridinylene, pyrimidinylene, pyrazinylene, or pyridazinylene group optionally substituted in the carbon skeleton by a $C_{1-3}$-alkyl group; and $R_a$ is a phenyl-$C_{1-3}$-alkoxy group, an amino group, a $C_{1-3}$-alkylamino group substituted at the nitrogen atom by a phenyl-$C_{1-3}$-alkyl group, or an $R_3$—CO—$R_4$N— or $R_3$—$SO_2$—$R_4$N— group wherein $R_3$ is a $C_{1-5}$-alkyl, phenyl-$C_{1-3}$-alkyl, $C_{3-7}$-cycloalkyl, phenyl, naphthyl, pyridyl, quinolyl, isoquinolyl, tetrahydroquinolyl or tetrahydroisoquinolyl group and $R_4$ is a hydrogen atom, $C_{1-5}$-alkyl or phenyl-$C_{1-3}$-alkyl group, each of which is substituted in the alkyl moiety by a group which may be converted in vivo into a carboxy group, by a carboxy or tetrazolyl group, by an aminocarbonyl or $C_{1-3}$-alkylaminocarbonyl group, each of which is additionally substituted at the nitrogen atom by a group which may be converted in vivo into a carboxy-$C_{1-3}$-alkyl group or by a carboxy group, a $C_{2-5}$-alkyl group terminally substituted by a di-($C_{1-3}$-alkyl)-amino group, or a $C_{3-7}$-cycloalkyl group, or a tautomer or pharmaceutically acceptable salt thereof.

2. A disubstituted bicyclic heterocycle of the formula I according to claim 1, wherein X is a nitrogen atom or a methine group optionally substituted by a methyl group;

$R_1$ is a hydrogen atom or a methyl group;

B is an ethylene group optionally substituted by one or two methyl groups, wherein a methylene moiety of the ethylene group, which is linked to either the bicyclic heteroaromatic group or Ar group, may be replaced by an oxygen or sulphur atom, by a carbonyl or —$NR_1$— group, wherein $R_1$ is as hereinbefore defined, or B also is an n-propylene group wherein the central methylene moiety is replaced by an —$NR_1$— group wherein $R_1$ is as hereinbefore defined;

E is a cyano or $R_b$NH—C(=NH)— group wherein $R_b$ is a hydrogen atom, a $C_{1-8}$-alkyloxy-carbonyl, $C_{5-7}$-cycloalkyloxy-carbonyl, benzoyl, nicotinoyl, or isonicotinoyl group;

Ar is a phenylene group optionally substituted by a fluorine, chlorine or bromine atom, by a trifluoromethyl, methyl or methoxy group, or a thienylene group optionally substituted in the carbon skeleton by a methyl group; and $R_a$ is a benzyloxy group, an amino group, a $C_{1-3}$-alkylamino group, which is additionally substituted at the nitrogen atom by a benzyl group, or an $R_3$—CO—$R_4$N— or $R_3$—$SO_2$—$R_4$N— group wherein $R_3$ is a $C_{1-4}$-alkyl, benzyl, $C_{5-7}$-cycloalkyl, phenyl, pyridyl, quinolyl, isoquinolyl, tetrahydroquinolyl, or tetrahydroisoquinolyl group, and $R_4$ is a hydrogen atom, a $C_{1-3}$-alkyl group substituted by a carboxy, $C_{1-3}$-alkoxy-carbonyl, tetrazolyl, aminocarbonyl or $C_{1-3}$-alkylaminocarbonyl group, whilst the aminocarbonyl and $C_{1-3}$-alkylaminocarbonyl group are each additionally substituted at the nitrogen atom by a carboxy-$C_{1-3}$-alkyl or $C_{1-3}$-alkoxycarbonyl-$C_{1-3}$-alkyl group, or a $C_{2-3}$-alkyl group terminally substituted by a di-($C_{1-3}$-alkyl)-amino group, or a tautomer or pharmaceutically acceptable salt thereof.

3. The disubstituted bicyclic heterocycle of the formula I according to claim 1, wherein X is a nitrogen atom or a methine group optionally substituted by a methyl group;

$R_1$ is a hydrogen atom or a methyl group;

B is an ethylene group optionally substituted by one or two methyl groups, wherein a methylene moiety of the ethylene group, which is linked to either the bicyclic heteroaromatic group or the Ar group, may be replaced by an oxygen or sulphur atom, by a carbonyl or —$NR_1$— group, wherein $R_1$ is as hereinbefore defined, or B is an n-propylene group wherein the central methylene moiety is replaced by an —$NR_1$— group, wherein $R_1$ is as hereinbefore defined;

E is an $R_b$NH—C(=NH)— group wherein $R_b$ is a hydrogen atom, a $C_{1-8}$-alkyloxy-carbonyl, $C_{5-7}$-cycloalkyloxy-carbonyl or benzoyl group;

Ar is a phenylene group optionally substituted by a fluorine, chlorine, or bromine atom, by a trifluoromethyl, methyl, or methoxy group, or a thienylene group optionally substituted in the carbon skeleton by a methyl group; and $R_a$ is a benzyloxy group, an amino group, a $C_{1-3}$-alkylamino group additionally substituted at the nitrogen atom by a benzyl group, an $R_3$—CO—$R_4$N— or $R_3$—$SO_2$—$R_4$N— group wherein $R_3$ is a $C_{1-4}$-alkyl, benzyl, $C_{5-7}$-cycloalkyl, phenyl, pyridyl, quinolyl, isoquinolyl, tetrahydroquinolyl or tetrahydroisoquinolyl group and $R_4$ is a hydrogen atom, a $C_{1-3}$-alkyl group which is substituted by a carboxy, $C_{1-3}$-alkoxy-carbonyl, tetrazolyl, aminocarbonyl or $C_3$-alkylaminocarbonyl group, wherein the aminocarbonyl and $C_{1-3}$-alkylaminocarbonyl group are each additionally substituted at the nitrogen atom by a carboxy-$C_{1-3}$-alkyl or $C_{1-3}$-alkoxycarbonyl-$C_{1-3}$-alkyl group, or a $C_{2-3}$-alkyl group terminally substituted by a di-($C_{1-3}$-alkyl)-amino group, or a tautomer or pharmaceutically acceptable salt thereof.

4. The disubstituted bicyclic heterocycle of the formula I according to claim 3, wherein $R_a$ in the 5 position is an $R_3$—CO—$R_4$N— or $R_3$—$SO_2$—$R_4$N— group, wherein $R_3$ and $R_4$ are as hereinbefore defined, or a tautomer or pharmaceutically acceptable salt thereof.

5. The disubstituted bicyclic heterocycle of the formula Ia

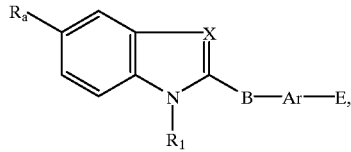

(Ia)

wherein

X is a methine group or a nitrogen atom;

$R_1$ is a methyl group;

B is an ethylene group, wherein the methylene moiety linked to Ar is optionally replaced by an oxygen atom or a imino group, Ar is a 1,4-phenylene group;

E is an $R_b$NH—C(=NH)— group; and $R_a$ is an $R_3$—CO—$R_4$N— or $R_3$—$SO_2$—$R_4$N— group, wherein $R_4$ is a methyl group substituted by a carboxy, $C_{1-3}$-alkoxy-carbonyl, carboxymethylaminocarbonyl or $C_{1-3}$-alkoxy-carbonylmethylaminocarbonyl group, and $R_3$ is an isoquinolin-8-yl group, or a tautomer or pharmaceutically acceptable salt thereof.

6. The disubstituted bicyclic heterocycle of the formula Ia according to claim 5, wherein $R_a$ is an $R_3$—$SO_2$—$R_4$N— group, or a tautomer or pharmaceutically acceptable salt thereof.

7. A compound of the formula I in accordance with claim 1, selected from the group consisting of:

(a) 1-methyl-2-[(4-amidinophenyl)-oxymethyl]-5-[N-(hydroxycarbonylmethyl)-quinoline-8-sulphonylamino]-benzimidazole;

(b) 1-methyl-2-[2-(4-amidinophenyl)-ethyl]-5-[N-(N'-(hydroxycarbonylmethyl)-aminocarbonylmethyl)-quinoline-8-sulphonylamino]-benzimidazole;

(c) 1-methyl-2-[N-(4-amidinophenyl)-aminomethyl]-5-[N-(hydroxycarbonylmethyl)-quinoline-8-sulphonylamino]-benzimidazole; and (d) 1-methyl-2-[N-(4-amidinophenyl)-aminomethyl]-5-[N-(hydroxycarbonylmethyl)-quinoline-8-sulphonylamino]-indole, or a tautomer or pharmaceutically acceptable salt thereof.

8. A pharmaceutical composition containing a compound according to claim 1, 2, 3, 4, 5, 6, 7, or 10, wherein E is an $R_b$NH—C(=NH)— group.

9. A method for the treatment of venous and arterial thrombotic diseases which comprises administering to a host in need of such treatment an antithrombotic amount of a compound in accordance with claim 1, 2, 3, 4, 5, 6, 7, or 10, wherein E is an $R_b$NH—C(=NH)— group.

10. A compound of the formula I in accordance with claim 1, comprising 1-methyl-2-[N-(4-amidinophenyl)-aminomethyl]-5-[N-(hydroxycarbonylmethyl)-quinoline-8-sulphonylamino]-benzimidazole.

* * * * *

UNITED STATES PATENT AND TRADEMARK OFFICE
CERTIFICATE OF CORRECTION

PATENT NO.    : 6,121,308
DATED         : September 19, 2000
INVENTOR(S)   : Haul et al.

It is certified that error appears in the above-identified patent and that said Letters Patent is hereby corrected as shown below:

<u>Title page,</u>
Item [73] Assignee "Boehringer Ingelheim KG" should read --Boehringer Ingleheim Pharma KG --.

Signed and Sealed this

Twenty-first Day of August, 2001

Attest:

NICHOLAS P. GODICI
Attesting Officer — Acting Director of the United States Patent and Trademark Office